(12) United States Patent
Kassab et al.

(10) Patent No.: US 8,382,651 B2
(45) Date of Patent: *Feb. 26, 2013

(54) DEVICES, SYSTEMS, AND METHODS TO FACILITATE HEART FUNCTION

(75) Inventors: Ghassan S. Kassab, Zionsville, IN (US); Jose A. Navia, Sr., Buenos Aires (AR)

(73) Assignee: CVDevices, LLC, Zionsville, IN (US)

( * ) Notice: Subject to any disclaimer, the term of this patent is extended or adjusted under 35 U.S.C. 154(b) by 69 days.

This patent is subject to a terminal disclaimer.

(21) Appl. No.: 12/596,972

(22) PCT Filed: Apr. 18, 2008

(86) PCT No.: PCT/US2008/060870
§ 371 (c)(1),
(2), (4) Date: Oct. 21, 2009

(87) PCT Pub. No.: WO2008/134267
PCT Pub. Date: Nov. 6, 2008

(65) Prior Publication Data
US 2012/0130151 A1 May 24, 2012

(51) Int. Cl.
*A61M 1/12* (2006.01)
(52) U.S. Cl. .......................... 600/16; 600/18
(58) Field of Classification Search ............ 600/16–18
See application file for complete search history.

(56) References Cited

U.S. PATENT DOCUMENTS

| | | |
|---|---|---|
| 3,583,404 A | 6/1971 | McWhorter |
| 3,630,207 A | 12/1971 | Kahn et al. |
| 4,946,457 A | 8/1990 | Elliott |
| 4,991,578 A | 2/1991 | Cohen |
| 5,195,968 A | 3/1993 | Lundquist et al. |
| 5,292,332 A | 3/1994 | Lee |
| 5,715,817 A | 2/1998 | Stevens-Wright et al. |
| 5,972,013 A | 10/1999 | Schmidt |
| 6,113,611 A | 9/2000 | Allen et al. |
| 6,200,303 B1 | 3/2001 | Verrior et al. |
| 6,241,706 B1 | 6/2001 | Leschinsky et al. |
| 6,338,345 B1 | 1/2002 | Johnson et al. |
| 6,432,039 B1 | 8/2002 | Wardle |
| 6,500,167 B1 | 12/2002 | Webster, Jr. |
| 6,511,412 B1 | 1/2003 | Freed et al. |
| 6,595,982 B2 | 7/2003 | Sekino et al. |
| 6,613,062 B1 | 9/2003 | Leckrone et al. |
| 6,626,821 B1 * | 9/2003 | Kung et al. ............. 600/16 |
| 6,626,930 B1 | 9/2003 | Allen et al. |
| 6,663,633 B1 | 12/2003 | Pierson, III |
| 6,692,458 B2 | 2/2004 | Forman et al. |
| 6,776,784 B2 | 8/2004 | Ginn |

(Continued)

OTHER PUBLICATIONS

Uchida et al. "Angiogenic therapy of acute myocardial infarction by intrapericardial injection of . . . " American Heart Journal, vol. 130, No. 6, pp. 1182-1188 (Dec. 1995).

(Continued)

*Primary Examiner* — Carl H Layno
*Assistant Examiner* — Allen Porter, Jr.
(74) *Attorney, Agent, or Firm* — Ice Miller LLP

(57) ABSTRACT

Devices, systems, and methods for accessing tissue, including the internal and external tissues of the heart, are disclosed. At least some of the embodiments disclosed herein provide access to the internal and external tissues of the heart to assist heart function. In at least one embodiment, a suction/infusion catheter is used to deliver gas to a pericardial space surrounding a heart.

29 Claims, 39 Drawing Sheets

U.S. PATENT DOCUMENTS

| | | | |
|---|---|---|---|
| 6,837,893 | B2 | 1/2005 | Miller |
| 6,890,295 | B2 | 5/2005 | Michels |
| 6,918,890 | B2 | 7/2005 | Schmidt |
| 6,991,616 | B2 | 1/2006 | Bencini et al. |
| 7,029,468 | B2 | 4/2006 | Honebrink |
| 7,081,125 | B2 | 7/2006 | Edwards et al. |
| 7,326,231 | B2 | 2/2008 | Phillips et al. |
| 7,367,959 | B2 * | 5/2008 | Nardi .......................... 604/4.01 |
| 7,842,068 | B2 | 11/2010 | Ginn |
| 7,931,628 | B2 | 4/2011 | Zhu et al. |
| 7,942,897 | B2 | 5/2011 | Lafontaine |
| 2001/0041821 | A1* | 11/2001 | Wilk .............................. 600/16 |
| 2002/0072768 | A1 | 6/2002 | Ginn |
| 2002/0091354 | A1 | 7/2002 | Navia, Sr. |
| 2002/0165561 | A1 | 11/2002 | Ainsworth |
| 2002/0168317 | A1 | 11/2002 | Daighighian et al. |
| 2003/0009145 | A1 | 1/2003 | Struijker-Boudier et al. |
| 2003/0109852 | A1 | 6/2003 | Peterson et al. |
| 2003/0225420 | A1 | 12/2003 | Wardle |
| 2004/0008853 | A1 | 1/2004 | Pelrine et al. |
| 2004/0010216 | A1 | 1/2004 | Zhu et al. |
| 2004/0018228 | A1 | 1/2004 | Fischell et al. |
| 2004/0086479 | A1 | 5/2004 | Grinstaff et al. |
| 2004/0087938 | A1 | 5/2004 | Leckrone et al. |
| 2004/0230131 | A1 | 11/2004 | Kassab et al. |
| 2005/0054994 | A1 | 3/2005 | Cioanta et al. |
| 2005/0096496 | A1* | 5/2005 | Spence .......................... 600/16 |
| 2005/0113760 | A1 | 5/2005 | Chachques et al. |
| 2005/0256450 | A1 | 11/2005 | Palasis et al. |
| 2005/0261673 | A1 | 11/2005 | Bonner |
| 2006/0106442 | A1 | 5/2006 | Richardson et al. |
| 2006/0207612 | A1 | 9/2006 | Jackson et al. |
| 2006/0217764 | A1 | 9/2006 | Abbott et al. |
| 2006/0240113 | A1 | 10/2006 | Hunter et al. |
| 2007/0010708 | A1 | 1/2007 | Ness |
| 2007/0010793 | A1 | 1/2007 | Callas et al. |
| 2007/0068523 | A1 | 3/2007 | Fishman |

OTHER PUBLICATIONS

International Searching Authority, International Search Report, mailed Sep. 11, 2008 (PCT/U507/15207).

International Searching Authority, International Written Opinion, mailed Sep. 11, 2008 (PCT/US07/15207).

International Searching Authority, International Search Report, mailed Oct. 1, 2008 (PCT/US08/53061).

International Searching Authority, International Written Opinion, mailed Oct. 1, 2008 (PCT/US08/53061).

International Searching Authority, International Search Report, mailed Aug. 29, 2008 (PCT/US08/56666).

International Searching Authority, International Written Opinion, mailed Aug. 29, 2008 (PCT/US08/56666).

International Searching Authority, International Search Report, mailed Nov. 18, 2008 (PCT/US08/60870).

International Searching Authority, International Written Opinion, mailed Nov. 18, 2008 (PCT/US08/60870).

Anstadt M.P., et al. (2002) "Non-blood contacting biventricular support for severe heart failure." Ann Thorac Surg 73(2): 556-562.

Azevedo C.F., et al (2005) "The effect of intra-aortic ballon conterpulsation on left ventricular functional recovery . . . etc." Eur Heart J 26(12): 1235-1241.

Barnard H., (1898) "The functions of the pericarium." J. Physiol. 22: 43-47.

Baughman K.L. & Jarcho J.A., (2007) "Bridge to Life—Cardiac Mechanical Support." N.Engl J Med 357(9): 846-849.

Carabello B.A., (2006) "Understanding Coronary Blood Flow: The Wave of the Future." Circulation 113(14): 1721-1722.

Davies J.E., et al. (2006) "Evidence of a dominant backward-propagating "suction" wave responsible for diastolic . . . etc." Circulation 113(14): 1768-1778.

deVries G., et al. (2001) A novel technique for measurement of pericardial pressure.: Am J Physiol Heart Circ Physiol 280(6): H2815-22.

Gibbons Kroeker C. A., et al, (2006) "A 2D FE model of the heart demonstrates the role of the pericardium . . . etc." Am J Physiol Heart Circ Physiol 291(5): H2229-36.

Goto Y. & LeWinter M.M., (1990) Nonuniform regional deformation of the pericardium during the cardiac cycle in dogs.: Circ Res 67(5): 1107-14.

Gregg D. E. & Sabiston D.C., Jr., (1957) "Effect of cardiac contractioon on coronary blood flow." Circulation 15(1): 14-20.

Hamilton D.R., et al. (1994) "Right atrial and right ventricular transmural pressures in dogs and humans. Effects of the pericardium." Circulation 90(5): 2492-500.

Huang, Engineering RGC-Modified Loposomes for Targeted Drug Delivery to Activated Platelets, PhD Thesis, Case Western Reserve University, Aug. 2006.

Lindstedt S., et al. (2007) "Blood Flow Chages in Normal and Ischemic Myocardium During Topically Applied Negative Pressure." Ann Thorac Surg 84(2): 568-573.

Mancini D. & Burkhoff D. (2005) "Mechanical Device-Based Methods of Managing and Treating Heart Failure." Circulation 112(3): 438-448.

Pifarre R., et al. (1969) "Helium in the Prevention of Ventricular Fibrillation." Chest 56(2): 135-138.

* cited by examiner

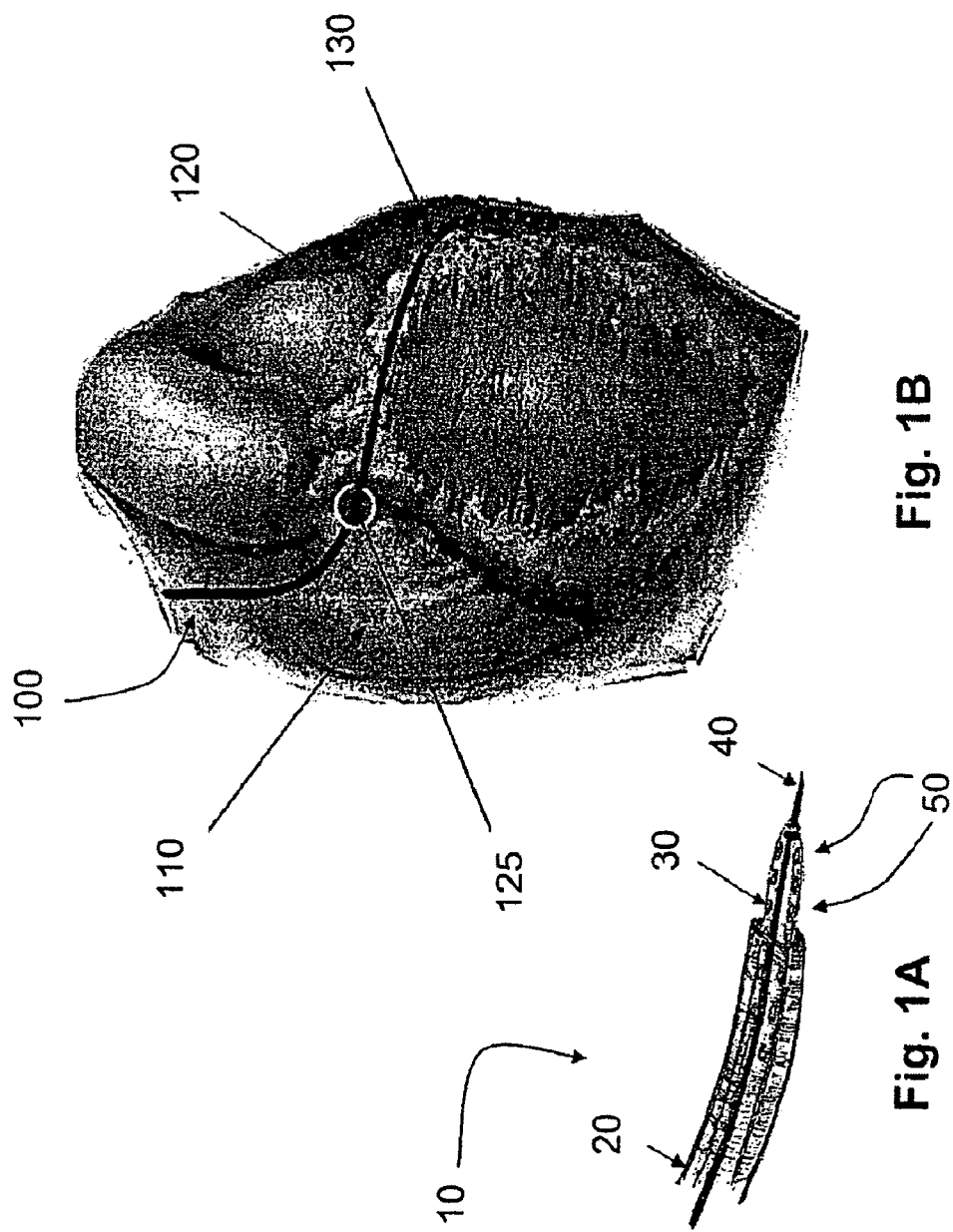

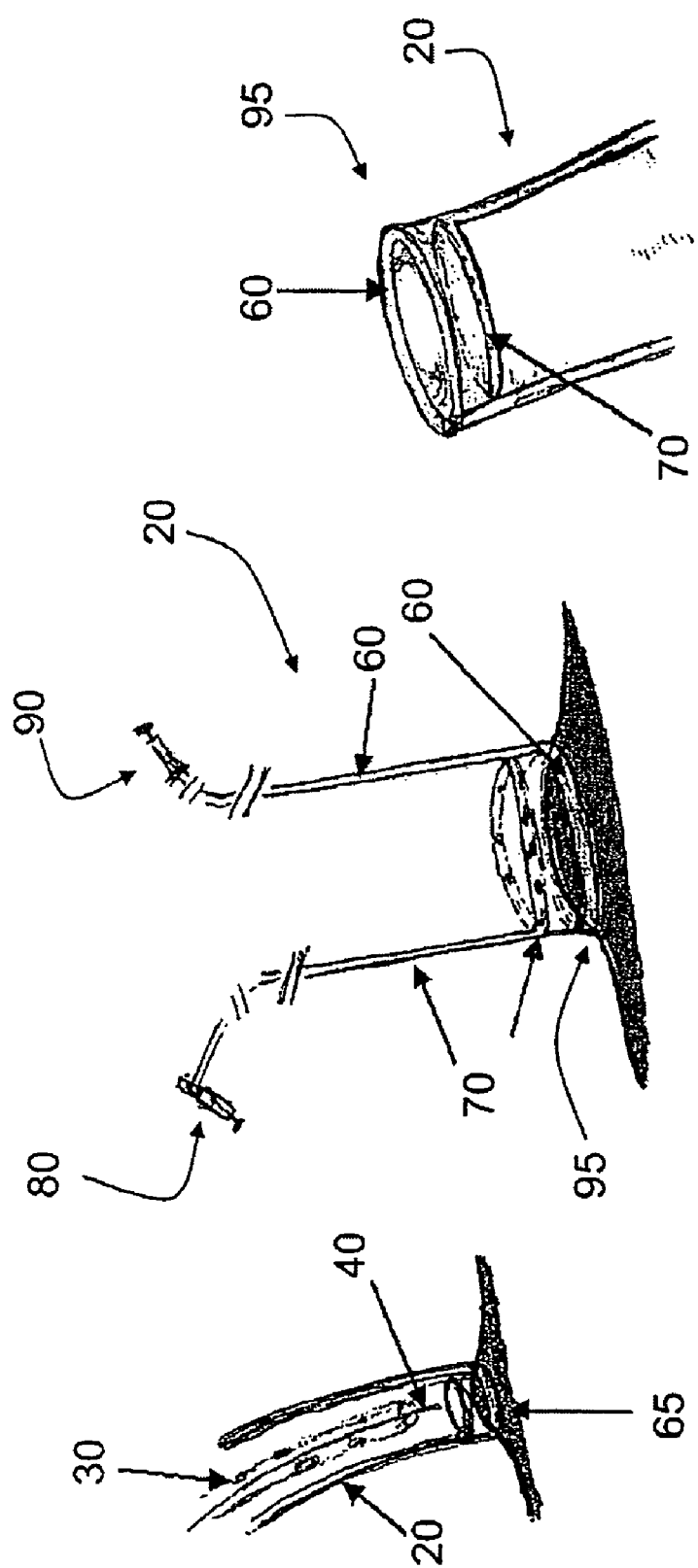

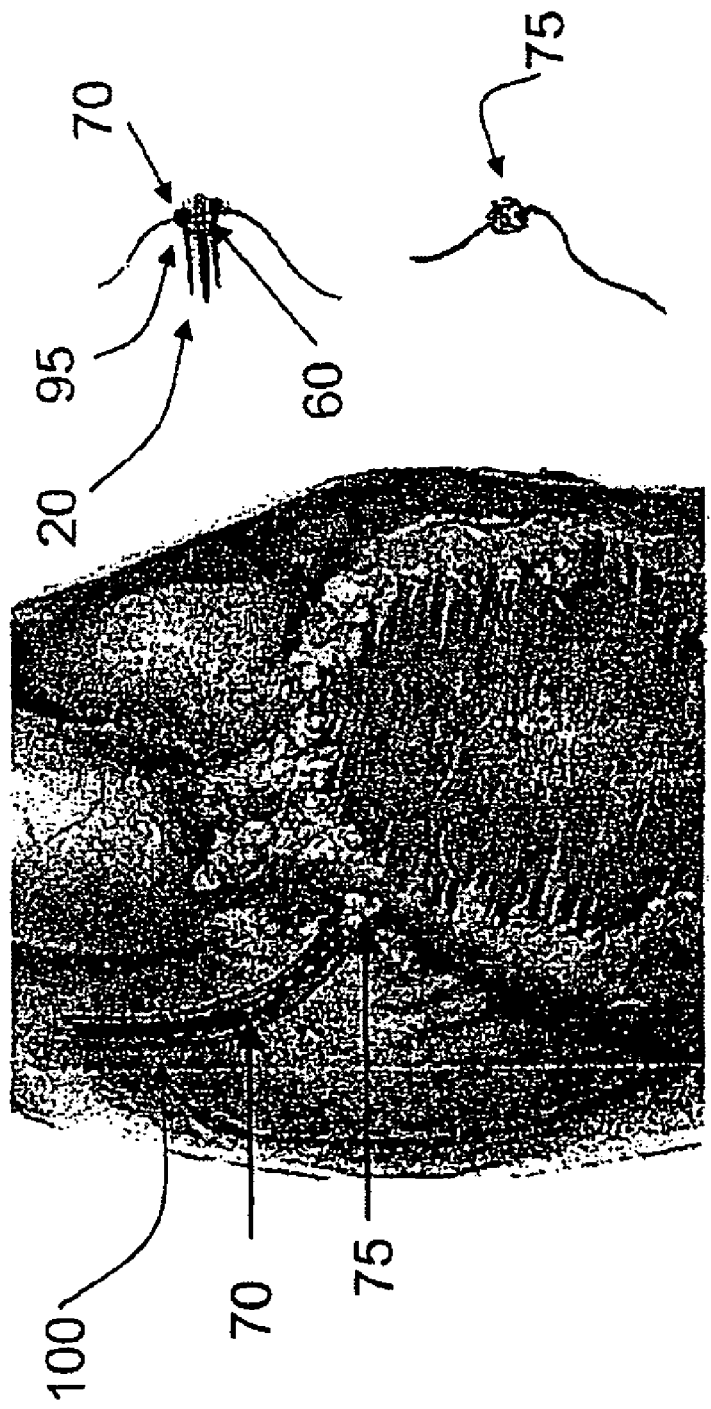

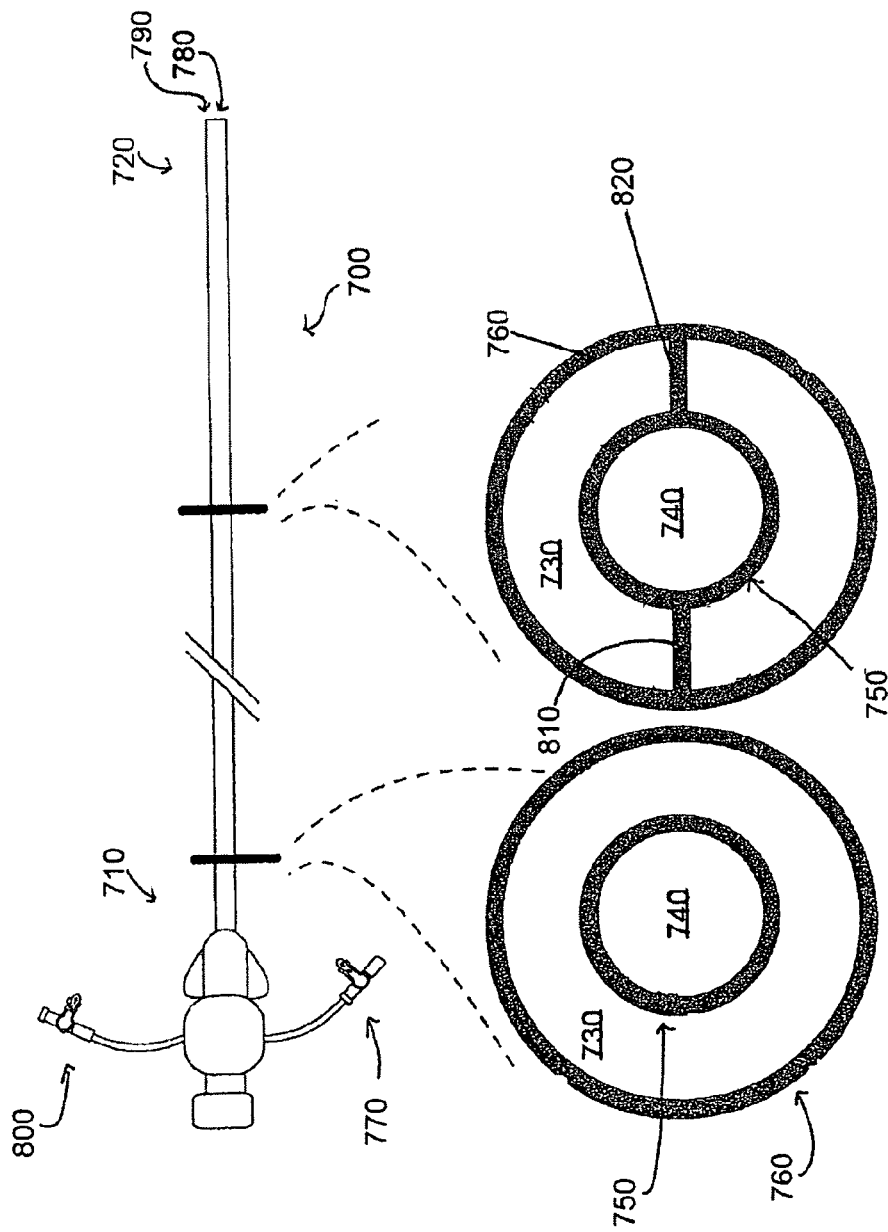

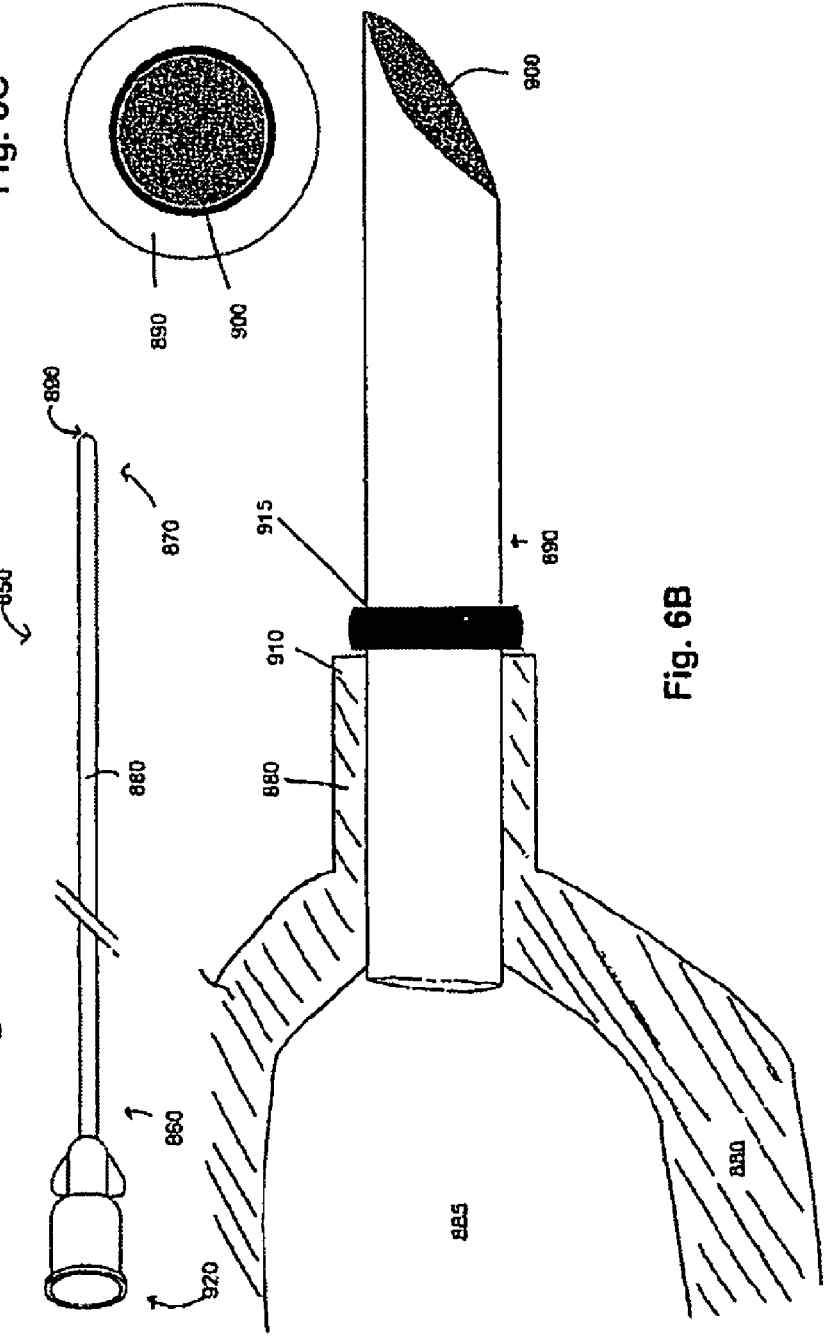

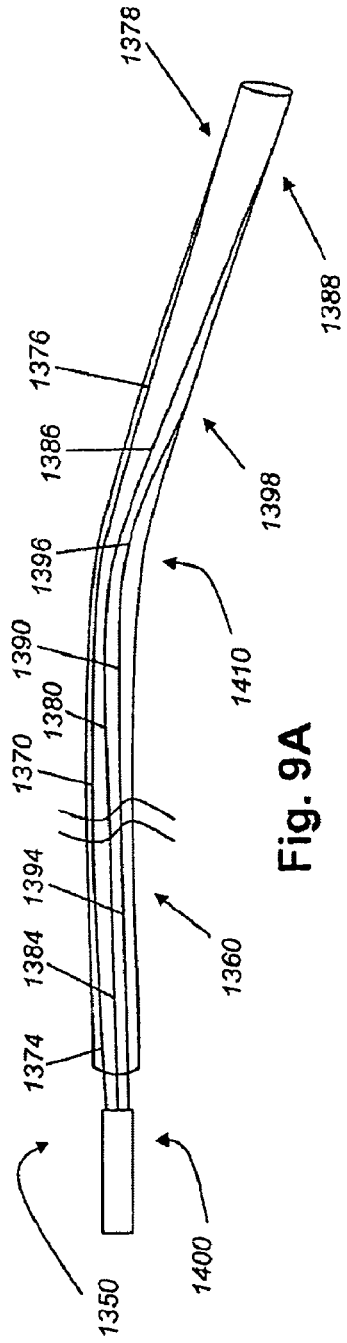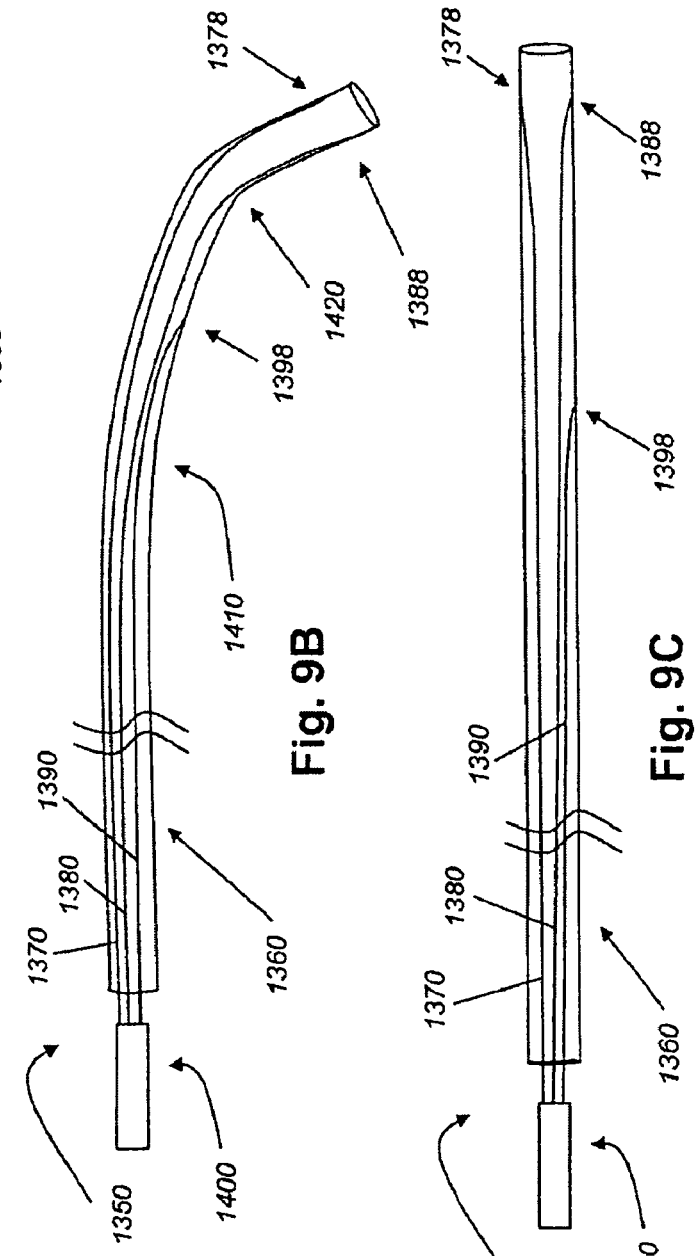

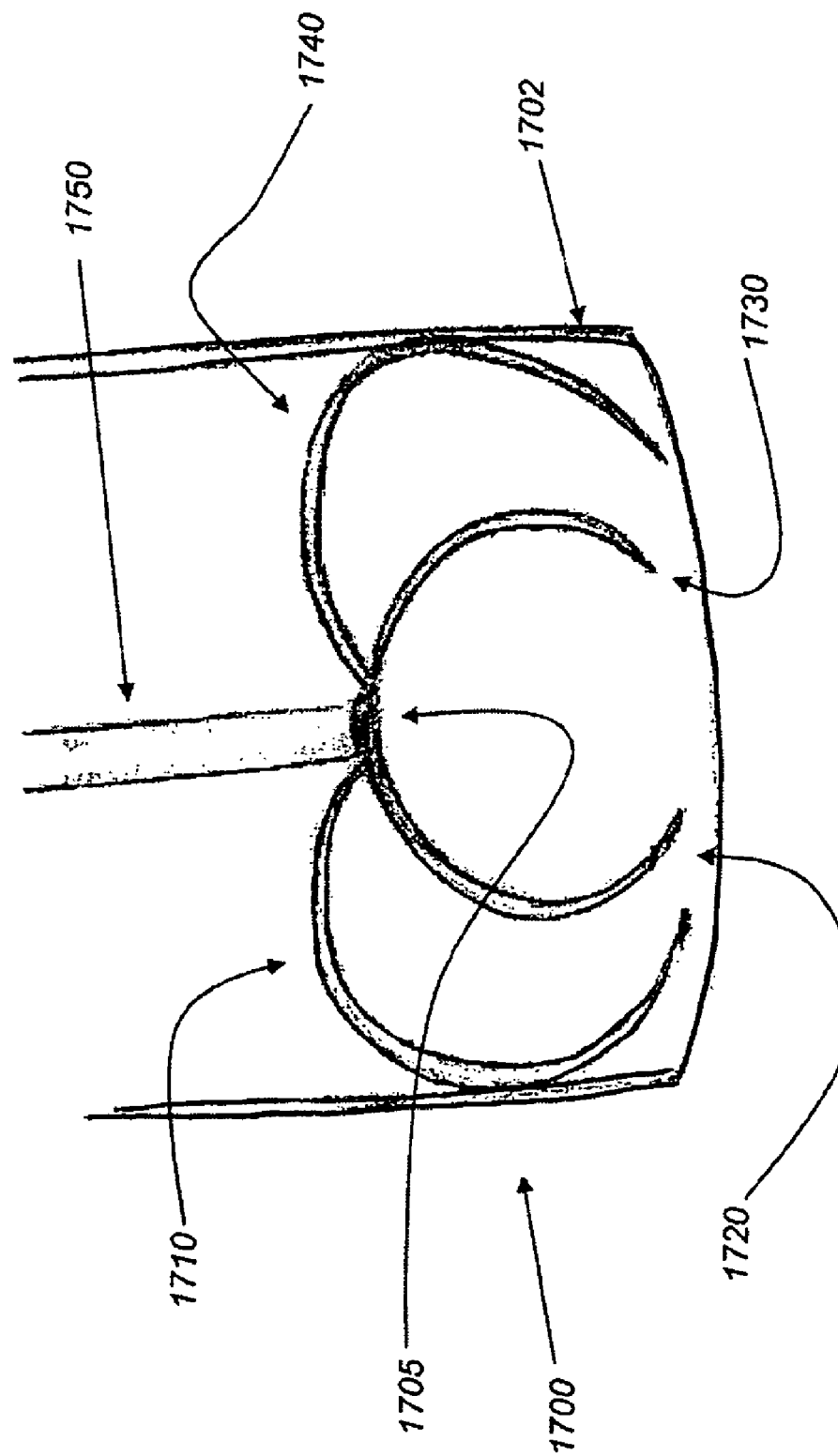

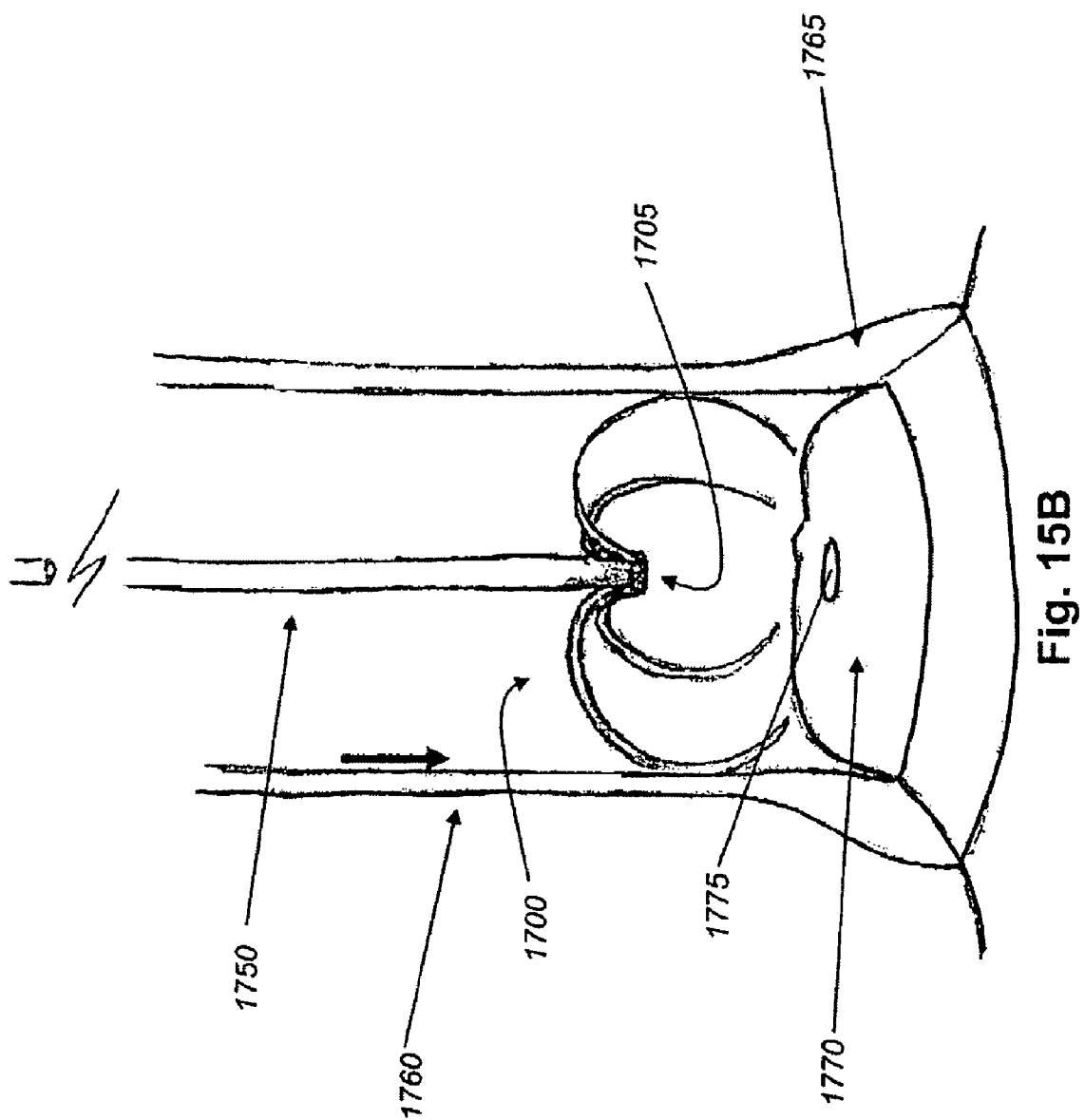

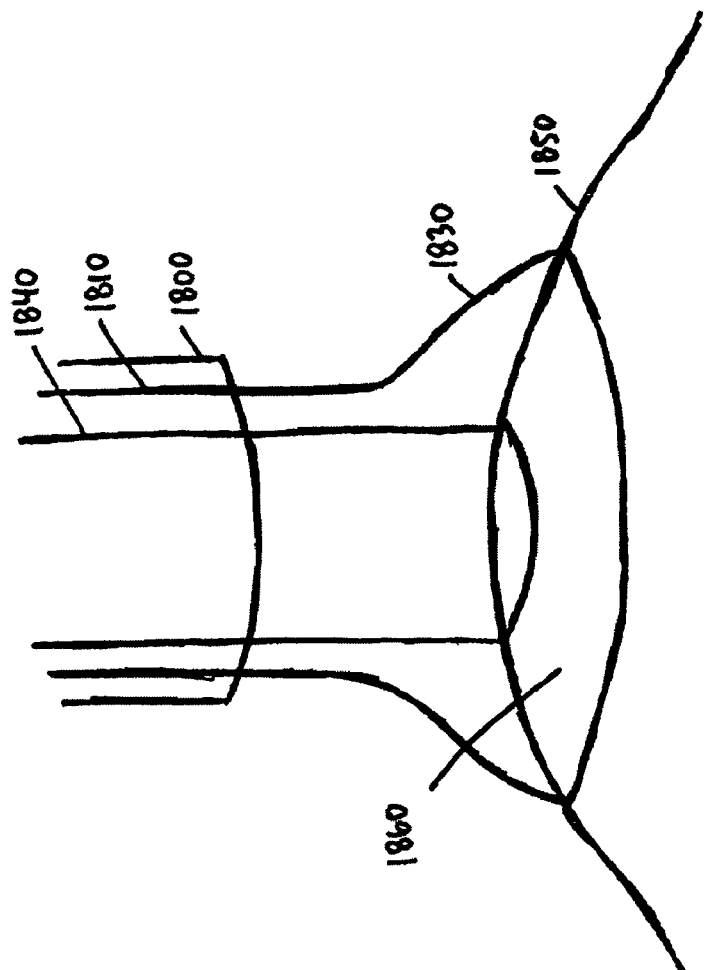
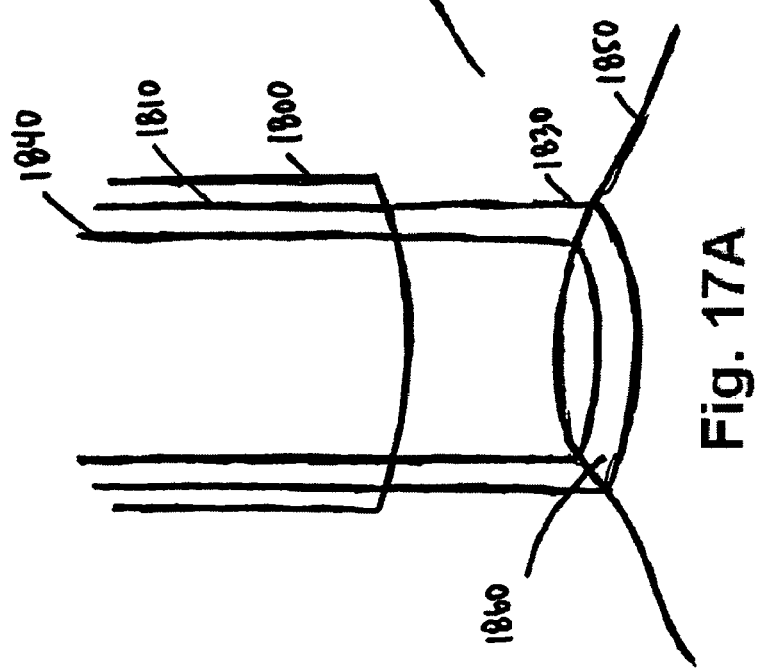
Fig. 17B
Fig. 17A

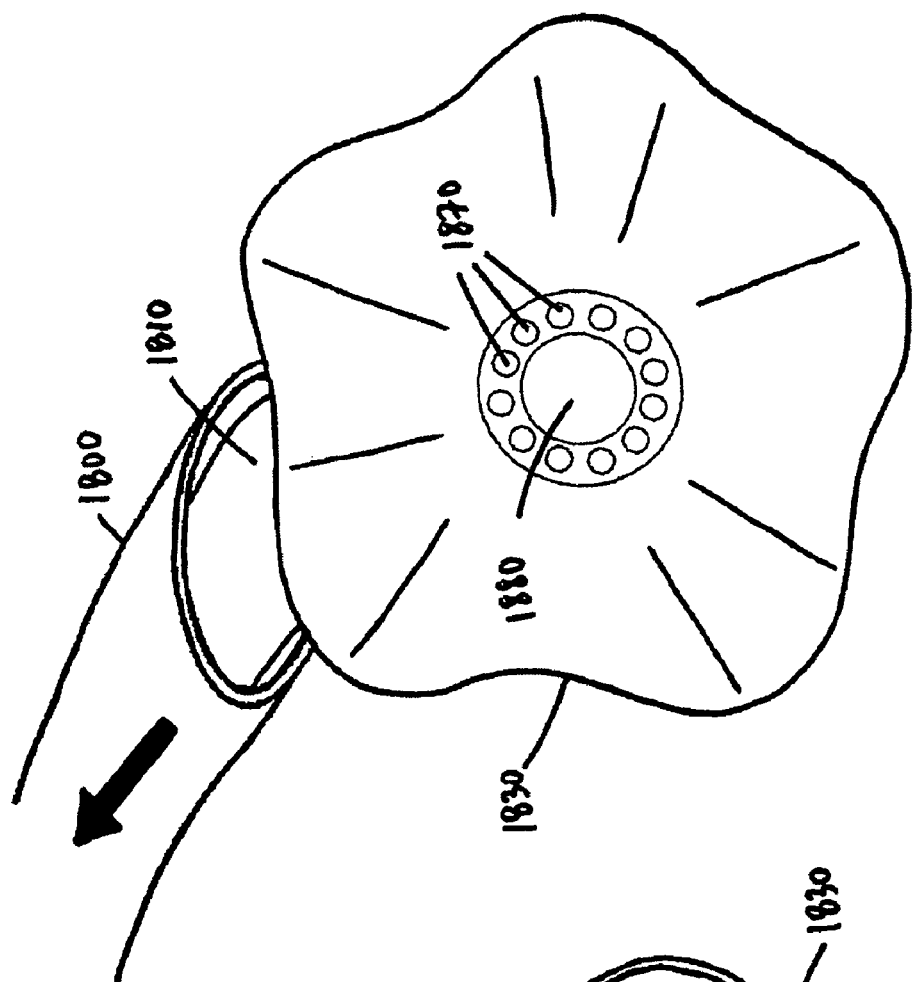
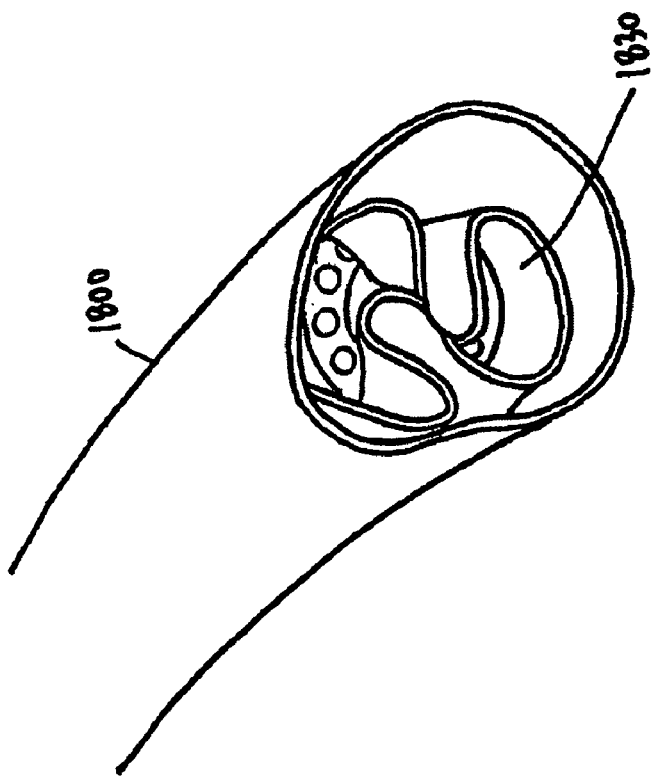
Fig. 18B
Fig. 18A

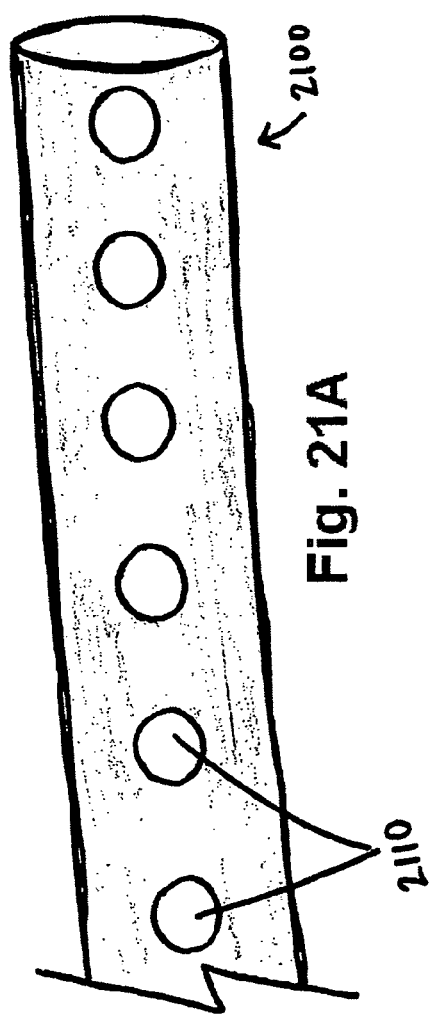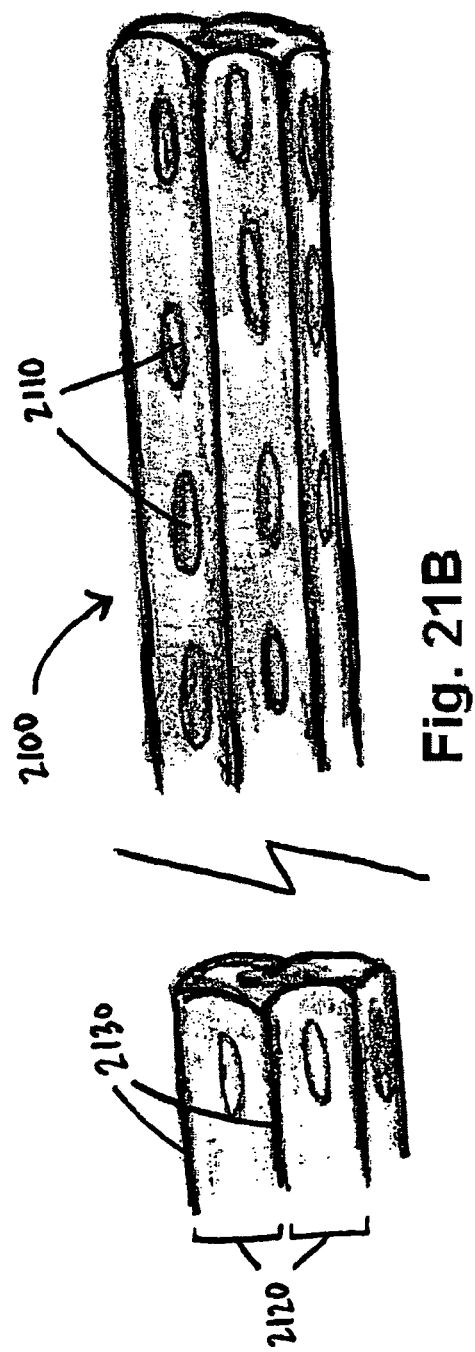
Fig. 21A
Fig. 21B

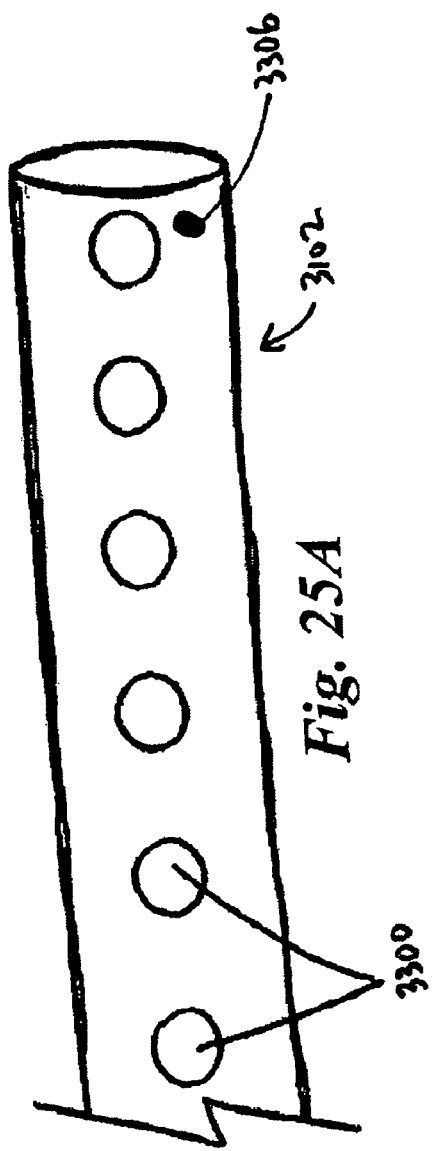
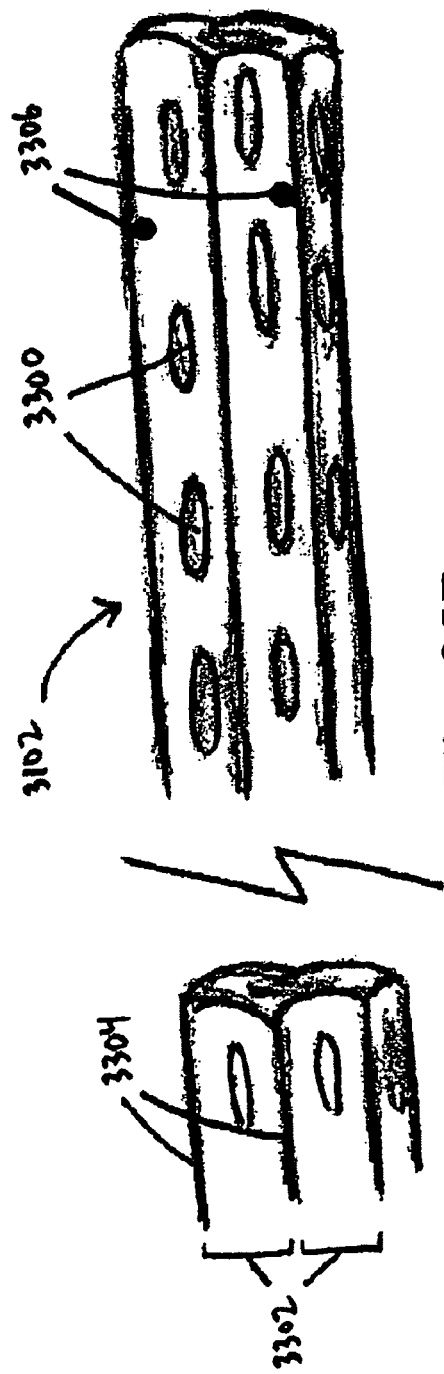
Fig. 25A
Fig. 25B

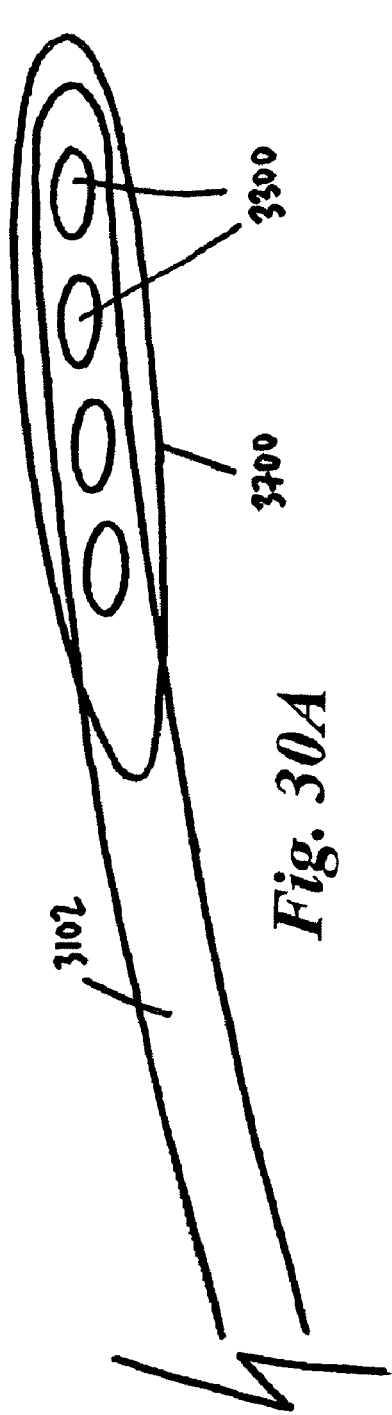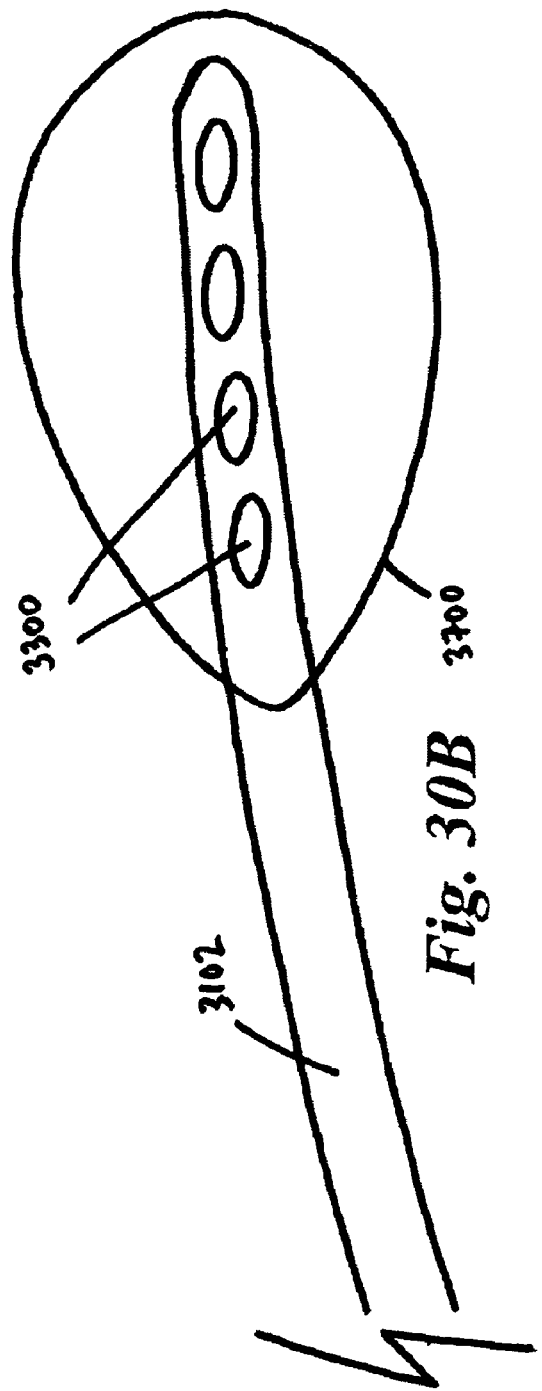

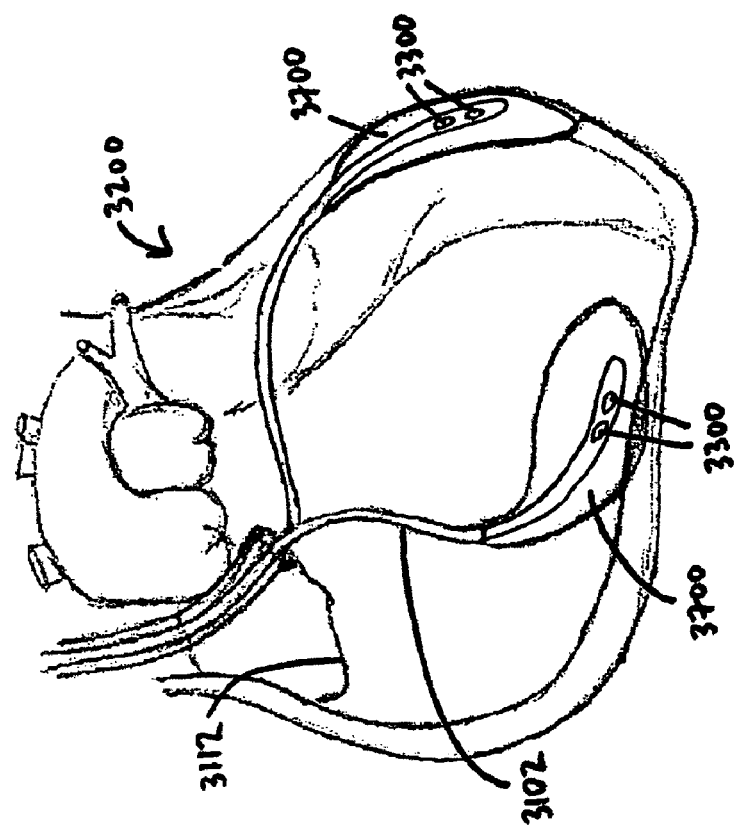
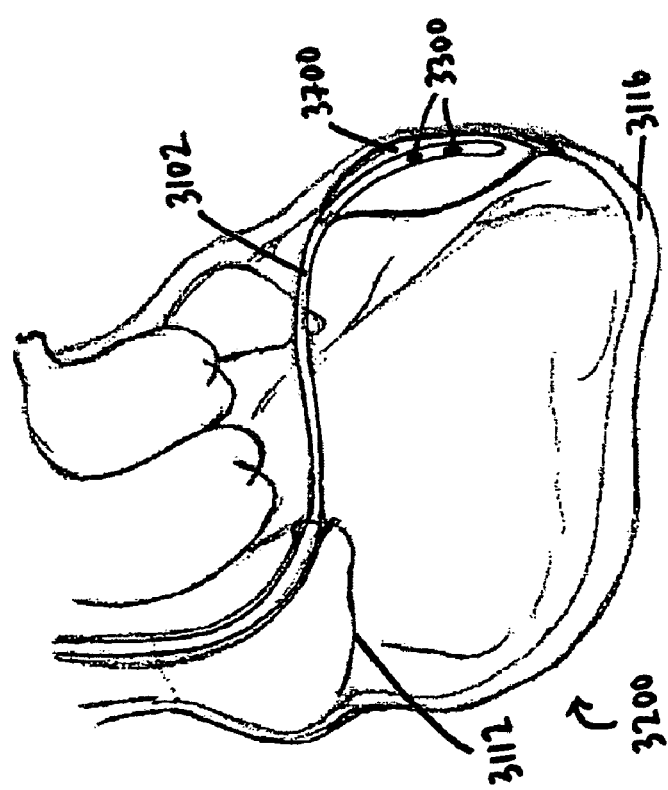
*Fig. 32B*
*Fig. 32A*

DEVICES, SYSTEMS, AND METHODS TO FACILITATE HEART FUNCTION

PRIORITY

The present application is related to, and claims the priority benefit of, International Patent Application Serial No. PCT/US2008/060870, filed Apr. 18, 2008, which is related to, claims the priority benefit of, and in at least some designated countries should be considered a continuation-in-part application of, International Patent Application Serial No. PCT/US2008/056666, filed Mar. 12, 2008, which is related to, claims the priority benefit of, and in at least some designated countries should be considered a continuation-in-part application of, International Patent Application Serial No. PCT/US2008/053061, filed Feb. 5, 2008, which is related to, claims the priority benefit of, and in at least some designated countries should be considered a continuation-in-part application of, International Patent Application No. PCT/US2007/015207, filed Jun. 29, 2007, which is related to, and claims the priority benefit of, U.S. Provisional Patent Application Ser. No. 60/914,452, filed Apr. 27, 2007, and U.S. Provisional Patent Application Ser. No. 60/817,421, filed Jun. 30, 2006. The present application also claims the priority benefit of International Patent Application Serial No. PCT/US2008/056666, filed Mar. 12, 2008, International Patent Application Serial No. PCT/US2008/053061, filed Feb. 5, 2008, International Patent Application No. PCT/US2007/015207, filed Jun. 29, 2007, and U.S. Provisional Patent Application Ser. No. 60/914,452, filed Apr. 27, 2007. The contents of each of these applications are hereby incorporated by reference in their entirety into this disclosure.

BACKGROUND

Ischemic heart disease, or coronary heart disease, kills more Americans per year than any other single cause. In 2004, one in every five deaths in the United States resulted from ischemic heart disease. Indeed, the disease has had a profound impact worldwide. If left untreated, ischemic heart disease can lead to chronic heart failure, which can be defined as a significant decrease in the heart's ability to pump blood. Chronic heart failure is often treated with drug therapy.

Ischemic heart disease is generally characterized by a diminished flow of blood to the myocardium and is also often treated using drug therapy. Although many of the available drugs may be administered systemically, local drug delivery ("LDD") directly to the heart can result in higher local drug concentrations with fewer systemic side effects, thereby leading to improved therapeutic outcomes.

Cardiac drugs may be delivered locally via catheter passing through the blood vessels to the inside of the heart. However, endoluminal drug delivery has several shortcomings, such as: (1) inconsistent delivery, (2) low efficiency of localization, and (3) relatively rapid washout into the circulation.

To overcome such shortcomings, drugs may be delivered directly into the pericardial space, which surrounds the external surface of the heart. The pericardial space is a cavity formed between the heart and the relatively stiff pericardial sac that encases the heart. Although the pericardial space is usually quite small because the pericardial sac and the heart are in such close contact, a catheter may be used to inject a drug into the pericardial space for local administration to the myocardial and coronary tissues. Drug delivery methods that supply the agent to the heart via the pericardial space offer several advantages over endoluminal delivery, including: (1) enhanced consistency and (2) prolonged exposure of the drug to the cardiac tissue.

In current practice, drugs are delivered into the pericardial space either by the percutaneous transventricular method or by the transthoracic approach. The percutaneous transventricular method involves the controlled penetration of a catheter through the ventricular myocardium to the pericardial space. The transthoracic approach involves accessing the pericardial space from outside the heart using a sheathed needle with a suction tip to grasp the pericardium, pulling it away from the myocardium to enlarge the pericardial space, and injecting the drug into the space with the needle.

For some patients with chronic heart failure, cardiac resynchronization therapy ("CRT") can be used in addition to drug therapy to improve heart function. Such patients generally have an abnormality in conduction that causes the right and left ventricles to beat (i.e., begin systole) at slightly different times, which further decreases the heart's already-limited function. CRT helps to correct this problem of dyssynchrony by resynchronizing the ventricles, thereby leading to improved heart function. The therapy involves the use of an implantable device that helps control the pacing of at least one of the ventricles through the placement of electrical leads onto specified areas of the heart. Small electrical signals are then delivered to the heart through the leads, causing the right and left ventricles to beat simultaneously.

Like the local delivery of drugs to the heart, the placement of CRT leads on the heart can be challenging, particularly when the target placement site is the left ventricle. Leads can be placed using a transvenous approach through the coronary sinus, by surgical placement at the epicardium, or by using an endocardial approach. Problems with these methods of lead placement can include placement at an improper location (including inadvertent placement at or near scar tissue, which does not respond to the electrical signals), dissection or perforation of the coronary sinus or cardiac vein during placement, extended fluoroscopic exposure (and the associated radiation risks) during placement, dislodgement of the lead after placement, and long and unpredictable times required for placement (ranging from about 30 minutes to several hours).

Clinically, the only approved non-surgical means for accessing the pericardial space include the subxiphoid and the ultrasound-guided apical and parasternal needle catheter techniques, and each methods involves a transthoracic approach. In the subxiphoid method, a sheathed needle with a suction tip is advanced from a subxiphoid position into the mediastinum under fluoroscopic guidance. The catheter is positioned onto the anterior outer surface of the pericardial sac, and the suction tip is used to grasp the pericardium and pull it away from the heart tissue, thereby creating additional clearance between the pericardial sac and the heart. The additional clearance tends to decrease the likelihood that the myocardium will be inadvertently punctured when the pericardial sac is pierced.

Although this technique works well in the normal heart, there are major limitations in diseased or dilated hearts—the very hearts for which drug delivery and CRT lead placement are most needed. When the heart is enlarged, the pericardial space is significantly smaller and the risk of puncturing the right ventricle or other cardiac structures is increased. Additionally, because the pericardium is a very stiff membrane, the suction on the pericardium provides little deformation of the pericardium and, therefore, very little clearance of the pericardium from the heart.

As referenced above, the heart is surrounded by a "sac" referred to as the pericardium. The space between the surface of the heart and the pericardium can normally only accommodate a small amount of fluid before the development of cardiac tamponade, defined as an emergency condition in which fluid accumulates in the pericardium. Therefore, it is not surprising that cardiac perforation can quickly result in tamponade, which can be lethal. With a gradually accumulating effusion, however, as is often the case in a number of diseases, very large effusions can be accommodated without tamponade. The key factor is that once the total intrapericardial volume has caused the pericardium to reach the noncompliant region of its pressure-volume relation, tamponade rapidly develops. Little W. C. and Freeman G. L. (2006). "Pericardial Disease." Circulation 113(12): 1622-1632.

Cardiac tamponade occurs when fluid accumulation in the intrapericardial space is sufficient to raise the pressure surrounding the heart to the point where cardiac filling is affected. Ultimately, compression of the heart by a pressurized pericardial effusion results in markedly elevated venous pressures and impaired cardiac output producing shock which, if untreated, it can be rapidly fatal. Id.

The frequency of the different causes of pericardial effusion varies depending in part upon geography and the patient population. Corey G. R. (2007). "Diagnosis and treatment of pericardial effusion." http://patients.uptodate.com. A higher incidence of pericardial effusion is associated with certain diseases. For example, twenty-one percent of cancer patients have metastases to the pericardium. The most common are lung (37% of malignant effusions), breast (22%), and leukemia/lymphoma (17%). Patients with HIV, with or without AIDS, are found to have increased prevalence, with 41-87% having asymptomatic effusion and 13% having moderate-to-severe effusion. Strimel W. J. et al. (2006). "Pericardial Effusion." http://www.emedicine.com/med/topic1786.htm.

End-stage renal disease is a major public health problem. In the United States, more than 350,000 patients are being treated with either hemodialysis or continuous ambulatory peritoneal dialysis. Venkat A. et al. (2006). "Care of the end-stage renal disease patient on dialysis in the ED." Am J Emerg Med 24(7): 847-58. Renal failure is a common cause of pericardial disease, producing large pericardial effusions in up to 20% of patients. Task Force members, Maisch B., Seferovic P. M., Ristic A. D., Erbel R., Rienmuller R., Adler Y., Tomkowski W. Z., Thiene G., Yacoub M. H., ESC Committee for Practice Guidelines, Priori S. G., Alonso Garcia M. A., Blanc J.-J., Budaj A., Cowie M., Dean V., Deckers J., Fernandez Burgos E., Lekakis J., Lindahl B., Mazzotta G., Moraies J., Oto A., Smiseth O. A., Document Reviewers, Acar J., Arbustini E., Becker A. E., Chiaranda G., Hasin Y., Jenni R., Klein W., Lang I., Luscher T. F., Pinto F. J., Shabetai R., Simoons M. L., Soler Soler J., Spodick D. H. (2004). "Guidelines on the Diagnosis and Management of Pericardial Diseases Executive Summary: The Task Force on the Diagnosis and Management of Pericardial Diseases of the European Society of Cardiology." Eur Heart J 25(7): 587-610.

Viral pericarditis is the most common infection of the pericardium. Inflammatory abnormalities are due to direct viral attack, the immune response (antiviral or anticardiac), or both. Id. Purulent (bacterial) pericarditis in adults is rare, but always fatal if untreated. Mortality rate in treated patients is 40%, mostly due to cardiac tamponade, toxicity, and constriction. It is usually a complication of an infection originating elsewhere in the body, arising by contiguous spread or haematogenous dissemination. Id. Other forms of pericarditis include tuberculous and neoplastic.

The most common secondary malignant tumors are lung cancer, breast cancer, malignant melanoma, lymphomas, and leukemias. Effusions may be small or large with an imminent tamponade. In almost two-thirds of the patients with documented malignancy pericardial effusion is caused by non-malignant diseases, e.g., radiation pericarditis, or opportunistic infections. The analyses of pericardial fluid, pericardial or epicardial biopsy are essential for the confirmation of malignant pericardial disease. Id.

Management of pericardial effusions continues to be a challenge. There is no uniform consensus regarding the best way to treat this difficult clinical entity. Approximately half the patients with pericardial effusions present with symptoms of cardiac tamponade. In these cases, symptoms are relieved by pericardial decompression, irrespective of the underlying cause. Georghiou G. P. et al. (2005). "Video-Assisted Thoracoscopic Pericardial Window for Diagnosis and Management of Pericardial Effusions." Ann Thorac Surg 80(2): 607-610. Symptomatic pericardiac effusions are common and may result from a variety of causes. When medical treatment has failed to control the effusion or a diagnosis is needed, surgical intervention is required. Id.

The most effective management of pericardial effusions has yet to be identified. The conventional procedure is a surgically placed pericardial window under general anesthesia. This procedure portends significant operative and anesthetic risks because these patients often have multiple comorbidities. Less invasive techniques such as blind needle pericardiocentesis have high complication and recurrence rates. The technique of echocardiographic-guided pericardiocentesis with extended catheter drainage is performed under local anesthetic with intravenous sedation. Creating a pericardiostomy with a catheter in place allows for extended drainage and sclerotherapy. Echocardiographic-guided pericardiocentesis has been shown to be a safe and successful procedure when performed at university-affiliated or academic institutions. However, practices in community hospitals have rarely been studied in detail. Buchanan C. L. et al. (2003). "Pericardiocentesis with extended catheter drainage: an effective therapy." Ann. Thorac. Surg. 76(3): 817-82.

The treatment of cardiac tamponade is drainage of the pericardial effusion. Medical management is usually ineffective and should be used only while arrangements are made for pericardial drainage. Fluid resuscitation may be of transient benefit if the patient is volume depleted (hypovolemic cardiac tamponade).

Surgical drainage (or pericardiectomy) is excessive for many patients. The best option is pericardiocentesis with the Seldinger technique, leaving a pigtail drainage catheter that should be kept in place until drainage is complete. Sagrista Sauleda J. et al. (2005). "[Diagnosis and management of acute pericardial syndromes]." Rev Esp Cardiol 58(7): 830-41. This less-invasive technique resulted in a short operative time and decreased supply, surgeon, and anesthetic costs. When comparing procedure costs of a pericardial window versus an echo-guided pericardiocentesis with catheter drainage at our institution, there was a cost savings of approximately $1,800/case in favor of catheter drainage. In an era of accelerating medical costs, these savings are of considerable importance. Buchanan C. L. et al., 2003.

Currently, 0.2% of the U.S. population over 45 years of age (nearly 200,000 patients) have reached a stage of severe congestive heart failure (CHF) at which medical therapy is not sufficient to sustain an acceptable level of cardiac function. Since only approximately 2,000 donor hearts are available in the U.S. each year for transplantation, it is necessary to have cardiac support or replacement. Baughman K. L. and Jarcho J. A. (2007). "Bridge to Life—Cardiac Mechanical Support." N. Engl. J. Med. 357(9): 846-849.

Although there has been important progress in pharmacological treatments for CHF, such as Angiotensin-Converting Enzyme (ACE) inhibitors, beta-blockers, and aldosterone inhibitors that have significantly decreased mortality, the progression from asymptomatic left ventricular dysfunction to symptomatic CHF is still a major issue. Mancini D. and Burkhoff D. (2005). "Mechanical Device-Based Methods of Managing and Treating Heart Failure." Circulation 112(3): 438-448.

The purpose of many heart failure treatments is to slow, or reverse, the process. Several studies have demonstrated that a pharmacological blockade of the key neurohormonal pathways interrupts the vicious cycle, retards progression, and improves survival. Nevertheless, studies suggest that attempts to block additional neurohormonal pathways may be detrimental. These findings underscore the limit of pharmacological treatments for heart failure. Id.

Regarding devices for treatment of CHF, there have been extensive efforts to develop and test device-based therapies for patients with both acute and chronic heart failure. For example, cardiac resynchronization therapy (CRT), myogenesis (e.g., stem cells and myoblasts) and electrical therapies, such as less invasive defibrillators, are under active investigation. Surgical reshaping of the dilated heart, including a reduction in the radius of curvature, can decrease wall stress, in principle allowing for reverse remodeling. Removal of dyskinetic scar is clinically accepted and reported to be associated with satisfactory outcomes. The effects of removing akinetic scar (often referred to as the Dor procedure or surgical anterior ventricular restoration (SAVR) are also under investigation. Another method proposed to decrease wall stress and to induce reverse remodeling is by passive ventricular restraint devices. This concept evolved from an earlier investigational approach called cardiomyoplasty. Id.

In order to treat symptoms of heart failure due to mitral insufficiency, numerous catheter-based devices are being developed to perform mitral valve repair percutaneously to reduce risk as a non-invasive procedure. Id.

For over 40 years, many researchers have pursued the development of mechanical cardiac support. The earliest forms of clinical use were introduced in 1953 by the cardiopulmonary bypass, and was used for cardiopulmonary support during cardiac surgery. In 1962, the intra-aortic balloon counterpulsation was introduced and used for temporary partial hemodynamic support improving myocardial contractility and coronary perfusion. Neither approach provides full cardiac replacement, however, even temporarily, as each approach is limited by the invasive nature of the procedure, e.g. the requirement for large-bore cannulation of the femoral circulation limits the patient's mobility and restricts functional recovery. Risks of bleeding, thromboembolism, and infection also limit the feasible duration of support. Baughman and Jarcho, 2007.

The intra-aortic balloon pump (IABP) is the most widely used of all circulatory assist devices. Counterpulsation improves left ventricular (LV) performance by enhancing myocardial oxygen balance. It increases myocardial oxygen supply by diastolic augmentation of coronary perfusion and decreases myocardial oxygen requirements through a reduction in the afterload component of cardiac work. Azevedo C. F. et al. (2005). "The effect of intra-aortic balloon counterpulsation on left ventricular functional recovery early after acute myocardial infarction: a randomized experimental magnetic resonance imaging study." Eur. Heart J. 26(12): 1235-1241.

Support for the use of IABP in patients with acute myocardial infarction (AMI) has been based on the above theoretical consideration. However, the relationship between the beneficial physiological effect of counterpulsation and post-AMI LV functional recovery remains largely undefined. In fact, several studies have investigated the immediate effect of IABP on LV performance and demonstrated that, during counterpulsation, there is a significant improvement in LV haemodynamics.

An important difference exists between the improved haemodynamics provided by counterpulsation itself and the possible favorable effect on post-AMI non-assisted LV contractility. Id. Furthermore, it is important to highlight that at twenty-four hours after reperfusion, the degree of functional recovery was similar with or without IABP counterpulsation. Therefore, even though IABP counterpulsation may have an important role in supporting and improving the clinical status of patients in the early phases of reperfused AMI, it does not seem to have a significant beneficial effect in terms of long-term LV functional improvement. Id.

The available forms of mechanical cardiac support are devices known as pumps that can be classified into three types: centrifugal pumps, volume-displacement pumps, and axial-flow pumps. Moreover, three distinct clinical indications for mechanical cardiac support have been defined. Temporary support is instituted when recovery of native heart function is expected. Among patients who are candidates for heart transplantation but who may not survive the waiting period for a transplant, a ventricular assist device may be used as a "bridge to transplantation." Ultimately, for patients who are not candidates for heart transplant and for whom recovery of cardiac function is not probable, a mechanical device may be utilized as "destination therapy"; i.e., as a permanent replacement for the native heart. This last indication has only recently been established in clinical practice but is expected to be of growing importance in the future. Baughman and Jarcho, 2007.

Despite the wide variety of pumps currently available, the problems associated with this technology have not changed since the early years of development. Id. Available devices for circulatory support use numerous blood contacting pumps to assist the failing heart. Blood removed from the venous circulation is injected into the arterial circuit in order to increase organ perfusion. Unfortunately, blood contact remains the core for major complications generally associated with mechanical circulatory support. Thromboembolic events, the need for anticoagulation, bleeding, hemolysis, immune suppression, and activation of the inflammatory system are factors which continue to threaten those requiring this therapy. Moreover, device implantation can be difficult and time-consuming which limits feasibility when cardiovascular collapse occurs suddenly. These unsolved problems provide continued motivation to develop non-blood contacting circulatory support devices. Instead of unloading the heart, mechanical forces are directed toward increasing pump performance of the ventricular wall. Anstadt M. P. et al. (2002). "Non-blood contacting biventricular support for severe heart failure." Ann. Thorac. Surg. 73(2): 556-562. These complex problems may be circumvented by a fundamentally different approach to cardiac assist.

Among all organs, the heart is unique in that oxygen extraction is nearly close to maximal. Thus, the only way that this metabolically demanding organ can increase oxygen consumption is by increasing coronary blood flow. In this aspect of oxygen delivery, the heart is also unique because most flow occurs in diastole instead of in systole. Carabello B. A. (2006). "Understanding Coronary Blood Flow: The Wave of the Future." Circulation 113(14): 1721-1722." The compression of the vasculature by the surrounding cardiac muscle during systole impedes flow so that while the pressure head for flow is maximum in systole, flow is maximum in diastole.

Waves are generated from both ends of the coronary vasculature, in that proximal waves move forward and distal waves move backward. In this scheme, proximal "pushing" waves and distal "suction" waves accelerate forward blood flow, while proximal suction waves and distal pushing waves do the converse. Carabello, B. A., 2006. The forward-moving pushing wave is generated by systolic pressure. It drives blood primarily into the epicardial coronaries where it may be stored until it is released for forward flow when the myocardium relaxes. The second important wave, typically the largest, is a suction wave generated by relaxation of the left ventricle and is likely the main driver in diastolic coronary blood flow. Id.

Among patients with ischemic heart disease, it is of great importance to improve the microvascular blood flow in the myocardium to protect the myocardium from infarction. Today, many different drugs and sophisticated techniques, such as percutaneous coronary intervention (PCI) and coronary artery bypass graft (CABG), are used with remarkable results. Despite this, there is a large group of patients who have been heavily treated with different drugs (leading to drug-resistant angina pectoris) who have already undergone one or more PCIs or CABG, or both, and who still have serious ischemic heart disease. A satisfactory mode of treatment for these patients has yet to be found. Lindstedt S. et al. (2007). "Blood Flow Changes in Normal and Ischemic Myocardium During Topically Applied Negative Pressure." Ann. Thorac. Surg. 84(2): 568-573.

Despite the extensive clinical use and excellent outcome of topical negative pressure (TNP) in wound therapy, the fundamental scientific mechanism is, to a large extent, unknown. One of the known effects of TNP is enhanced blood flow to the wound edge, as has been shown in a sternotomy wound model. TNP increases blood flow velocity and opens up the capillary beds. Mechanical forces exerted by TNP and increased blood flow affect the cytoskeleton in the vascular cells and stimulate granulation tissue formation, which involves endothelial proliferation, capillary budding, and angiogenesis. Id.

As described herein, studies have shown that when myocardium was exposed to a topical negative pressure of −50 mm Hg, an immediate significant increase in microvascular blood flow was observed. To investigate whether similar results could be obtained in an ischemic model, the LAD was occluded for 20 minutes. When the ischemic area of the myocardium was exposed to a topical negative pressure of −50 mm Hg, an immediate significant increase in microvascular blood flow was detected. Furthermore, after 20 minutes of reperfusion, myocardial blood flow significantly increased when −50 mm Hg was applied. Lindstedt S. et al. (2007). Similar findings have been made with TNP of −25 mmHg.

TNP stimulation of myocardial blood flow may be a possible therapeutic intervention. It is believed that the sheering forces exerted by TNP stimulate angiogenesis. It has been observed in patients treated with TNP that richly vascularized granulation tissue develops over the heart within 4 to 5 days. These newly formed blood vessels may provide collateral blood supply that is needed when the native circulation fails to provide sufficient blood flow. It may be that the TNP stimulation of blood flow and development of collateral blood vessels in part accounts for the reduced long-term mortality in patients treated with TNP for poststernotomy mediastinitis after CABG. Lindstedt S. et al. (2007).

The pericardium is a conical fibro-serous sac, in which the heart and the roots of the great vessels are contained. The heart is placed behind the sternum and the cartilages of the third to seventh ribs of the left side, in the mediastinal cavity. Gray H. (1918). "Anatomy of the Human Body." Philadelphia: Lea & Febiger; Bartleby.com, 2000, pp. 1821-1865. The pericardium is separated from the anterior wall of the thorax, in the greater part of its extent, by the lungs and pleurae. However, a small area, somewhat variable in size and usually corresponding with the left half of the lower portion of the body of the sternum and the medial ends of the cartilages of the fourth and fifth ribs of the left side, comes into direct relationship with the chest wall. Behind, the pericardial sac rests upon the bronchi, the esophagus, the descending thoracic aorta, and the posterior part of the mediastinal surface of each lung. Laterally, it is covered by the pleurae, and is in relation with the mediastinal surfaces of the lungs. The phrenic nerve, with its accompanying vessels, descends between the pericardium and pleura on either side. Id.

Similar to synovial joints in which moving surfaces may be separated by a thin fluid film at different stages of stance and walking, the heart and pericardium might be viewed as a load-bearing system in which deformable epicardial and pericardial sliding surfaces are separated by a lubricant. deVries G. et al. (2001). "A novel technique for measurement of pericardial pressure." Am. J. Physiol. Heart Circ. Physiol. 280(6): H2815-22.

The role played by the pericardium in cardiac hemodynamics is important. Almost a century ago, Barnard concluded that the pericardium can be a significant constraint in filling of the heart. Barnard H. (1898). "The functions of the pericardium." J. Physiol. 22: 43-47. In a simple experiment, he isolated and inflated the pericardium of a dog with a bicycle pump and observed that it did not rupture until pressures of 950 to 1330 mm Hg. According to Barnard, "when a relaxed heart is subject to a venous pressure of from 10 to 20 mm Hg, the pericardium takes the strain and prevents dilatation of the heart beyond a certain point. Thus the mechanical disadvantages of dilated cavities and of a thinned wall are prevented." Hamilton D. R. et al. (1994). "Right atrial and right ventricular transmural pressures in dogs and humans. Effects of the pericardium." Circulation 90(5): 2492-500.

Gibbons Kroeker et al. showed that direct interaction between the left ventricle (LV) and right ventricle (RV) is mediated by the pericardium, as shown by a pericardium-mediated compensation for sudden changes in atrial volume. Gibbons Kroeker et al. (2006). "A 2D FE model of the heart demonstrates the role of the pericardium in ventricular deformation." Am. J. Physiol. Heart. Circ. Physiol. 291(5): H2229-36. At low strains, the pericardium is extremely distensible, but when strains are greater than ten percent, the pericardium becomes very stiff. Consequently, over a range of lower heart volumes, the pericardium will expand easily with the heart as it fills. At some point, however, it will stiffen and become an ever tighter ring around the minor axis of the heart, resisting further expansion. Id.

Local contact forces between the pericardium and the heart cause regional variation in pericardial deformation during the cardiac cycle, reflecting volume changes of the underlying cardiac chambers. Goto Y. and LeWinter M. M. (1990). "Non-uniform regional deformation of the pericardium during the cardiac cycle in dogs." Circ. Res. 67(5): 1107-14. The measured left ventricular diastolic pressure is equal to the sum of the pressure differences across the myocardium and the pericardium. Thus, increases in pericardial pressure raise measured ventricular diastolic pressure without change in ventricular volume which causes an upward shift in the pressure-volume curve. Tyberg J. V. et al. (1978). "A mechanism for shifts in the diastolic, left ventricular, pressure-volume curve: the role of the pericardium." Eur. J. Cardiol. 7 Suppl: 163-75.

Noble gases, also known as the helium family or the neon family, are the elements in group 18 of the periodic table. Noble gases rarely react with other elements since they are already stable. Under normal conditions, they are odorless, colorless, monatomic gases, each having its melting and boiling points close together so that only a small temperature range exists for each noble gas in which it is a liquid. Noble gases have numerous important applications in lighting, welding and space technology. The seven noble gasses are: helium, neon, argon, krypton, xenon, radon, and ununoctium.

Helium (He) is a colorless, odorless, tasteless, non-toxic, inert monatomic chemical element that heads the noble gas series in the periodic table and whose atomic number is 2. The boiling and melting points are the lowest among the elements and it exists only as a gas except in extreme conditions. Helium is less water soluble than any other gas known, and it does not have any measurable viscosity because the speed of sound in helium is nearly three times the speed of sound in air.

Neutral helium at standard conditions is non-toxic, plays no biological role, and is found in trace amounts in human blood. The addition of helium to a gas mixture prevents the occurrence of ventricular fibrillation. Helium has a definite protective effect against ventricular fibrillation when this preparation is used. The mechanism of the protective effect remains to be established. It is believed that helium may increase collateral circulation in the ischemic area. Pifarre R. et al. (1969). "Helium in the Prevention of Ventricular Fibrillation." Chest 56(2): 135-138.

Clearly, there is a clinical need for a safe and effective approach to treat patients with congestive heart failure.

BRIEF SUMMARY

Disclosed herein are devices, systems, and methods for assisting heart function. In addition, various disclosed embodiments provide devices, systems, and methods for injecting and removing a gas from a pericardial space.

According to at least one embodiment of a device for assisting heart function, the device comprises at least two electromagnetic plates, the at least two electromagnetic plates having an inner surface, a cardiac processor electrically coupled to at least one of the at least two electromagnetic plates, a bladder having an inner chamber, the bladder attached to an inner surface of at least one of the at least two electromagnetic plates, a source of gas in communication with the inner chamber of the bladder, and a catheter having a proximal end and a distal end and having a lumen therethrough, the catheter defining at least one aperture positioned therethrough at or near the distal end of the catheter, the proximal end of the catheter in communication with the inner chamber of the bladder, wherein when the distal end of the catheter is positioned within a pericardial space, the device operates to inject gas into and/or remove gas from the pericardial space. In another embodiment, the at least two electromagnetic plates are operable to compress the bladder, wherein the compression of the bladder, when the distal end of the catheter is positioned within a pericardial space, injects gas into the pericardial space. In yet another embodiment, the at least two electromagnetic plates are operable to compress the bladder, and wherein the compression is facilitated using one or more actuators operably coupled to the one or more electromagnetic plates. In an additional embodiment, the at least two electromagnetic plates are operable to expand the bladder, wherein the expansion of the bladder, when the distal end of the catheter is positioned within a pericardial space, removes gas from the pericardial space. In yet an additional embodiment, the at least two electromagnetic plates are operable to expand the bladder, and wherein the expansion is facilitated using one or more actuators operably coupled to the one or more electromagnetic plates.

According to at least one embodiment of a device for assisting heart function, the cardiac processor is operable to cause the at least two electromagnetic plates to compress and/or expand the bladder. In another embodiment, the cardiac processor comprises heart data, the heart data comprising at least one parameter, and wherein the cardiac processor is operable to cause the at least two electromagnetic plates to compress and/or expand the bladder based upon the at least one parameter of the heart data. In yet another embodiment, the device further comprises at least one pressure/volume sensor operably coupled to the catheter, wherein the at least one pressure/volume sensor operates to provide pressure and/or volume data to the cardiac processor, the pressure and/or volume data relating to the pressure and/or volume of gas detected at the at least one pressure/volume sensor. In an additional embodiment, the cardiac processor is operable to cause the at least two electromagnetic plates to compress and/or expand the bladder based upon pressure and/or volume data. In yet an additional embodiment, the cardiac processor is coupled to the at least two electromagnetic plates using at least one wire.

According to at least one embodiment of a device for assisting heart function, the bladder comprises a polyurethane bladder. In another embodiment, the source of gas comprises a portable gas reservoir. In yet another embodiment, the gas is a noble gas. In an additional embodiment, the noble gas is helium. In yet an additional embodiment, gas enters the pericardial space from the bladder, through the lumen of the catheter, and out from the at least one aperture defined within the catheter.

According to at least one embodiment of a device for assisting heart function, gas is removed from the pericardial space through the at least one aperture defined within the catheter, through the lumen of the catheter, and into the bladder. In another embodiment, the device further comprises a valve positioned between the source of gas and the bladder. In yet another embodiment, the valve is a unilateral valve operable to allow gas to flow from the source of gas. In an additional embodiment, the device further comprises a power supply operably coupled to the cardiac processor. In yet an additional embodiment, the device further comprises a power supply operably coupled to the at least two electromagnetic plates.

According to at least one embodiment of a device for assisting heart function, the device further comprises a power supply operably coupled to one or more actuators operably coupled to the one or more electromagnetic plates. In another embodiment, the power supply comprises a battery. In yet another embodiment, the battery comprises a rechargeable battery. In an additional embodiment, the device further comprise a data storage device in communication with the cardiac processor, wherein the cardiac processor is operable to cause the at least two electromagnetic plates to compress and/or expand the bladder based upon data stored within the data storage device. In yet an additional embodiment, the cardiac processor is operable to increase a frequency of compression of the bladder from a first compression rate to a second compression rate, wherein the increase in frequency causes a heart to beat at a faster rate.

According to at least one embodiment of a device for assisting heart function, the cardiac processor is operable to decrease a frequency of compression of the bladder from a first compression rate to a second compression rate, wherein the decrease in frequency causes a heart to beat at a slower rate. In another embodiment, at least a portion of the device is positioned externally to a patient's body, and wherein at least a portion of the device is positioned within a patient's body. In yet another embodiment, the source of gas is positioned externally to the patient's body. In an additional embodiment, the cardiac processor is positioned within the patient's body. In yet an additional embodiment, the device further comprises at least one belt coupled to the source of gas, wherein the at least one belt may be secured externally to the patient's body to secure the source of gas to the patient's body.

According to at least one embodiment of a device for assisting heart function, the at least one balloon is coupled to the catheter and positioned externally to the catheter. In another embodiment, the device further comprises a conduit having a proximal end and a distal end, the distal end of the conduit coupled to the at least one balloon, wherein when the catheter is positioned within an aperture in an atrial wall and when the at least one balloon is positioned at or near the aperture in the atrial wall, inflation of the at least one balloon causes the catheter to be held in place at the atrial wall. In yet another embodiment, the catheter is a suction/infusion catheter. In an additional embodiment, the inflation of the at least one balloon causes a first portion of the at least one balloon to inflate on a first side of the atrial wall, and further causes a second portion of the at least one balloon to inflate on a second side of the atrial wall, securing the catheter in place at the atrial wall. In yet an additional embodiment, the at least one balloon comprises a first balloon and a second balloon.

According to at least one embodiment of a device for assisting heart function, when the catheter is positioned within an aperture of an atrial wall, wherein the first balloon is positioned on a first side of the atrial wall and wherein the second balloon is positioned on a second side of the atrial wall, the catheter is held in place at the atrial wall when the first balloon and the second balloon are inflated. In another embodiment, the proximal end of the conduit is coupled to a suction/infusion source, and wherein at least one balloon is inflated using by the suction/infusion source. In yet another embodiment, the device further comprises a physical structure coupled to the catheter and positioned externally to the catheter, wherein the physical structure is positioned at or near the at least one balloon. In an additional embodiment, the catheter is positioned within an aperture of an atrial wall and wherein the at least one balloon is positioned on one side of the atrial wall and the physical structure is positioned on the other side of the atrial, the catheter is held in place at the atrial wall when the at least one balloon is inflated. In yet an additional embodiment, the physical structure comprises a protrusion.

According to at least one embodiment of an apparatus for securing a catheter within a heart, the apparatus comprises a catheter having a proximal end and a distal end and at least one lumen defined therethrough, the catheter defining at least one aperture positioned therethrough at or near the distal end of the catheter, at least one balloon coupled to the catheter and positioned externally to the catheter, a conduit having a proximal end and a distal end, the distal end of the conduit coupled to the at least one balloon, wherein when the catheter is positioned within an aperture in an atrial wall and when the at least one balloon is positioned at or near the aperture in the atrial wall, inflation of the at least one balloon causes the catheter to be held in place at the atrial wall. In another embodiment, the catheter is a suction/infusion catheter. In yet another embodiment, inflation of the at least one balloon causes a first portion of the at least one balloon to inflate on a first side of the atrial wall, and further causes a second portion of the at least one balloon to inflate on a second side of the atrial wall, securing the catheter in place at the atrial wall. In an additional embodiment, the at least one balloon comprises a first balloon and a second balloon. In yet an additional embodiment, the first balloon is positioned on a first side of the atrial wall and wherein the second balloon is positioned on a second side of the atrial wall, the catheter is held in place at the atrial wall when the first balloon and the second balloon are inflated.

According to at least one embodiment of an apparatus for securing a catheter within a heart, the proximal end of the conduit is coupled to a suction/infusion source, and the at least one balloon is inflated using the suction/infusion source. In another embodiment, the apparatus further comprises a physical structure coupled to the catheter and positioned externally to the catheter, wherein the physical structure is positioned at or near the at least one balloon. In yet another embodiment, when the catheter is positioned within the aperture of the atrial wall and wherein the at least one balloon is positioned on one side of the atrial wall and the physical structure is positioned on the other side of the atrial wall, the catheter is held in place at the atrial wall when the at least one balloon is inflated. In an additional embodiment, the physical structure comprises a protrusion.

According to at least one embodiment of a method of assisting heart function, the method comprises the steps of providing a device for assisting heart function, comprising at least two electromagnetic plates, the at least two electromagnetic plates having an inner surface, a cardiac processor electrically coupled to at least one of the at least two electromagnetic plates, a bladder having an inner chamber, the bladder attached to an inner surface of at least one of the at least two electromagnetic plates, a source of gas in communication with the inner chamber of the bladder, and a catheter having a proximal end and a distal end and having a lumen therethrough, the catheter defining at least one aperture positioned therethrough at or near the distal end of the catheter, the proximal end of the catheter in communication with the inner chamber of the bladder, and operating the device to inject gas into and/or remove gas from the pericardial space to assist heart function. In another embodiment, the at least two electromagnetic plates are operable to compress the bladder, wherein the compression of the bladder, when the distal end of the catheter is positioned within a pericardial space, injects gas into the pericardial space. In yet another embodiment, the at least two electromagnetic plates are operable to compress the bladder, and wherein the compression is facilitated using one or more actuators operably coupled to the one or more electromagnetic plates. In an additional embodiment, the at least two electromagnetic plates are operable to expand the bladder, wherein the expansion of the bladder, when the distal end of the catheter is positioned within a pericardial space, removes gas from the pericardial space. In yet an additional embodiment, the at least two electromagnetic plates are operable to expand the bladder, and wherein the expansion is facilitated using one or more actuators operably coupled to the one or more electromagnetic plates.

According to at least one embodiment of a method of assisting heart function, the cardiac processor is operable to cause the at least two electromagnetic plates to compress and/or expand the bladder. In another embodiment, the cardiac processor comprises heart data, the heart data comprising at least one parameter, and wherein the cardiac processor is operable to cause the at least two electromagnetic plates to compress and/or expand the bladder based upon the at least one parameter of the heart data. In yet another embodiment, the catheter further comprises at least one pressure/volume sensor operably coupled to the catheter, wherein the at least one pressure/volume sensor operates to provide pressure and/or volume data to the cardiac processor, the pressure and/or volume data relating to the pressure and/or volume of gas detected at the at least one pressure/volume sensor. In an additional embodiment, the cardiac processor is operable to cause the at least two electromagnetic plates to compress and/or expand the bladder based upon pressure and/or volume data. In yet an additional embodiment, the cardiac processor is coupled to the at least two electromagnetic plates using at least one wire.

According to at least one embodiment of a method of assisting heart function, the bladder comprises a polyurethane bladder. In another embodiment, the bladder comprises a silastic bladder. In yet another embodiment, the source of gas comprises a portable gas reservoir. In an additional embodiment, the gas is a noble gas. In yet an additional embodiment, the noble gas is helium.

According to at least one embodiment of a method of assisting heart function, gas enters the pericardial space from the bladder, through the lumen of the catheter, and out from the at least one aperture defined within the catheter. In another embodiment, gas is removed from the pericardial space through the at least one aperture defined within the catheter, through the lumen of the catheter, and into the bladder. In yet another embodiment, the device further comprises a valve positioned between the source of gas and the bladder. In an additional embodiment, the valve is a unilateral valve operable to allow gas to flow from the source of gas. In yet an additional embodiment, the device further comprises a power supply operably coupled to the cardiac processor.

According to at least one embodiment of a method of assisting heart function, the device further comprises a power supply operably coupled to the at least two electromagnetic plates. In another embodiment, the device further comprises a power supply operably coupled to one or more actuators operably coupled to the one or more electromagnetic plates. In yet another embodiment, the power supply comprises a battery. In an additional embodiment, the battery comprises a rechargeable battery. In yet an additional embodiment, the device further comprises a data storage device in communication with the cardiac processor, wherein the cardiac processor is operable to cause the at least two electromagnetic plates to compress and/or expand the bladder based upon data stored within the data storage device.

According to at least one embodiment of a method of assisting heart function, the cardiac processor is operable to increase a frequency of compression of the bladder from a first compression rate to a second compression rate, wherein the increase in frequency causes a heart to beat at a faster rate. In another embodiment, the cardiac processor is operable to decrease a frequency of compression of the bladder from a first compression rate to a second compression rate, wherein the decrease in frequency causes a heart to beat at a slower rate. In yet another embodiment, at least a portion of the device is positioned externally to a patient's body, and wherein at least a portion of the device is positioned within a patient's body. In an additional embodiment, the source of gas is positioned externally to the patient's body. In yet an additional embodiment, the cardiac processor is positioned within the patient's body.

According to at least one embodiment of a method of assisting heart function, the device further comprises at least one belt coupled to the source of gas, wherein the at least one belt may be secured externally to the patient's body to secure the source of gas to the patient's body. In another embodiment, at least one balloon is coupled to the catheter and positioned externally to the catheter. In yet another embodiment, the device further comprises a conduit having a proximal end and a distal end, the distal end of the conduit coupled to the at least one balloon, wherein inflation of the at least one balloon, when the catheter is positioned within an aperture of an atrial wall wherein the at least one balloon is positioned at or near the aperture, causes the catheter to be held in place at the atrial wall. In an additional embodiment, the catheter is a suction/infusion catheter. In yet an additional embodiment, the inflation of the at least one balloon causes a first portion of the at least one balloon to inflate on a first side of the atrial wall, and further causes a second portion of the at least one balloon to inflate on a second side of the atrial wall, securing the catheter in place at the atrial wall.

According to at least one embodiment of a method of assisting heart function, the at least one balloon comprises a first balloon and a second balloon. In another embodiment, the first balloon is positioned on a first side of the atrial wall and wherein the second balloon is positioned on a second side of the atrial wall, the catheter is held in place at the atrial wall when the first balloon and the second balloon are inflated. In yet another embodiment, the proximal end of the conduit is coupled to a suction/infusion source, and wherein at least one balloon is inflated using the suction/infusion source. In an additional embodiment, the catheter further comprises a physical structure coupled to the catheter and positioned externally to the catheter, wherein the physical structure is positioned at or near the at least one balloon. In yet an additional embodiment, when the catheter is positioned within the aperture of the atrial wall and wherein the at least one balloon is positioned on one side of the atrial wall and the physical structure is positioned on the other side of the atrial wall, the catheter is held in place at the atrial wall when the at least one balloon is inflated. In another embodiment, the physical structure comprises a protrusion.

According to at least one embodiment of a method for securing a catheter within a heart, the method comprises the steps of introducing a catheter through an aperture of an atrial wall, the catheter comprising a proximal end and a distal end and at least one lumen defined therethrough, the catheter defining at least one aperture positioned therethrough at or near the distal end of the catheter, at least one balloon coupled to the catheter and positioned externally to the catheter, a conduit having a proximal end and a distal end, the distal end of the conduit coupled to the at least one balloon, positioning the catheter so that the at least one balloon is positioned at or near the aperture of the atrial wall, inflating the at least one balloon to secure the catheter in place at the atrial wall. In another embodiment, the catheter is a suction/infusion catheter. In yet another embodiment, the step of inflating the at least one balloon causes a first portion of the at least one balloon to inflate on a first side of the atrial wall, and further causes a second portion of the at least one balloon to inflate on a second side of the atrial wall, securing the catheter in place at the atrial wall. In an additional embodiment, the at least one balloon comprises a first balloon and a second balloon. In yet an additional embodiment, when the catheter is positioned within an aperture of an atrial wall, wherein the first balloon is positioned on a first side of the atrial wall and wherein the second balloon is positioned on a second side of the atrial wall, the catheter is held in place at the atrial wall when the first balloon and the second balloon are inflated.

According to at least one embodiment of a method for securing a catheter within a heart, the proximal end of the conduit is coupled to a suction/infusion source, and wherein at least one balloon is inflated using by the suction/infusion source. In another embodiment, the catheter further comprises a physical structure coupled to the catheter and positioned externally to the catheter, wherein the physical structure is positioned at or near the at least one balloon. In yet another embodiment, when the catheter is positioned within an aperture of an atrial wall and wherein the at least one balloon is positioned on one side of the atrial wall and the physical structure is positioned on the other side of the atrial, the catheter is held in place at the atrial wall when the at least one balloon is inflated. In an additional embodiment, the physical structure comprises a protrusion.

According to at least one embodiment of a device for assisting heart function, the device comprises a piston having a proximal end, a distal end, and an inner chamber, a cardiac processor electrically coupled to the piston, a source of gas in communication with the inner chamber of the piston at the proximal end of the piston, and a catheter having a proximal end and a distal end and having a lumen therethrough, the catheter defining at least one aperture positioned therethrough at or near the distal end of the catheter, the proximal end of the catheter in communication with the inner chamber of the piston, wherein when the distal end of the catheter is positioned within a pericardial space, the device operates to inject gas into and/or remove gas from the pericardial space. In another embodiment, actuation of the piston injects gas into the pericardial space. In yet another embodiment, actuation of the piston removes gas from the pericardial space. In an additional embodiment, the cardiac processor is operable to cause the piston to inject gas from and/or pull gas into the piston. In yet an additional embodiment, the source of gas comprises a portable gas reservoir, and wherein the gas is helium.

According to at least one embodiment of a device for assisting heart function, gas enters the pericardial space from the piston, through the lumen of the catheter, and out from the at least one aperture defined within the catheter. In another embodiment, gas is removed from the pericardial space through the at least one aperture defined within the catheter, through the lumen of the catheter, and into the piston. In yet another embodiment, the device further comprises a unilateral valve positioned between the source of gas and the piston, the unilateral valve operable to allow gas to flow from the source of gas. In an additional embodiment, the device further comprises a power supply operably coupled to the cardiac processor. In yet an additional embodiment, the power supply comprises a rechargeable battery.

According to at least one embodiment of a device for assisting heart function, the device comprising at first electromagnetic plate, the first two electromagnetic plate having an inner surface, a first non-electromagnetic plate, the first non-electromagnetic plate having an inner surface, a cardiac processor electrically coupled to the first electromagnetic plate, a bladder having a proximal end, a distal end, and an inner chamber, the bladder attached to an inner surface of the first electromagnetic plate and/or the first non-electromagnetic plate, a source of gas in communication with the inner chamber of the bladder at the proximal end of the bladder, and a catheter having a proximal end and a distal end and having a lumen therethrough, the catheter defining at least one aperture positioned therethrough at or near the distal end of the catheter, the proximal end of the catheter in communication with the inner chamber of the bladder at the distal end of the bladder, wherein when the distal end of the catheter is positioned within a pericardial space, the device operates to inject gas into and/or remove gas from the pericardial space.

According to at least one embodiment of a device for assisting heart function, the device comprises at least two electromagnetic plates, the at least two electromagnetic plates having an inner surface, a cardiac processor electrically coupled to at least one of the at least two electromagnetic plates, bladder having an inner chamber, the bladder attached to an inner surface of at least one of the at least two electromagnetic plates, a source of gas in communication with the inner chamber of the bladder, and at least one catheter having a proximal end and a distal end and having a lumen therethrough, the at least one catheter defining at least one aperture positioned therethrough at or near the distal end of the at least one catheter and comprising a pericardial balloon coupled to the at least one catheter at or near the distal end of the at least one catheter, the proximal end of the at least one catheter in communication with the inner chamber of the bladder, wherein when the distal end of the at least one catheter is positioned within a pericardial space, the device operates to inject gas into and/or remove gas from the pericardial balloon. In another embodiment, the at least two electromagnetic plates are operable to compress the bladder, wherein the compression of the bladder injects gas into the pericardial balloon to inflate the pericardial balloon. In yet another embodiment, the at least two electromagnetic plates are operable to expand the bladder, wherein the expansion of the bladder removes gas from the pericardial balloon to deflate the pericardial balloon. In an additional embodiment, gas enters the pericardial balloon from the bladder, through the lumen of the at least one catheter, and out from the at least one aperture defined within the at least one catheter. In yet an additional embodiment, gas is removed from the pericardial balloon through the at least one aperture defined within the at least one catheter, through the lumen of the at least one catheter, and into the bladder.

According to at least one embodiment of a device for assisting heart function, when the distal end of the at least one catheter is positioned within the pericardial space at or near a heart chamber, inflation of the pericardial balloon exerts pressure on an epicardial wall surrounding the heart chamber, and deflation of the pericardial balloon relieves pressure on the epicardial wall, the inflation and deflation of the pericardial balloon operable to facilitate heart function. In another embodiment, the heart chamber is a left ventricle. In yet another embodiment, the heart chamber is a right ventricle. In an additional embodiment, the at least one catheter comprises a first catheter and a second catheter. In yet an additional embodiment, the at least one catheter comprises three or more catheters.

According to at least one embodiment of a device for assisting heart function, when the distal end of the first catheter is positioned within the pericardial space at or near a first heart chamber, and wherein when the distal end of the second catheter is positioned within the pericardial space at or near a second heart chamber, inflation of the pericardial balloons coupled to the first catheter and the second catheter exerts pressure on an epicardial wall surrounding the first heart chamber and the second heart chamber, and deflation of the pericardial balloons coupled to the first catheter and the second catheter relieves pressure on the epicardial wall, the inflation and deflation of the pericardial balloons operable to facilitate heart function. In another embodiment, inflation and deflation of the pericardial balloon of the first catheter occurs during the times of inflation and deflation, respectively, of the pericardial balloon of the second catheter. In yet another embodiment, the inflation and deflation of the pericardial balloons of the first and second catheters create a counterpulsation. In an additional embodiment, inflation and deflation of the pericardial balloon of the first catheter occurs at a different times than the times of inflation and deflation, respectively, of the pericardial balloon of the second catheter. In yet an additional embodiment, the first heart chamber is a left ventricle, and wherein the second heart chamber is a right ventricle.

According to at least one embodiment of a device for assisting heart function, the pericardial balloon is made of polyurethane. In another embodiment, the pericardial balloon has an inflation volume between 30 and 40 cubic centimeters.

According to at least one embodiment of a method of assisting heart function, the method comprises the steps of providing a device for assisting heart function, comprising at least two electromagnetic plates, the at least two electromagnetic plates having an inner surface, cardiac processor electrically coupled to at least one of the at least two electromagnetic plates, a bladder having an inner chamber, the bladder attached to an inner surface of at least one of the at least two electromagnetic plates, a source of gas in communication with the inner chamber of the bladder, and at least one catheter having a proximal end and a distal end and having a lumen therethrough, the at least one catheter defining at least one aperture positioned therethrough at or near the distal end of the at least one catheter and comprising a pericardial balloon coupled to the at least one catheter at or near the distal end of the at least one catheter, the proximal end of the at least one catheter in communication with the inner chamber of the bladder, and operating the device, when the distal end of the at least one catheter is positioned within a pericardial space, to inject gas into and/or remove gas from the pericardial balloon to assist heart function.

In another embodiment, the at least two electromagnetic plates are operable to compress the bladder, wherein the compression of the bladder injects gas into the pericardial balloon to inflate the pericardial balloon. In yet another embodiment, the at least two electromagnetic plates are operable to expand the bladder, wherein the expansion of the bladder removes gas from the pericardial balloon to deflate the pericardial balloon. In an additional embodiment, gas enters the pericardial balloon from the bladder, through the lumen of the at least one catheter, and out from the at least one aperture defined within the at least one catheter.

According to at least one embodiment of a method of assisting heart function, gas is removed from the pericardial balloon through the at least one aperture defined within the at least one catheter, through the lumen of the at least one catheter, and into the bladder. In another embodiment, when the distal end of the at least one catheter is positioned within the pericardial space at or near a heart chamber, inflation of the pericardial balloon exerts pressure on an epicardial wall surrounding the heart chamber, and deflation of the pericardial balloon relieves pressure on the epicardial wall, the inflation and deflation of the pericardial balloon operable to facilitate heart function. In yet another embodiment, the heart chamber is a left ventricle. In an additional embodiment, the heart chamber is a right ventricle. In yet an additional embodiment, the at least one catheter comprises a first catheter and a second catheter. In another embodiment, the at least one catheter comprises three or more catheters.

In another embodiment, when the distal end of the first catheter is positioned within the pericardial space at or near a first heart chamber, and wherein when the distal end of the second catheter is positioned within the pericardial space at or near a second heart chamber, inflation of the pericardial balloons coupled to the first catheter and the second catheter exerts pressure on an epicardial wall surrounding the first heart chamber and the second heart chamber, and deflation of the pericardial balloons coupled to the first catheter and the second catheter relieves pressure on the epicardial wall, the inflation and deflation of the pericardial balloons operable to facilitate heart function. In yet another embodiment, inflation and deflation of the pericardial balloon of the first catheter occurs during the times of inflation and deflation, respectively, of the pericardial balloon of the second catheter. In an additional embodiment, the inflation and deflation of the pericardial balloons of the first and second catheters create a counterpulsation. In yet an additional embodiment, inflation and deflation of the pericardial balloon of the first catheter occurs at a different times than the times of inflation and deflation, respectively, of the pericardial balloon of the second catheter.

According to at least one embodiment of a method of assisting heart function, the first heart chamber is a left ventricle, and the second heart chamber is a right ventricle.

According to at least one embodiment of a method for closing an aperture in a targeted tissue, the method comprises the steps of introducing a catheter to the targeted tissue, the catheter having a lumen defined therethrough, inserting a coil within the lumen of the catheter, inserting a shaft within the lumen of the catheter, the shaft operable to position the coil at the targeted tissue, and positioning the coil within the aperture of the targeted tissue, wherein at least part of the coil is present on a first side of the targeted tissue, and wherein at least part of the coil is present on a second side of the targeted tissue. In another embodiment, the coil comprises a memory, and wherein the memory comprises a first configuration and a second configuration. In yet another embodiment, the first configuration is uncompressed, and wherein the second configuration is compressed. In an additional embodiment, the method further comprises the step of pushing the coil using the shaft so that the memory of the coil changes from a first configuration to a second configuration. In yet an additional embodiment, the method further comprises the step of pushing the coil using the shaft so that the coil compresses to close the aperture of the targeted tissue.

According to at least one embodiment of a method for closing an aperture in a targeted tissue, the method further comprises the step of twisting the coil using the shaft so that the coil compresses to close the aperture of the targeted tissue. In another embodiment, the targeted tissue is an atrial wall of a heart. In yet another embodiment, the step of inserting a coil within the lumen of the catheter comprises the step of inserting a guide wire within the lumen of the catheter prior to insertion of the coil so that the guide wire may facilitate insertion of the coil. In an additional embodiment, the step of positioning the coil results in closure of the aperture of the targeted tissue. In yet an additional embodiment, the step of introducing a catheter to the targeted tissue further comprises engagement of the targeted tissue by the catheter.

According to at least one embodiment of a system for closing an aperture in a targeted tissue, the system comprises a first catheter having a lumen defined therethrough, a coil positioned within the lumen of the catheter, and a shaft positioned within the lumen of the catheter, the shaft operable to position the coil at the targeted tissue, wherein the coil may be positioned within the aperture of the targeted tissue to close said aperture. In at least one embodiment, the coil is radiopaque. In another embodiment, the first catheter comprises a delivery catheter, and wherein the coil and the shaft are positioned within the delivery catheter. In yet another embodiment, the system further comprises a second catheter having a lumen defined therethrough, wherein the second catheter comprises an engagement catheter, and wherein the delivery catheter is positioned within the lumen of the engagement catheter. in an additional embodiment, when the coil is positioned within the aperture of the targeted tissue, at least part of the coil is present on a first side of the targeted tissue, and at least part of the coil is present on a second side of the targeted tissue. In yet an additional embodiment, the coil comprises a memory, and wherein the memory comprises a first configuration and a second configuration.

According to at least one embodiment of a system for closing an aperture in a targeted tissue, the first configuration is uncompressed, and wherein the second configuration is compressed. In another embodiment, the shaft is further operable to push the coil so that the memory of the coil changes from a first configuration to a second configuration. In yet another embodiment, the shaft is further operable to push the coil so that the coil compresses to close the aperture of the targeted tissue. In an additional embodiment, the shaft is further operable to twist the coil so that the coil compresses to close the aperture of the targeted tissue. In yet an additional embodiment, the targeted tissue is an atrial wall of a heart.

According to at least one embodiment of a system for closing an aperture in a targeted tissue, the system further comprises a guide wire positioned within the lumen of the catheter prior to positioning the coil within the lumen of the catheter so that the guide wire may facilitate positioning of the coil. In another embodiment, the engagement catheter is operable to engage the targeted tissue.

BRIEF DESCRIPTION OF THE DRAWINGS

FIG. 1A shows an embodiment of an engagement catheter and an embodiment of a delivery catheter as disclosed herein;

FIG. 1B shows a percutaneous intravascular pericardial delivery using another embodiment of an engagement catheter and another embodiment of a delivery catheter as disclosed herein;

FIG. 2A shows a percutaneous intravascular technique for accessing the pericardial space through a right atrial wall or atrial appendage using the engagement and delivery catheters shown in FIG. 1A;

FIG. 2B shows the embodiment of an engagement catheter shown in FIG. 2A;

FIG. 2C shows another view of the distal end of the engagement catheter embodiment shown in FIGS. 2A and 2B;

FIG. 3A shows removal of an embodiment of a catheter as disclosed herein;

FIG. 3B shows the resealing of a puncture according to an embodiment as disclosed herein;

FIG. 5A shows an embodiment of an engagement catheter as disclosed herein;

FIG. 5B shows a cross-sectional view of the proximal end of the engagement catheter shown in FIG. 5A;

FIG. 5C shows a cross-sectional view of the distal end of the engagement catheter shown in FIG. 5A;

FIG. 6A shows an embodiment of a delivery catheter as disclosed herein;

FIG. 6B shows a close-up view of the needle shown in FIG. 6A;

FIG. 6C shows a cross-sectional view of the needle shown in FIGS. 6A and 6B;

FIG. 9A shows another embodiment of a steering wire system as disclosed herein, the embodiment being deflected in one location;

FIG. 9B shows the steering wire system shown in FIG. 9A, wherein the steering wire system is deflected at two locations;

FIG. 9C shows the steering wire system shown in FIGS. 9A and 9B in its original position;

FIG. 15A shows another embodiment of a system for closing a hole in cardiac tissue, as disclosed herein;

FIG. 15B shows the embodiment of FIG. 15A approaching cardiac tissue;

FIG. 17A shows an embodiment of a portion of an apparatus for engaging a tissue that has engaged a tissue, as disclosed herein;

FIG. 17B shows an embodiment of a portion of an apparatus for engaging a tissue having an expanded skirt that has engaged a tissue, as disclosed herein;

FIG. 18A shows an embodiment of a portion of an apparatus for engaging a tissue having a collapsed skirt present within a sleeve, as disclosed herein;

FIG. 18B shows an embodiment of a portion of an apparatus for engaging a tissue having an expanded skirt, as disclosed herein;

FIG. 21A shows an embodiment of a portion of an apparatus for removing fluid from a tissue, as disclosed herein;

FIG. 21B shows an embodiment of a portion of an apparatus comprising grooves for removing fluid from a tissue, as disclosed herein;

FIG. 25A shows an embodiment of a portion of a suction/infusion catheter, apparatus as disclosed herein;

FIG. 25B shows an embodiment of a portion of a suction/infusion catheter comprising grooves, as disclosed herein;

FIG. 30A shows an embodiment of a suction/infusion catheter with a pericardial balloon coupled thereto, as disclosed herein;

FIG. 30B shows the embodiment of FIG. 30A with an inflated pericardial balloon;

FIG. 32A shows an embodiment of a suction/infusion catheter with a pericardial balloon positioned within a pericardial space at or near the left ventricle of a heart, as disclosed herein; and FIG. 32B shows an embodiment of a device/apparatus of the present disclosure comprising multiple suction/infusion catheters with pericardial balloons present within a pericardial space surrounding a heart, as disclosed herein.

DETAILED DESCRIPTION

Figure 4A:
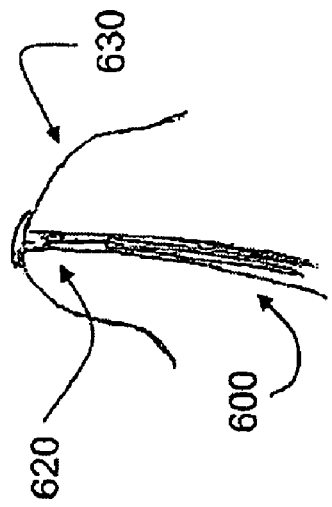
FIG. 4A to 4C show a closure of a hole in the atrial wall using an embodiment as disclosed herein.

It will be appreciated by those of skill in the art that the following detailed description of the disclosed embodiments is merely exemplary in nature and is not intended to limit the scope of the appended claims.

The disclosed embodiments include devices, systems, and methods useful for accessing various tissues of the heart from inside the heart and is directed to devices, systems, and methods for treating patients with congestive heart failure (CHF), including those patients with a different functional class of CHF. For example, various embodiments provide for percutaneous, intravascular access into the pericardial space through an atrial wall or the wall of an atrial appendage. In at least some embodiments, the heart wall is aspirated and retracted from the pericardial sac to increase the pericardial space between the heart and the sac and thereby facilitate access into the space. Systems and devices of the present disclosure are considered as a support for the native heart contraction and as a non-blood contact system or device. Suction (to enhance myocardial perfusion in diastole) and compression (to assist and unload the heart in systole) in the pericardial space are synchronized with the cardiac cycle in accordance with the devices, systems, and methods of the present disclosure.

The devices, systems, and methods of the present disclosure are characterized by the use of the pericardial sac (the space between parietal pericardium and visceral pericardium) as a pump bladder. The injection and suction of a noble gas through a catheter of the present disclosure in to and out of the heart is performed in a controlled manner by synchrony with the cardiac cycle.

The present disclosure provides interesting new revelations on how topically applied negative pressure may improve microvascular blood flow in the myocardium. Studies have shown that when myocardium was exposed to a topical negative pressure of −50 mm Hg, an immediate significant increase in microvascular blood flow was observed. This is in accordance with previous results showing increased microvascular blood flow of the skeletal muscle upon application of TNP. Lindstedt S. et al. (2007). The devices, systems, and methods of the present disclosure relate to such an improvement in blood flow by novel and beneficial means as described herein.

Unlike the relatively stiff pericardial sac, the atrial wall and atrial appendage are rather soft and deformable. Hence, suction of the atrial wall or atrial appendage can provide significantly more clearance of the cardiac structure from the pericardium as compared to suction of the pericardium. Furthermore, navigation from the intravascular region (inside of the heart) provides more certainty of position of vital cardiac structures than does intrathoracic access (outside of the heart).

Access to the pericardial space may be used for identification of diagnostic markers in the pericardial fluid; for pericardiocentesis; and for administration of therapeutic factors with angiogenic, myogenic, and antiarrhythmic potential. In addition, as explained in more detail below, epicardial pacing leads may be delivered via the pericardial space, and an ablation catheter may be used on the epicardial tissue from the pericardial space.

In the embodiment of the catheter system shown in FIG. 1A, catheter system 10 includes an engagement catheter 20, a delivery catheter 30, and a needle 40. Although each of engagement catheter 20, delivery catheter 30, and needle 40 has a proximal end and a distal end, FIG. 1A shows only the distal end. Engagement catheter 20 has a lumen through which delivery catheter 30 has been inserted, and delivery catheter 30 has a lumen through which needle 40 has been inserted. Delivery catheter 30 also has a number of openings 50 that can be used to transmit fluid from the lumen of the catheter to the heart tissue in close proximity to the distal end of the catheter.

As shown in more detail in FIGS. 2A, 2B, 2C, engagement catheter 20 includes a vacuum channel 60 used for suction of a targeted tissue 65 in the heart and an injection channel 70 used for infusion of substances to targeted tissue 65, including, for example, a biological or non-biological degradable adhesive. As is shown in FIGS. 2B and 2C, injection channel 70 is ring-shaped, which tends to provide relatively even dispersal of the infused substance over the targeted tissue, but other shapes of injection channels may be suitable. A syringe 80 is attached to injection channel 70 for delivery of the appropriate substances to injection channel 70, and a syringe 90 is attached to vacuum channel 60 through a vacuum port (not shown) at the proximal end of engagement catheter 20 to provide appropriate suction through vacuum channel 60. At the distal end of engagement catheter 20, a suction port 95 is attached to vacuum channel 60 for contacting targeted tissue 65, such that suction port 95 surrounds targeted tissue 65, which is thereby encompassed within the circumference of suction port 95. Although syringe 90 is shown in FIG. 2B as the vacuum source providing suction for engagement catheter 20, other types of vacuum sources may be used, such as a controlled vacuum system providing specific suction pressures. Similarly, syringe 80 serves as the external fluid source in the embodiment shown in FIG. 2B, but other external fluid sources may be used.

A route of entry for use of various embodiments disclosed herein is through the jugular or femoral vein to the superior or inferior vena cavae, respectively, to the right atrial wall or atrial appendage (percutaneously) to the pericardial sac (through puncture).

Referring now to FIG. 1B, an engagement catheter 100 is placed via standard approach into the jugular or femoral vein. The catheter, which may be 4 or 5 Fr., is positioned under fluoroscopic or echocardiographic guidance into the right atrial appendage 110. Suction is initiated to aspirate a portion of atrial appendage 110 away from the pericardial sac 120 that surrounds the heart. As explained herein, aspiration of the heart tissue is evidenced when no blood can be pulled back through engagement catheter 100 and, if suction pressure is being measured, when the suction pressure gradually increases. A delivery catheter 130 is then inserted through a lumen of engagement catheter 100. A small perforation can be made in the aspirated atrial appendage 110 with a needle such as needle 40, as shown in FIGS. 1A and 2A. A guide wire (not shown) can then be advanced through delivery catheter 130 into the pericardial space to secure the point of entry 125 through the atrial appendage and guide further insertion of delivery catheter 130 or another catheter. Flouroscopy or echocardiogram can be used to confirm the position of the catheter in the pericardial space. Alternatively, a pressure tip needle can sense the pressure and measure the pressure change from the atrium (about 10 mmHg) to the pericardial space (about 2 mmHg). This is particularly helpful for transeptal access where puncture of arterial structures (e.g., the aorta) can be diagnosed and sealed with an adhesive, as described in more detail below.

Although aspiration of the atrial wall or the atrial appendage retracts the wall or appendage from the pericardial sac to create additional pericardial space, $CO_2$ gas can be delivered through a catheter, such as delivery catheter 130, into the pericardial space to create additional space between the pericardial sac and the heart surface.

Referring now to FIG. 3A, the catheter system shown in FIG. 1B is retrieved by pull back through the route of entry. However, the puncture of the targeted tissue in the heart (e.g., the right atrial appendage as shown in FIG. 3A) may be sealed upon withdrawal of the catheter, which prevents bleeding into the pericardial space. The retrieval of the catheter may be combined with a sealing of the tissue in one of several ways: (1) release of a tissue adhesive or polymer 75 via injection channel 70 to seal off the puncture hole, as shown in FIG. 3B; (2) release of an inner clip or mechanical stitch to close off the hole from the inside of the cavity or the heart, as discussed herein; or (3) mechanical closure of the heart with a sandwich type mechanical device that approaches the hole from both sides of the wall (see FIGS. 4A, 4B, and 4C). In other words, closure may be accomplished by using, for example, a biodegradable adhesive material (e.g., fibrin glue or cyanomethacrylate), a magnetic system, or an umbrella-shaped nitinol stent. An example of the closure of a hole in the atrium is shown in FIG. 3B. Engagement catheter 20 is attached to targeted tissue 95 using suction through suction port 60. Tissue adhesive 75 is injected through injection channel 70 to coat and seal the puncture wound in targeted tissue 95. Engagement catheter 20 is then withdrawn, leaving a plug of tissue adhesive 75 attached to the atrial wall or atrial appendage.

Figure 4B:
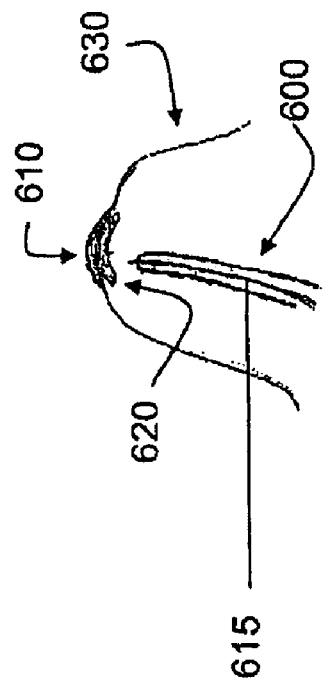
Figure 4C:
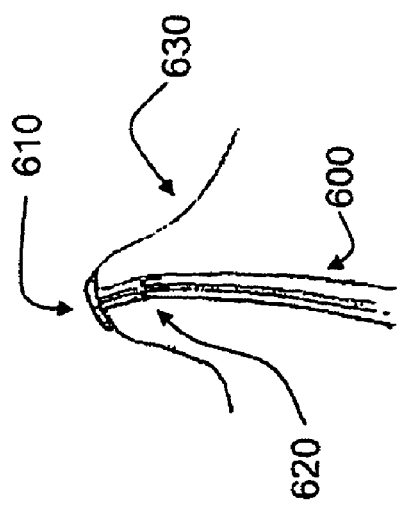

Other examples for sealing the puncture wound in the atrial wall or appendage are shown in FIGS. 4A-4F. Referring now to FIGS. 4A-4C, a sandwich-type closure member, having an external cover 610 and an internal cover 620, is inserted through the lumen of engagement catheter 600, which is attached to the targeted tissue of an atrial wall 630. Each of external and internal covers 610 and 620 is similar to an umbrella in that it can be inserted through a catheter in its folded configuration and expanded to an expanded configuration once it is outside of the catheter. As shown in FIG. 4A, external cover 610 is deployed (in its expanded configuration) on the outside of the atrial wall to seal a puncture wound in the targeted tissue, having already been delivered through the puncture wound into the pericardial space. Internal cover 620 is delivered through engagement catheter 600 (in its folded configuration), as shown in FIGS. 4A and 4B, by an elongated delivery wire 615, to which internal cover 620 is reversibly attached (for example, by a screw-like mechanism). Once internal cover 620 is in position on the inside of atrial wall 630 at the targeted tissue, internal cover 620 is deployed to help seal the puncture wound in the targeted tissue (see FIG. 4C).

Internal cover 620 and external cover 610 may be made from a number of materials, including a shape-memory alloy such as nitinol. Such embodiments are capable of existing in a catheter in a folded configuration and then expanding to an expanded configuration when deployed into the body. Such a change in configuration can result from a change in temperature, for example. Other embodiments of internal and external covers may be made from other biocompatible materials and deployed mechanically.

After internal cover 620 is deployed, engagement catheter 600 releases its grip on the targeted tissue and is withdrawn, leaving the sandwich-type closure to seal the puncture wound, as shown in FIG. 4C. External cover 610 and internal cover 620 may be held in place using a biocompatible adhesive. Similarly, external cover 610 and internal cover 620 may be held in place using magnetic forces, such as, for example, by the inside face (not shown) of external cover 610 comprising a magnet, by the inside face (not shown) of internal cover 620 comprising a magnet, or both inside faces of external cover 610 or internal cover 620 comprising magnets.

Figure 4D:
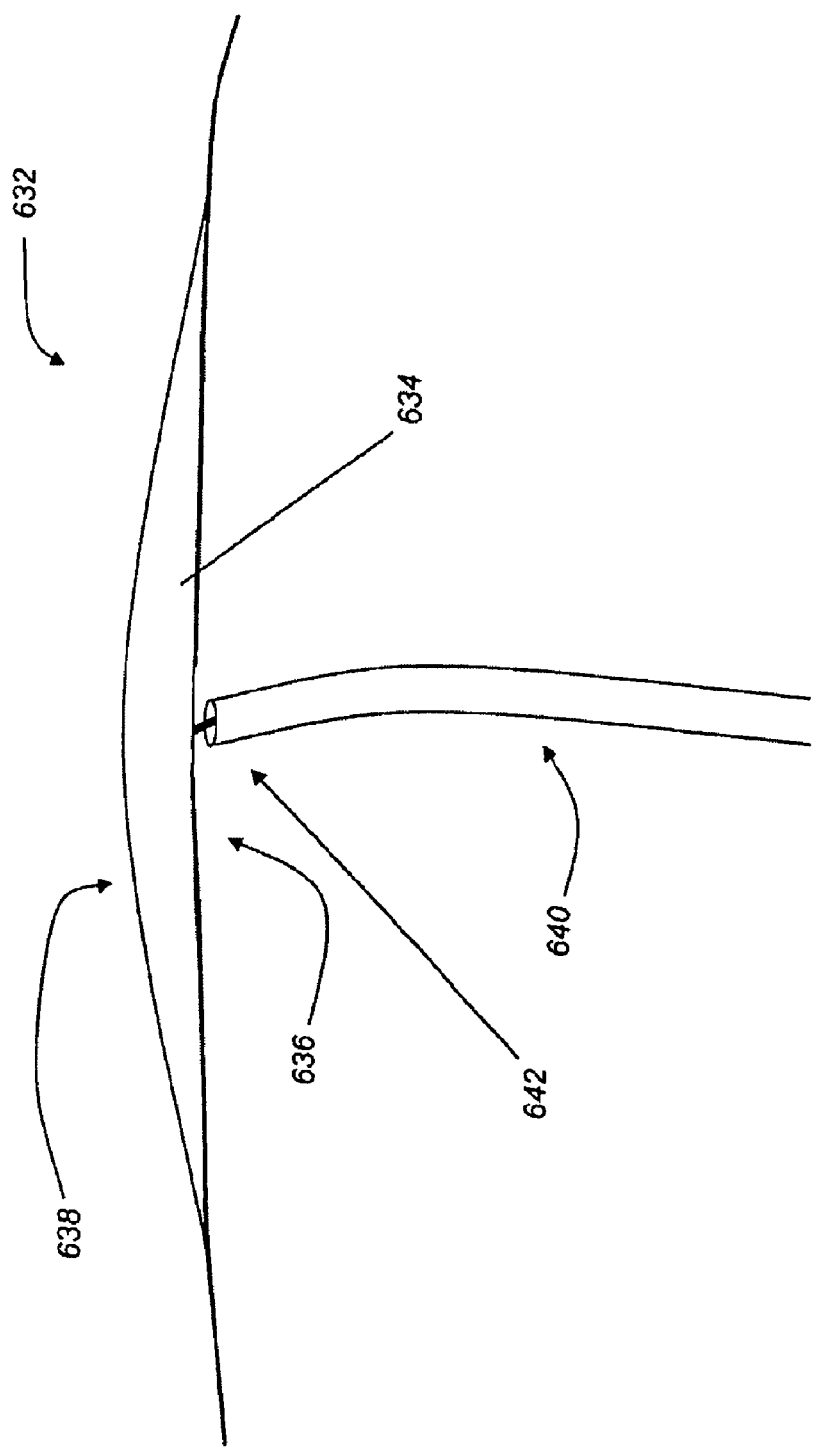
FIG. 4D shows another closure of a hole in cardiac tissue using another embodiment as disclosed herein.

In the embodiment shown in FIGS. 4A, 4B, and 4C, the closure member comprises external cover 610 and internal cover 620. However, in at least certain other embodiments, the closure member need not have two covers. For example, as shown in FIG. 4D, closure member 632 is made of only one cover 634. Cover 634 has a first face 636 and a second face 638, and first face 636 is configured for reversible attachment to distal end 642 of delivery wire 640. Closure member 632 may be made of any suitable material, including nitinol, which is capable of transitioning from a folded configuration to an expanded configuration.

Figure 4E:
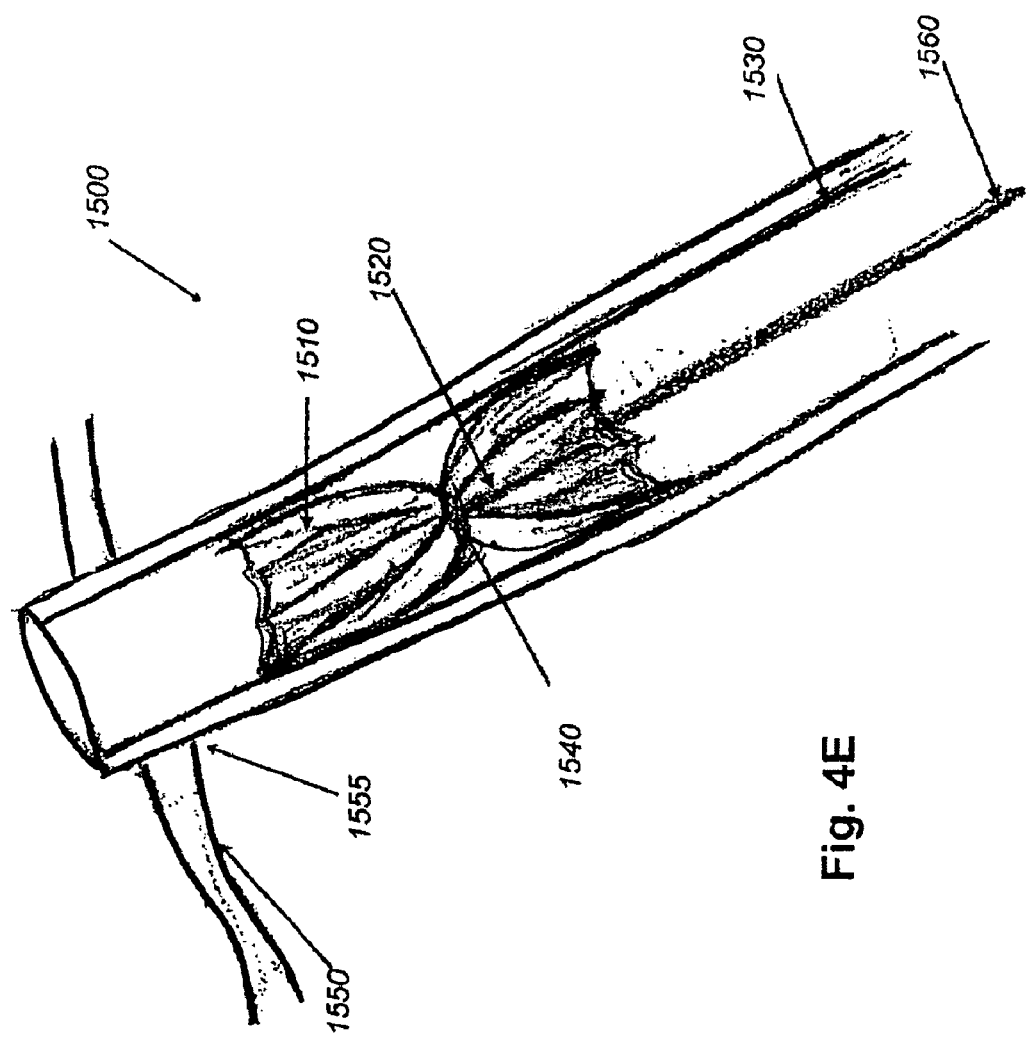
FIG. 4E shows yet another closure of a hole in cardiac tissue using another embodiment as disclosed herein.

In the embodiment shown in FIG. 4E, a closure member 1500 comprises an external cover 1510 and an internal cover 1520 within a delivery catheter 1530. External cover 1510 and internal cover 1520 are attached at a joint 1540, which may be formed, for example, by a mechanical attachment or by a magnetic attachment. In embodiments having a magnetic attachment, each of the external cover and the internal cover may have a ferromagnetic component that is capable of magnetically engaging the other ferromagnetic component.

Delivery catheter 1530 is shown after insertion through hole 1555 of atrial wall 1550. Closure member 1500 may be advanced through delivery catheter 1530 to approach atrial wall 1550 by pushing rod 1560. Rod 1560 may be reversibly attached to internal cover 1520 so that rod 1560 may be disconnected from internal cover 1520 after closure member 1500 is properly deployed. For example, rod 1560 may engage internal cover 1520 with a screw-like tip such that rod 1560 may be easily unscrewed from closure member 1500 after deployment is complete. Alternatively, rod 1560 may simply engage internal cover 1520 such that internal cover 1520 may be pushed along the inside of delivery catheter 1530 without attachment between internal cover 1520 and rod 1560.

Closure member 1500 is advanced through delivery catheter 1530 until external cover 1510 reaches a portion of delivery catheter 1530 adjacent to atrial wall 1550; external cover 1510 is then pushed slowly out of delivery catheter 1530 into the pericardial space. External cover 1510 then expands and is positioned on the outer surface of atrial wall 1550. When external cover 1510 is properly positioned on atrial wall 1550, joint 1540 is approximately even with atrial wall 1550 within hole 1555. Delivery catheter 1530 is then withdrawn slowly, causing hole 1555 to close slightly around joint 1540. As delivery catheter 1530 continues to be withdrawn, internal cover 1520 deploys from delivery catheter 1530, thereby opening into its expanded formation. Consequently, atrial wall 1550 is pinched between internal cover 1520 and external cover 1510, and hole 1555 is closed to prevent leakage of blood from the heart.

Figure 4F:
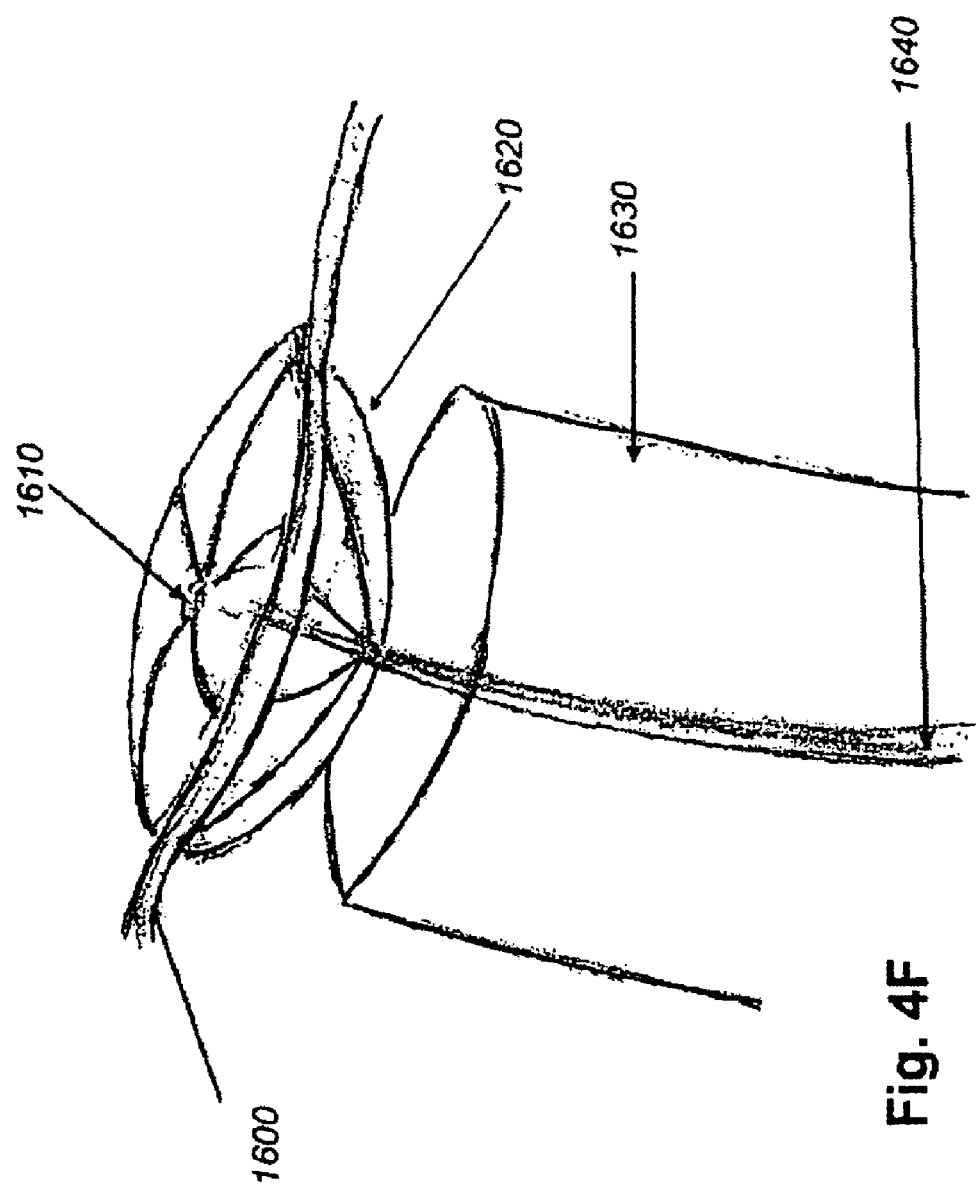
FIG. 4F shows still another closure of a hole in cardiac tissue using another embodiment as disclosed herein.

FIG. 4F shows the occlusion of a hole (not shown) in atrial wall 1600 due to the sandwiching of atrial wall 1600 between an external cover 1610 and an internal cover 1620. External cover 1610 is shown deployed on the outside surface of atrial wall 1600, while delivery catheter 1630 is deployed on the inside surface of atrial wall 1600. As shown, rod 1640 is engaged with internal cover 1620, and delivery catheter 1650 is in the process of being withdrawn, which allows internal cover 1620 to fully deploy. Rod 1640 is then withdrawn through delivery catheter 1630. An engagement catheter (not shown) may surround delivery catheter 1650, as explained more fully herein.

Other examples for sealing a puncture wound in the cardiac tissue are shown in FIGS. 12-15. Referring now to FIG. 12A, there is shown a plug 650 having a first end 652, a second end 654, and a hole 656 extending from first end 652 to second end 654. Plug 650 may be made from any suitable material, including casein, polyurethane, silicone, and polytetrafluoroethylene. Wire 660 has been slidably inserted into hole 656 of plug 650. Wire 660 may be, for example, a guide wire or a pacing lead, so long as it extends through the hole in the cardiac tissue (not shown). As shown in FIG. 2A, first end 652 is covered with a radiopaque material, such as barium sulfate, and is therefore radiopaque. This enables the clinician to view the placement of the plug in the body using radiographic imaging. For example, the clinician can confirm the location of the plug during the procedure, enabling a safer and more effective procedure for the patient.

Figure 12C:
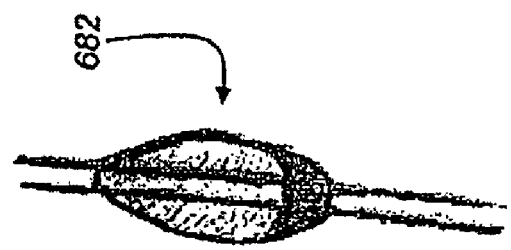
FIG. 12C shows another embodiment of a system for closing a hole in cardiac tissue, as disclosed herein.
Figure 12B:
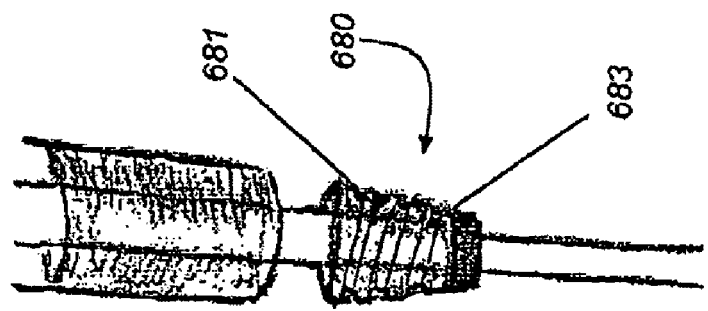
FIG. 12B shows another embodiment of a system for closing a hole in cardiac tissue, as disclosed herein.
Figure 12A:
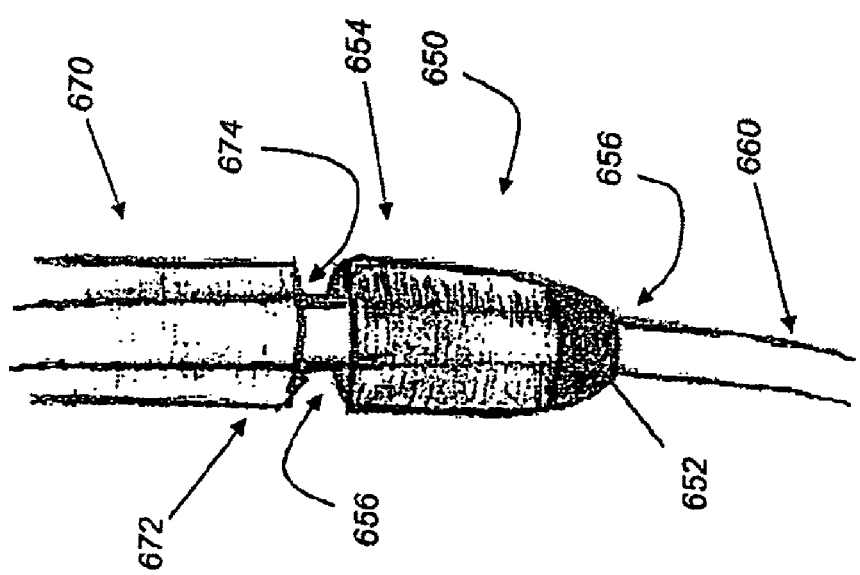
FIG. 12A shows an embodiment of a system for closing a hole in cardiac tissue, as disclosed herein.

As shown in FIG. 12A, first end 652 of plug 650 has a smaller diameter than second end 654 of plug 650. Indeed, plug 680 shown FIG. 12B and plug 684 shown in FIGS. 13 and 14 have first ends that are smaller in diameter than their respective second ends. However, not all embodiments of plug have a first end that is smaller in diameter than the second end. For example, plug 682 shown in FIG. 12C has a first end with a diameter that is not smaller than the diameter of the second end. Both types of plug can be used to close holes in cardiac tissue.

Referring again to FIG. 12A, elongated shaft 670 has a proximal end (not shown), a distal end 672, and a lumen 674 extending from the proximal end to distal end 672. Although no catheter is shown in FIG. 12A, plug 650, wire 660, and shaft 670 are configured for insertion into a lumen of a catheter (see FIG. 14), such as an embodiment of an engagement catheter disclosed herein. Plug 650 and shaft 670 are also configured to be inserted over wire 660 and can slide along wire 660 because each of lumen 656 of plug 650 and lumen 674 of shaft 670 is slightly larger in circumference than wire 660.

Figure 13:
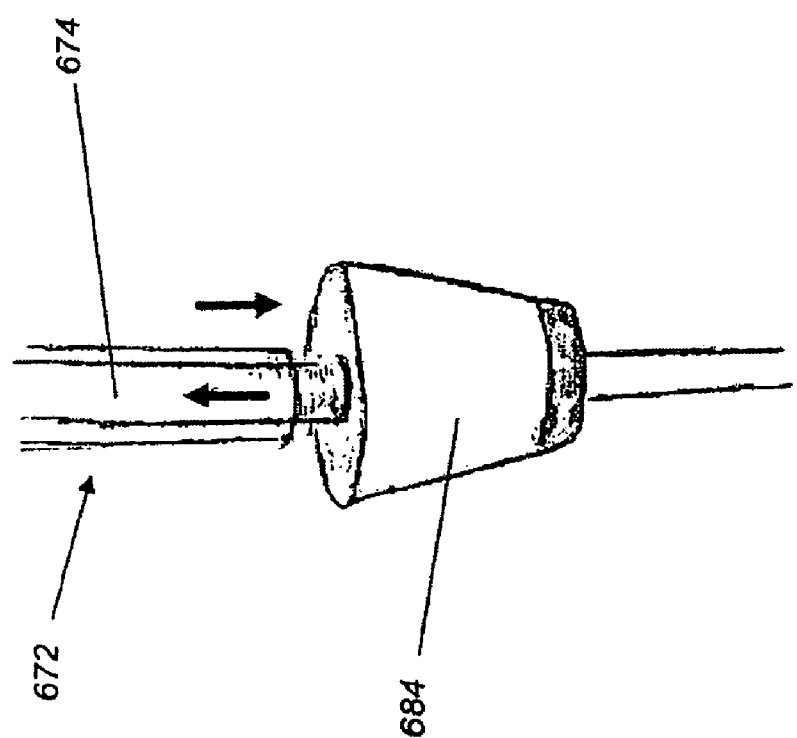
FIG. 13 shows another embodiment of a system for closing a hole in cardiac tissue, as disclosed herein.
Figure 14:
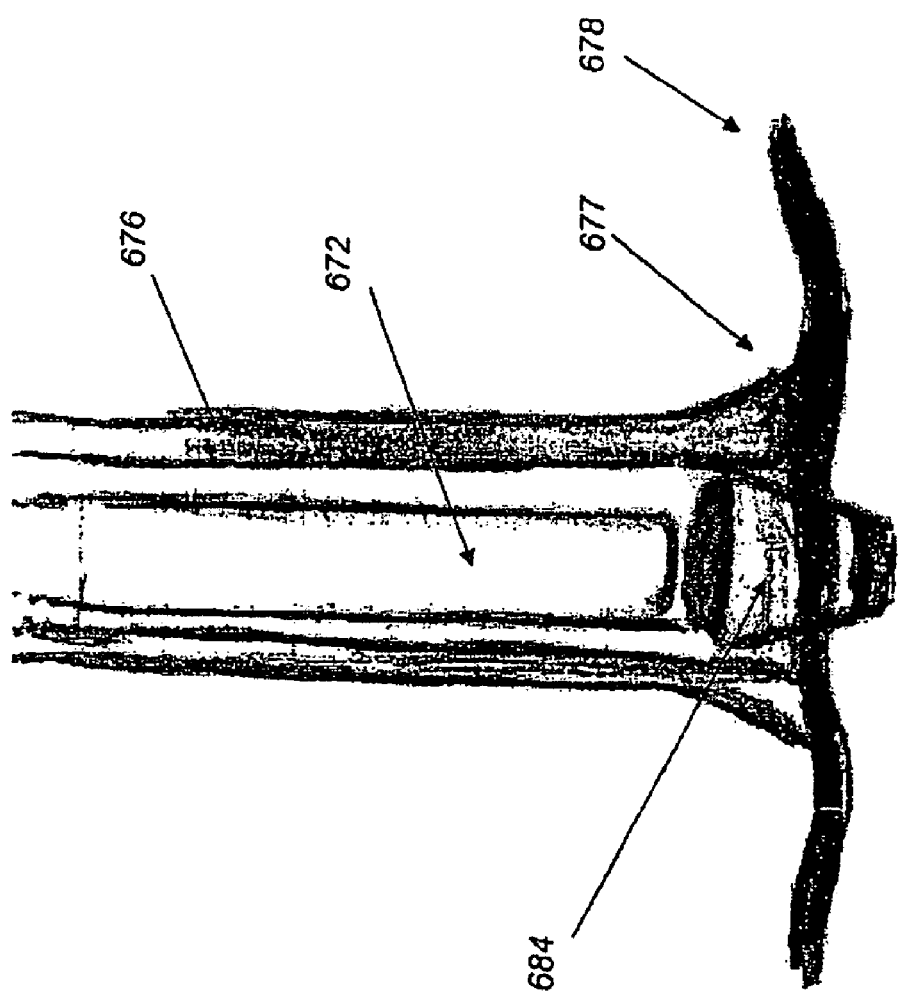
FIG. 14 shows another embodiment of a system for closing a hole in cardiac tissue, as disclosed herein.

As shown in FIGS. 13 and 14, shaft 672 is used to push plug 684 along wire 674 within elongated tube 676 to and into the hole in the targeted cardiac tissue 678. Distal end 677 of elongated tube 676 is shown attached to cardiac tissue 678, but distal end 677 need not be attached to cardiac tissue 678 so long as distal end 677 is adjacent to cardiac tissue 678. Once plug 684 is inserted into the hole, wire 674 may be withdrawn from the hole in plug 684 and the interior of the heart (not shown) and shaft 672 is withdrawn from elongated tube 676. In some embodiments, the plug is self-sealing, meaning that the hole of the plug closes after the wire is withdrawn. For example, the plug may be made from a dehydrated protein matrix, such as casein or ameroid, which swells after soaking up fluid. After shaft 672 is withdrawn, elongated tube 676 can be withdrawn from the heart.

It should be noted that, in some embodiments, the wire is not withdrawn from the hole of the plug. For example, where the wire is a pacing lead, the wire may be left within the plug so that it operatively connects to the CRT device.

Referring now to FIG. 12B, there is shown a plug 680 that is similar to plug 684. However, plug 680 comprises external surface 681 having a ridge 683 that surrounds plug 680 in a helical or screw-like shape. Ridge 683 helps to anchor plug 680 into the hole of the targeted tissue (not shown). Other embodiments of plug may include an external surface having a multiplicity of ridges surrounding the plug, for example, in a circular fashion.

Figure 15C:
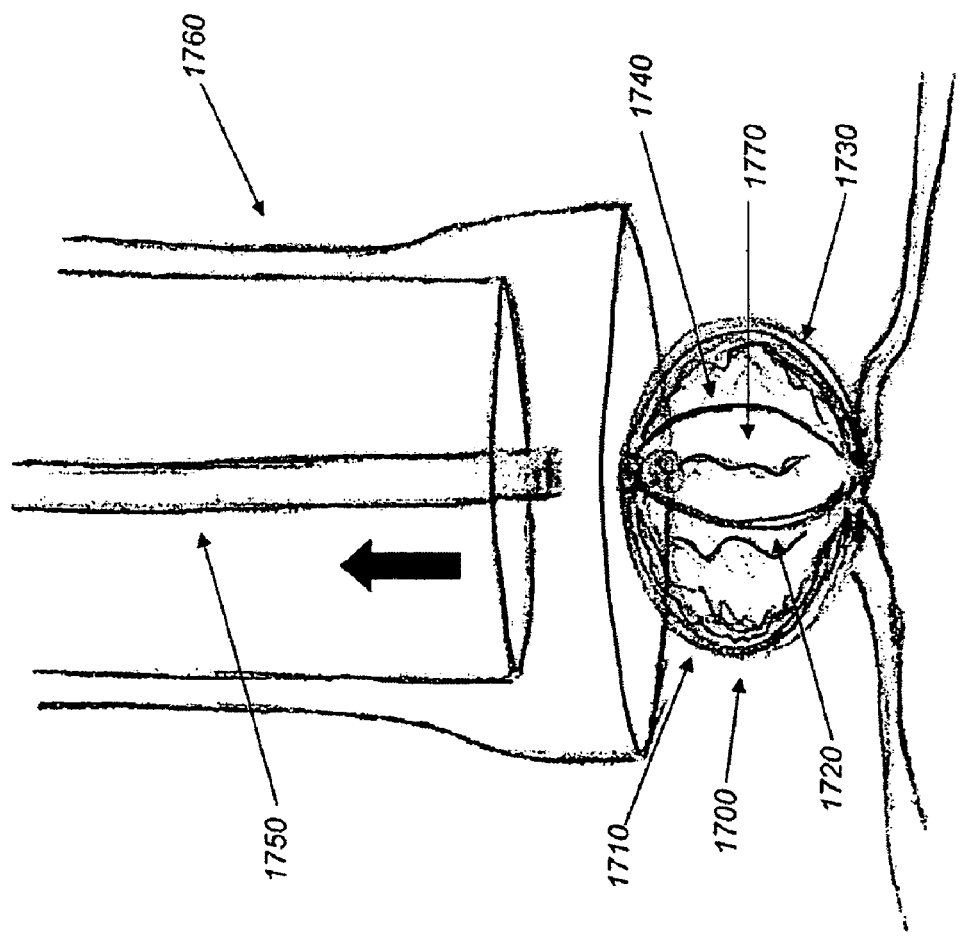
FIG. 15C shows the embodiment of FIGS. 15A-15C deployed on the cardiac tissue.

FIGS. 15A-15C show yet another embodiment of a closure member for closing a hole in a tissue. Spider clip 1700 is shown within catheter 1702 and comprises a head 1705 and a plurality of arms 1710, 1720, 1730, and 1740. Each of arms 1710, 1720, 1730, and 1740 is attached at its proximal end to head 1705. Although spider clip 1700 has four arms, other embodiments of spider clip include fewer than, or more than, four arms. For example, some embodiments of spider clip have three arms, while others have five or more arms.

Referring again to FIGS. 15A-15C, arms 1710, 1720, 1730, and 1740 may be made from any flexible biocompatible metal that can transition between two shapes, such as a shape-memory alloy (e.g., nitinol) or stainless steel. Spider clip 1700 is capable of transitioning between an open position (see FIG. 15A), in which the distal ends of its arms 1710, 1720, 1730, and 1740 are spaced apart, and a closed position (see FIG. 15C), in which the distal ends of arms 1710, 1720, 1730, and 1740 are gathered together. For embodiments made from a shape-memory alloy, the clip can be configured to transition from the open position to the closed position when the metal is warmed to approximately body temperature, such as when the clip is placed into the cardiac tissue. For embodiments made from other types of metal, such as stainless steel, the clip is configured in its closed position, but may be transitioned into an open position when pressure is exerted on the head of the clip. Such pressure causes the arms to bulge outward, thereby causing the distal ends of the arms to separate.

In this way, spider clip 1700 may be used to seal a wound or hole in a tissue, such as a hole through the atrial wall. For example, FIG. 15B shows spider clip 1700 engaged by rod 1750 within engagement catheter 1760. As shown, engagement catheter 1760 has a bell-shaped suction port 1765, which, as disclosed herein, has aspirated cardiac tissue 1770. Cardiac tissue 1770 includes a hole 1775 therethrough, and suction port 1765 fits over hole 1775 so as to expose hole 1775 to spider clip 1700.

Rod 1750 pushes spider clip 1700 through engagement catheter 1760 to advance spider clip 1700 toward cardiac tissue 1770. Rod 1750 simply engages head 1705 by pushing against it, but in other embodiments, the rod may be reversibly attached to the head using a screw-type system. In such embodiments, the rod may be attached and detached from the head simply by screwing the rod into, or unscrewing the rod out of, the head, respectively.

In at least some embodiments, the spider clip is held in its open position during advancement through the engagement catheter by the pressure exerted on the head of the clip by the rod. This pressure may be opposed by the biasing of the legs against the engagement catheter during advancement.

Referring to FIG. 15C, spider clip 1700 approaches cardiac tissue 1770 and eventually engages cardiac tissue 1770 such that the distal end of each of arms 1710, 1720, 1730, and 1740 contacts cardiac tissue 1670. Rod 1750 is disengaged from spider clip 1700, and spider clip 1700 transitions to its closed position, thereby drawing the distal ends of arms 1710, 1720, 1730, and 1740 together. As the distal ends of the arms are drawn together, the distal ends grip portions of cardiac tissue 1770, thereby collapsing the tissue between arms 1710, 1720, 1730, and 1740 such that hole 1775 is effectively closed.

Rod 1750 is then withdrawn, and engagement catheter 1760 is disengaged from cardiac tissue 1770. The constriction of cardiac tissue 1770 holds hole 1775 closed so that blood does not leak through hole 1775 after engagement catheter 1760 is removed. After a relatively short time, the body's natural healing processes permanently close hole 1775. Spider clip 1700 may remain in the body indefinitely.

Figure 15F:
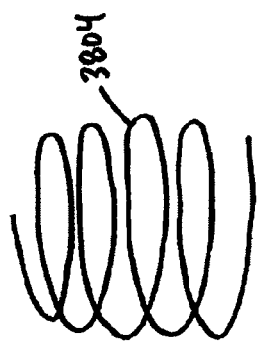
FIG. 15F shows an embodiment of a coil of a system for closing an aperture in cardiac tissue, as disclosed herein.
Figure 15E:
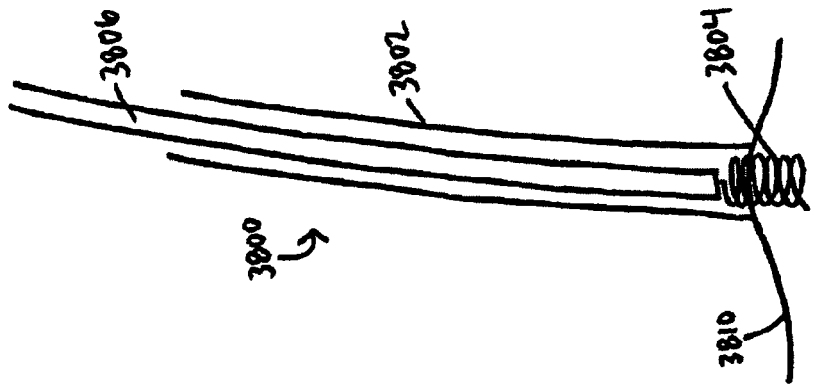
FIG. 15E shows an embodiment of a system for closing an aperture in cardiac tissue wherein a coil has partially or fully closed the hole, as disclosed herein.
Figure 15D:
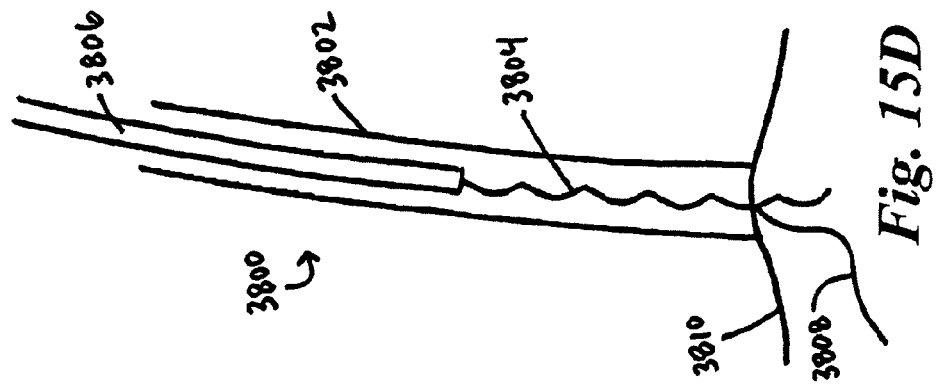
FIG. 15D shows an embodiment of a system for closing an aperture in cardiac tissue, as disclosed herein.

FIG. 15D shows an exemplary embodiment of a system for closing an aperture in a tissue according to the present disclosure. As shown in FIG. 15D, system 3800 comprises a catheter 3802, including, but no limited to, an engagement, delivery, and/or suction/infusion catheter as described herein, and further comprises a coil 3804 and a shaft 3806 positioned within an internal lumen of catheter 3802. In the exemplary embodiment shown in FIG. 15D, an optional guide wire 3808 may be used to facilitate the positioning of catheter 3802 to an atrial wall 3810. In at least one embodiment, catheter 3802 comprises an engagement catheter, wherein the engagement catheter has engaged an atrial wall 3810, and wherein an aperture within atrial wall 3810 allows, for example, a guide wire 3808, a delivery catheter, a suction/infusion catheter, and/or another device or apparatus to enter the aperture within the atrial wall 3810.

In at least one embodiment, coil 3804 is substantially straight when it is introduced within a lumen of a catheter 3802. In another embodiment, coil 3804 is somewhat, but not fully, coiled as it is introduced within the lumen of catheter 3800. In at least one embodiment, coil 3804 comprises a "memory," wherein the memory comprises a first configuration. In an exemplary embodiment, the first configuration is an uncompressed configuration. In another embodiment, the memory further comprises a second configuration, and in at least one embodiment, the second configuration is a compressed configuration. In at least one embodiment, coil 3804 is fluoroscopic so that a user of coil 3804 may use, for example, x-ray technology, to assist with placement of coil 3804 within a body.

In the exemplary embodiment shown in FIG. 15D, coil 3804 is positioned within the lumen of catheter 3802, and as coil 3804 is introduced at or near the atrial wall 3810, a portion of coil 3804 is positioned within an aperture within atrial wall 3810. When positioned, coil 3804 may be compressed using, for example, shaft 3806, whereby shaft 3806 exerts pressure upon coil 3804, causing coil 3804 to compress at or near the aperture within atrial wall 3810. In the embodiment shown in FIG. 15E, shaft 3806 has exerted pressure upon coil 3804, causing coil 3804 to compress on both sides of atrial wall 3810 (with part of coil 3804 positioned within a pericardial sac and part of the coil positioned within an atrial cavity). This compression may then facilitate closure of an aperture within atrial wall 3810, as portions of coil 3804, when compressed as shown in FIG. 15E, may exert pressure on one or both sides of atrial wall 3810, wherein the aperture within atrial wall 3810 may either be partially or fully occluded by coil 3804. FIG. 15F shows an exemplary embodiment of a coil 3804 in a compressed formation.

It can be appreciated that pressure exerted upon coil 3804 by shaft 3806 may also facilitate placement of coil 3804 at or near an aperture within atrial wall 3810. In at least one embodiment, coil 3804 may be "screwed" into an aperture within atrial wall 3810, using shaft 3806 and/or by physically turning coil 3804 as it is positioned within atrial wall 3810. In addition, and in at least one embodiment, guide wire 3808 may facilitate placement of coil 3804 within an aperture of atrial wall 3810.

Any number of materials may be used to form coil 3804, including, but not limited to, nitinol and/or stainless steel. In addition, coil 3804 may be coated with one or more materials, including, but not limited to, polytetrafluoroethylene (PTFE), polyethylene terephthalate (Dacron, for example), and/or polyurethane. In addition, one or more other materials, including, but not limited to, materials known in the art to facilitate blood coagulation, including, but not limited to, cotton fibers, may be coupled to coil 3804 to facilitate aperture occlusion.

Figure 16A:
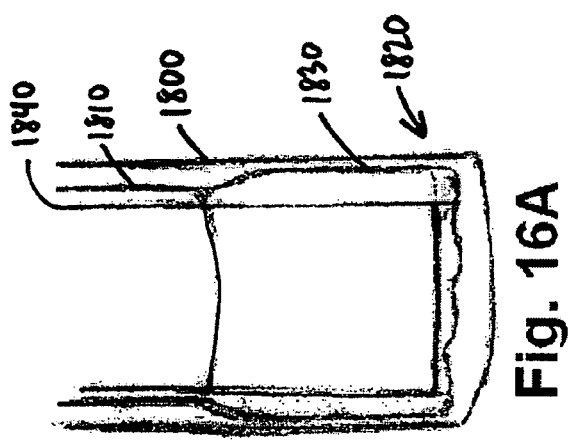
FIG. 16A shows an embodiment of a portion of an apparatus for engaging a tissue having a skirt positioned substantially within a sleeve, as disclosed herein.
Figure 16B:
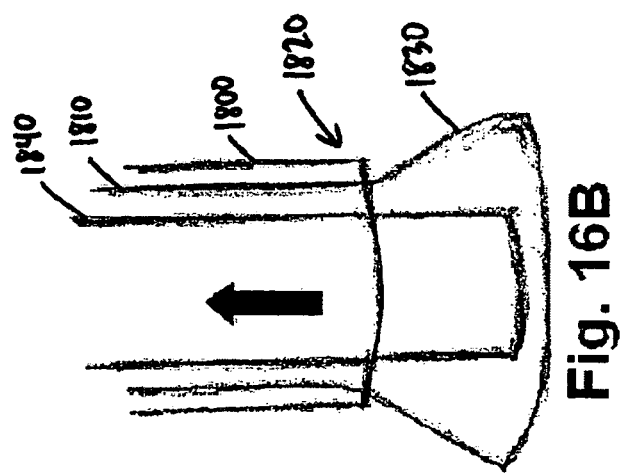
FIG. 16B shows another embodiment of a portion of an apparatus for engaging a tissue, as disclosed herein.
Figure 16C:
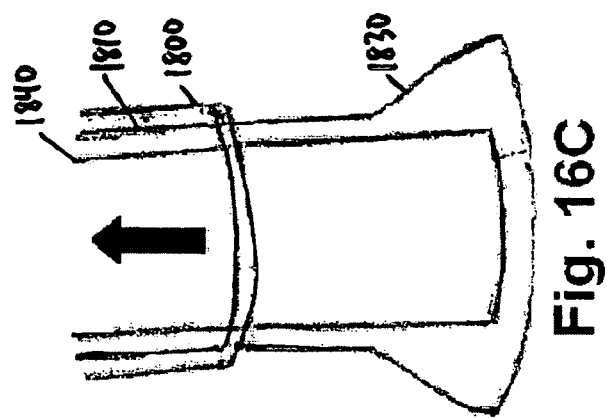
FIG. 16C shows an embodiment of a portion of an apparatus for engaging a tissue having a skirt positioned substantially outside of a sleeve, as disclosed herein.

FIGS. 16A, 16B, and 16C show an embodiment of a portion of an apparatus for engaging a tissue as disclosed herein. As shown in FIG. 16A, a sleeve 1800 is present around at least a portion of an engagement catheter 1810. Sleeve 1800, as described herein, may comprise a rigid or flexible tube having a lumen therethrough, appearing around the outside of engagement catheter 1810 and slidingly engaging engagement catheter 1810. In at least the embodiment shown in FIG. 16A, the distal end 1820 of engagement catheter 1810 comprises a skirt 1830, shown in FIG. 16A as being housed within sleeve 1800. A delivery catheter 1840 may be present within engagement catheter 1810 as shown to facilitate the delivery of a product (gas, liquid, and/or particulate(s)) to a target site. In this embodiment, delivery catheter 1840 is present at least partially within the lumen of engagement catheter 1810, and engagement catheter is placed at least partially within the lumen of sleeve 1800.

Referring now to FIG. 16B, an embodiment of an apparatus as shown in FIG. 16A or similar to the embodiment shown in FIG. 16A is shown with sleeve 1800 being "pulled back" from the distal end of engagement catheter 1810. As shown in FIG. 16B, as sleeve 1800 is pulled back (in the direction of the arrow), skirt 1830 becomes exposed, and as sleeve 1800 is no longer present around skirt 1830, skirt 1830 may optionally expand into a frusto-conical ("bell-shaped") skirt 1830. Skirt 1830 may be reversibly deformed (collapsed) when present within the lumen of sleeve 1800 as shown in FIG. 16A and in FIG. 18A described in further detail herein. It can be appreciated that many alternative configurations of skirt 1830 to the frusto-conical configuration may exist, including an irregular frusto-conical configuration, noting that a configuration of skirt 1830 having a distal portion (closest to a tissue to be engaged) larger than a proximal position may benefit from suction of a larger surface area of a tissue as described in further detail herein.

FIG. 16C shows an embodiment of an apparatus described herein having an expanded skirt 1830. As shown in FIG. 16C, sleeve 1800 has been pulled back (in the direction of the arrow) so that the expanded configuration of skirt 1830 may be present to engage a tissue (not shown).

FIGS. 17A and 17B shown alternative embodiments of a portion of an apparatus for engaging a tissue as described herein. FIGS. 17A and 17B each show a sleeve 1800, an engagement catheter 1810 having a skirt 1830, and a delivery catheter 1840. In each figure, skirt 1830 is shown engaging a surface of a tissue 1850. In the embodiments shown in FIGS. 17A and 17B, the relative sizes of the sleeves 1800, engagement catheters 1810, and delivery catheters 1840 are similar as shown, but the relative sizes of the skirts 1830 of the engagement catheters 1810 are clearly different. The exemplary embodiment of the portion of an apparatus for engaging a tissue shown in FIG. 17A comprises a skirt 1830 of the same or substantially similar relative size as the engagement catheter 1810, meaning that the diameters of the engagement catheter 1810 and the skirt 1830 shown in FIG. 17A are approximately the same. Conversely, the exemplary embodiment of the portion of an apparatus for engaging a tissue shown in FIG. 17B comprises a skirt 1830 notably larger than the engagement catheter 1810, meaning that the diameters of the engagement catheter 1810 and the skirt 1830 at its widest point shown in FIG. 17B are notably different. As shown in FIG. 17B, as skirt 1830 extends from engagement catheter 1810 to tissue 1850, the diameter of skirt 1830 increases. As such, skirt 1830 of the embodiment shown in FIG. 17B may engage a larger surface area of a tissue (shown by 1860) than the embodiment of the skirt 1830 shown in FIG. 17A. The ability to engage a larger surface area of a tissue 1850 by skirt 1830 allows a better reversible engagement of a tissue 1850 when a vacuum is provided as described in detail herein. This improved suction allows a person using such an apparatus to more effectively engage a tissue 1850 than would otherwise be possible when skirt 1830 engages a smaller surface area of a tissue.

FIGS. 18A and 18B show perspective views of an embodiment of a portion of an apparatus for engaging a tissue. FIG. 18A represents an embodiment whereby a skirt 1830 of an engagement catheter 1810 is positioned substantially within a sleeve 1800. FIG. 18B represents an embodiment whereby a skirt 1830 of an engagement catheter 1810 is positioned outside of s 1800. As such, the positioning of skirt 1830 within sleeve 1800 can be seen in the embodiments of FIGS. 16A and 18A, and the positioning of skirt 1830 outside of sleeve 1800 can be seen in the embodiments of FIGS. 16C and 18B.

As shown in FIG. 18A, skirt 1830 of engagement catheter 1810 is positioned within sleeve 1800, whereby the configuration of skirt 1830 is collapsed so that skirt 1830 may fit within sleeve 1800. As sleeve 1800 moves in the direction of the arrow shown in FIG. 18B, skirt 1830 becomes exposed and its configuration is allowed to expand because there are no constraints provided by the inner wall of sleeve 1800.

The embodiments shown in FIGS. 18A and 18B also show an exemplary embodiment of a configuration of an engagement catheter 1810. As shown in FIG. 18B, engagement catheter 1810 defines a number of apertures (representing lumens) present at the distal end of engagement catheter 1810 (at the proximal end of skirt 1830), including, but not limited to, one or more vacuum ports 1870 (representing the aperture at or near the distal end of a vacuum tube), and a delivery port 1880 (representing the aperture at or near the distal end of a delivery tube). A vacuum source (not shown) may be coupled to a suction port located at a proximal end of one or more vacuum tubes as described herein, whereby gas, fluid, and/or particulate(s) may be introduced into one or more vacuum ports 1870 by the introduction of a vacuum at a vacuum port. Gas, fluid, and/or particulate(s) may be introduced from delivery aperture 1880 to a tissue (not shown in FIG. 18A or 18B).

As shown by the exemplary embodiments of FIGS. 17A and 17B, the ability for a user of such an apparatus for engaging a tissue to obtain proper suction depends at least in part on the relative placement of skirt 1830 and delivery catheter 1840 at or near a tissue 1850. As described in detail herein regarding the exemplary embodiment shown in FIG. 5D, if a vacuum source provides suction through one or more vacuum ports 1870 (shown in FIGS. 18A and 18B), but skirt 1830 has not effectively engaged a tissue 1850, gas, fluid, and/or particulate(s) in the area of tissue 1850 and/or gas, fluid and/or particulate(s) delivered via delivery catheter 1840 to the area of tissue 1850 may be aspirated by one or more vacuum ports 1870. In a situation where skirt 1830 has effectively engaged a tissue 1850 but where delivery catheter 1840 has not engaged a tissue 1850, any gas, liquid, and/or particulate(s) delivered by delivery catheter 1840 may be aspirated by one or more vacuum ports 1870. In a situation where skirt 1830 and delivery catheter 1840 have effectively engaged a tissue 1850, most, if not all, of any gas, liquid, and/or particulate(s) delivered by delivery catheter 1840 to tissue 1850 would not be aspirated by one or more vacuum ports 1870 as the placement of delivery catheter 1840 on or within tissue 1850 would provide direct delivery at or within tissue 1850.

Figure 19:
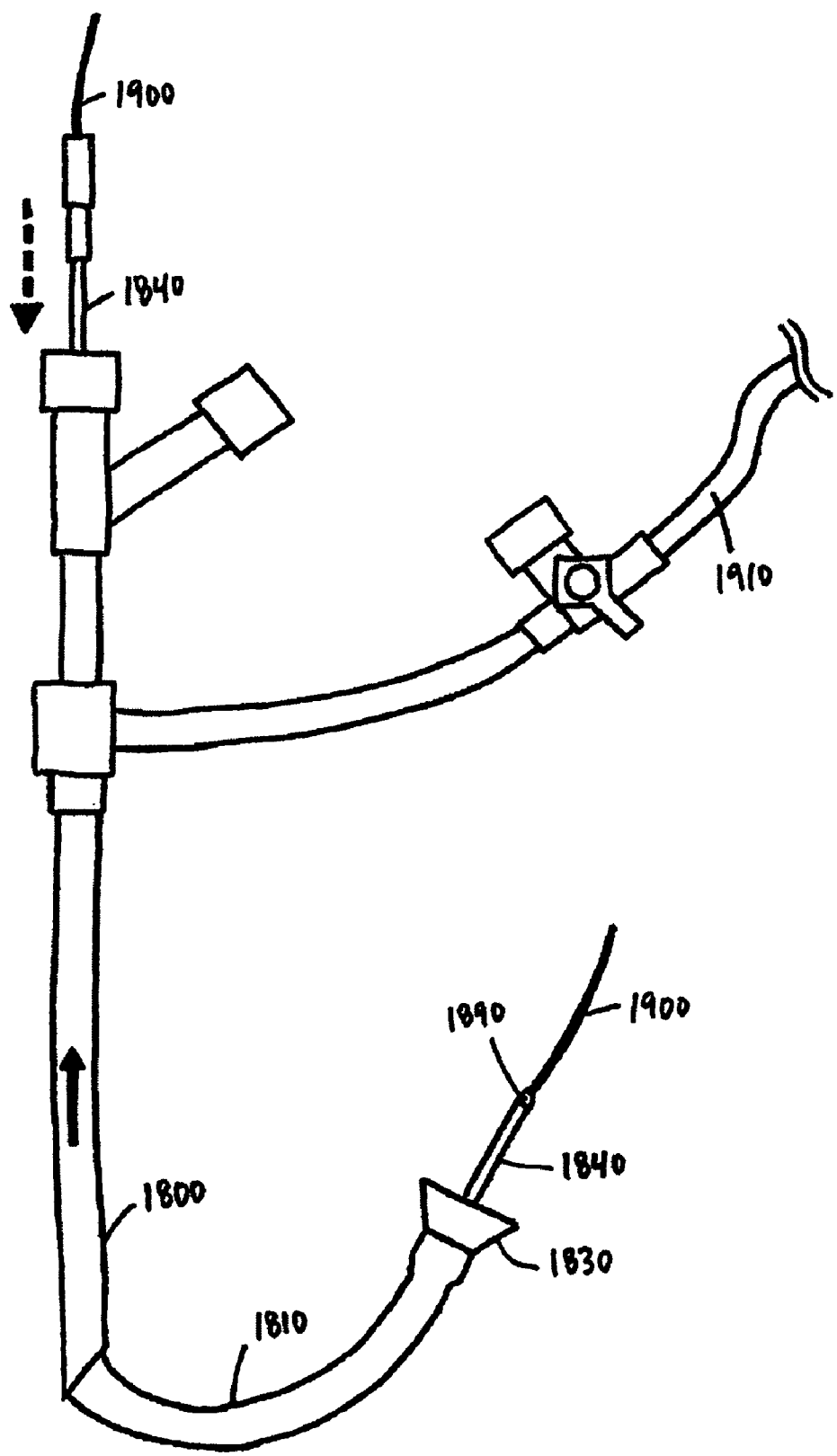
FIG. 19 shows an embodiment of a system for engaging a tissue, as disclosed herein.

An exemplary embodiment of a system and/or device for engaging a tissue as described herein is shown in FIG. 19. As shown in FIG. 19, an exemplary apparatus shows a sleeve 1800 which has been moved in the direction of the arrow to reveal skirt 1830 at the distal end of engagement catheter 1810, allowing skirt to resume an expanded, frusto-conical configuration. As shown in this embodiment, delivery catheter 1840 has been introduced at the proximal end of the apparatus (in the direction shown by the dashed arrow), allowing delivery catheter 1840 to exit out of a delivery lumen (not shown) at the distal end of engagement catheter 1840. A needle 1890 may be present at the distal end of delivery catheter 1840, facilitating the potential puncture of a tissue (not shown) to allow the distal end of delivery catheter 1840 to enter a tissue.

In addition, and as shown in the exemplary embodiment of FIG. 19, a lead 1900 may be introduced into delivery catheter 1840 (in the direction shown by the dashed arrow), whereby the distal end of lead 1900 may exit an aperture of needle 1890 and optionally enter a tissue and/or a lumen of a tissue. As described herein, any number of suitable types of leads 1900 may be used with the delivery catheters described herein, including sensing leads and/or pacing leads. A vacuum source 1910 may also provide a source of vacuum to such an apparatus to allow skirt 1830 to engage a tissue using suction.

The exemplary embodiment of an apparatus for engaging a tissue as shown in FIG. 19 comprises an engagement catheter 1810 having a curvature. Such a curved engagement catheter 1810 allows a user of such an apparatus, for example, to insert a portion of the apparatus into a body or tissue from one direction, and engage a tissue with skirt 1830, delivery catheter 1840, needle 1890, and/or lead 1900 from another direction. For example, a user may introduce a portion of an apparatus from one side of the heart, and the apparatus may engage the heart from a different direction than the direction of introduction of the apparatus.

It can also be appreciated that an exemplary embodiment of an apparatus of the present disclosure may be used to engage an internal portion of an organ. As previously referenced herein, such an apparatus may be used to engage the surface of a tissue. However, it can be appreciated that such a tissue may be an outer surface of any number of tissues, including, but not limited to, a heart, lungs, intestine, stomach, or any number of other organs or tissues. It can also be appreciated that some of these types of organs or tissues, including the heart for example, may have one or more internal tissue surfaces capable of being engaged by an apparatus of the present disclosure. For example, a user of such an apparatus may use the apparatus to engage the septum of the heart dividing one side of the heart from another. Such use may facilitate the delivery of a gas, liquid, and/or particulate(s) to a particular side of the heart, as such a targeted delivery may provide beneficial effects, including, but not limited to, the ability to deliver a lead to pace the inner wall of the left side of the heart.

Figure 20A:
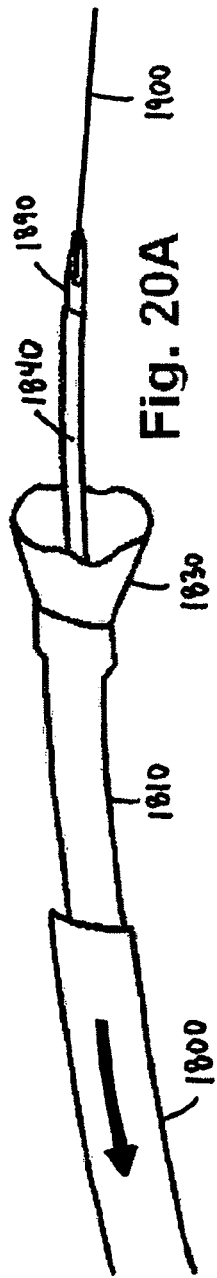
FIG. 20A shows an embodiment of a portion of an apparatus for engaging a tissue having a lead positioned therethrough, as disclosed herein.
Figure 20B:
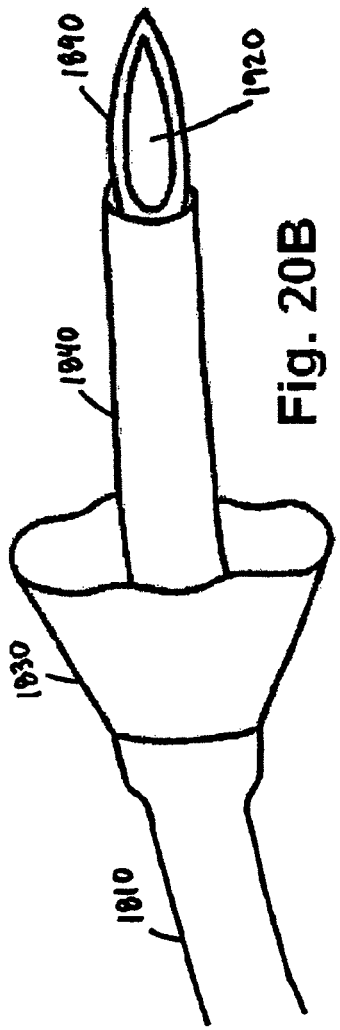
FIG. 20B shows an embodiment of a portion of an apparatus for engaging a tissue showing a needle, as disclosed herein.
Figure 20C:
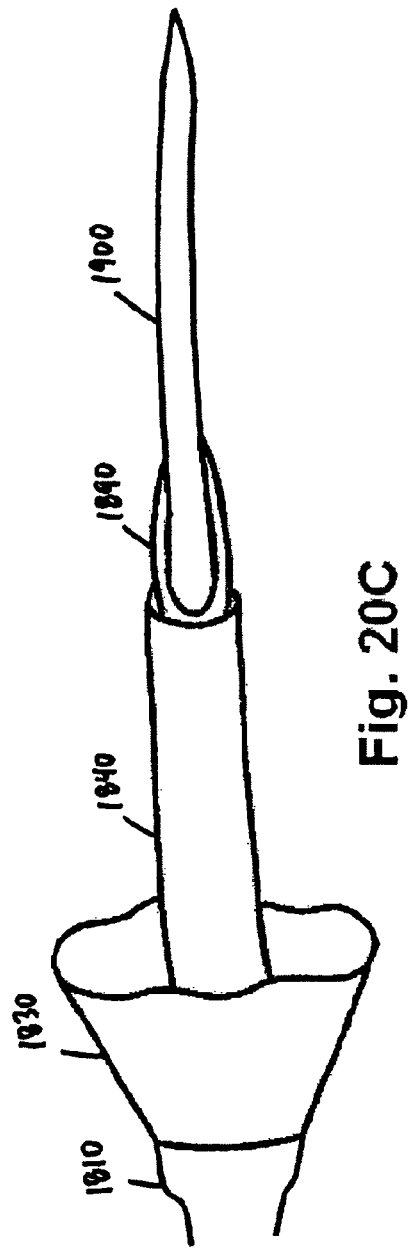
FIG. 20C shows the embodiment of FIG. 20B having a lead positioned therethrough.

Referring now to FIGS. 20A, 20B, and 20C, embodiments of a portion of an apparatus for engaging a tissue according to the present disclosure are shown. As shown in FIG. 20A, an exemplary embodiment of a portion of an apparatus for engaging a tissue comprises sleeve 1800 slidingly engaging engagement catheter 1810, and when sleeve 1800 is slid in the direction of the arrow shown, skirt 1830 is revealed, having an expanded, optionally frusto-conical configuration as shown. Delivery catheter 1840 may exit out of a delivery lumen (not shown), with needle 1890 present at the distal end of delivery catheter 1840. As shown in the embodiment of FIG. 20A, lead 1900 is present, exiting out of an aperture of needle 1890.

FIGS. 20B and 20C show a closer view of an embodiment of a portion of an apparatus for engaging a tissue according to the present disclosure than is shown in FIG. 20A. As shown in FIGS. 20B and 20C, aperture 1920 of needle 1890 is shown, and as shown in FIG. 20C, lead 1900 may exit aperture 1920 of needle 1890.

Referring now to FIGS. 5A, 5B, 5C, and 5D, there is shown another embodiment of an engagement catheter as disclosed herein. Engagement catheter 700 is an elongated tube having a proximal end 710 and a distal end 720, as well as two lumens 730, 740 extending between proximal end 710 and distal end 720. Lumens 730, 740 are formed by concentric inner wall 750 and outer wall 760, as particularly shown in FIGS. 5B and 5C. At proximal end 710, engagement catheter 700 includes a vacuum port 770, which is attached to lumen 730 so that a vacuum source can be attached to vacuum port 770 to create suction in lumen 730, thereby forming a suction channel. At distal end 720 of catheter 700, a suction port 780 is attached to lumen 730 so that suction port 780 can be placed in contact with heart tissue 775 (see FIG. 5D) for aspirating the tissue, thereby forming a vacuum seal between suction port 780 and tissue 775 when the vacuum source is attached and engaged. The vacuum seal enables suction port 780 to grip, stabilize, and retract tissue 775. For example, attaching a suction port to an interior atrial wall using a vacuum source enables the suction port to retract the atrial wall from the pericardial sac surrounding the heart, which enlarges the pericardial space between the atrial wall and the pericardial sac.

As shown in FIG. 5C, two internal lumen supports 810, 820 are located within lumen 730 and are attached to inner wall 750 and outer wall 760 to provide support to the walls. These lumen supports divide lumen 730 into two suction channels. Although internal lumen supports 810, 820 extend from distal end 720 of catheter 700 along a substantial portion of the length of catheter 700, internal lumen supports 810, 820 may or may not span the entire length of catheter 700. Indeed, as shown in FIGS. 5A, 5B, and 5C, internal lumen supports 810, 820 do not extend to proximal end 710 to ensure that the suction from the external vacuum source is distributed relatively evenly around the circumference of catheter 700. Although the embodiment shown in FIG. 5C includes two internal lumen supports, other embodiments may have just one internal support or even three or more such supports.

Figure 5D:
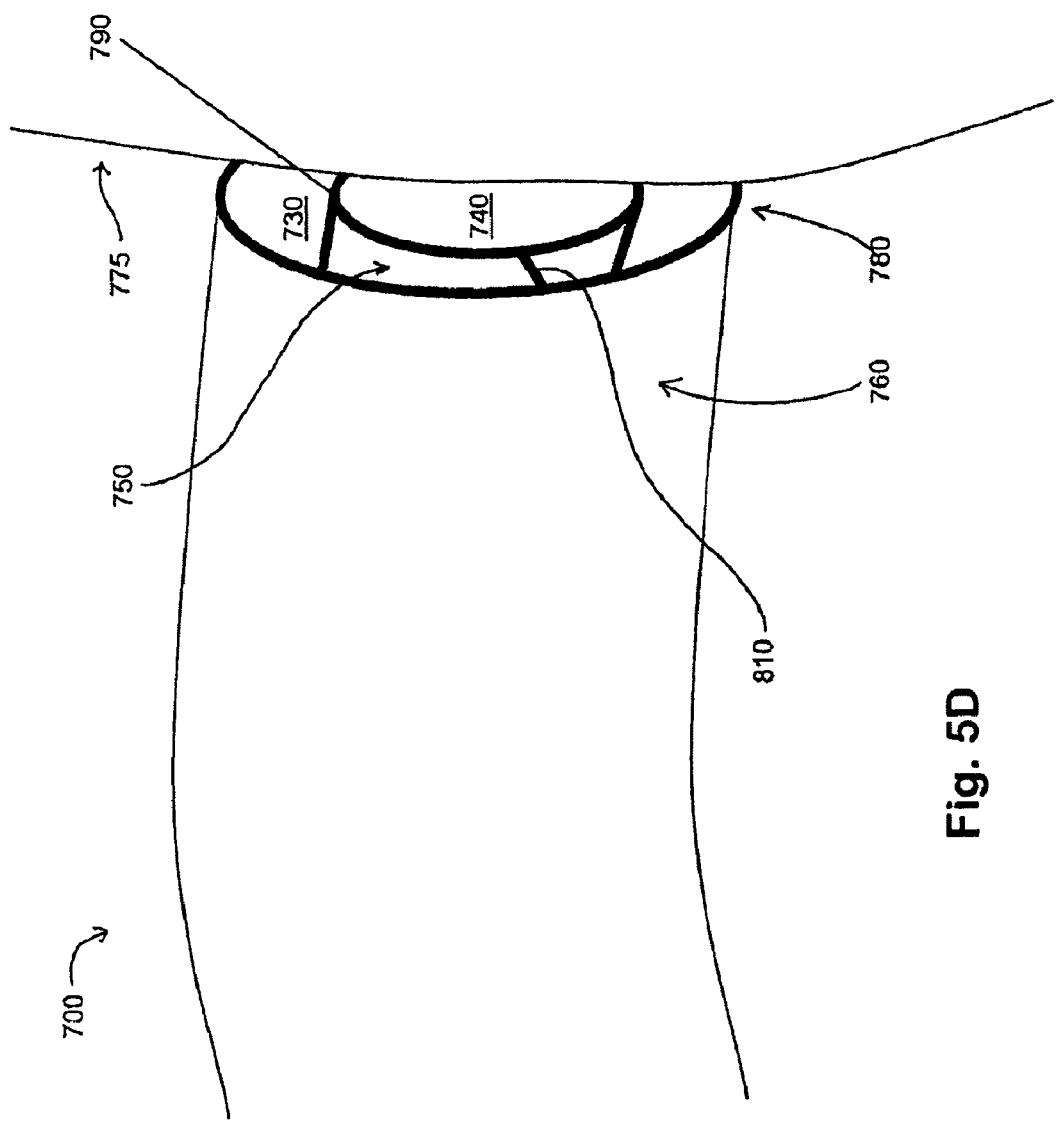
FIG. 5D shows the engagement catheter shown in FIG. 5A approaching a heart wall from inside of the heart.

FIG. 5D shows engagement catheter 700 approaching heart tissue 775 for attachment thereto. It is important for the clinician performing the procedure to know when the suction port has engaged the tissue of the atrial wall or the atrial appendage. For example, in reference to FIG. 5D, it is clear that suction port 780 has not fully engaged tissue 775 such that a seal is formed. However, because suction port 780 is not usually seen during the procedure, the clinician may determine when the proper vacuum seal between the atrial tissue and the suction port has been made by monitoring the amount of blood that is aspirated, by monitoring the suction pressure with a pressure sensor/regulator, or both. For example, as engagement catheter 700 approaches the atrial wall tissue (such as tissue 775) and is approximately in position, the suction can be activated through lumen 730. A certain level of suction (e.g., 10 mmHg) can be imposed and measured with a pressure sensor/regulator. As long as catheter 700 does not engage the wall, some blood will be aspirated into the catheter and the suction pressure will remain the same. However, when catheter 700 engages or attaches to the wall of the heart (depicted as tissue 775 in FIG. 5D), minimal blood is aspirated and the suction pressure will start to gradually increase. Each of these signs can alert the clinician (through alarm or other means) as an indication of engagement. The pressure regulator is then able to maintain the suction pressure at a preset value to prevent over-suction of the tissue.

An engagement catheter, such as engagement catheter 700, may be configured to deliver a fluid or other substance to tissue on the inside of a wall of the heart, including an atrial wall or a ventricle wall. For example, lumen 740 shown in FIGS. 5A and 5C includes an injection channel 790 at distal end 720. Injection channel 790 dispenses to the targeted tissue a substance flowing through lumen 740. As shown in FIG. 5D, injection channel 790 is the distal end of lumen 740. However, in other embodiments, the injection channel may be ring-shaped (see FIG. 2C) or have some other suitable configuration.

Substances that can be locally administered with an engagement catheter include preparations for gene or cell therapy, drugs, and adhesives that are safe for use in the heart. The proximal end of lumen 740 has a fluid port 800, which is capable of attachment to an external fluid source for supply of the fluid to be delivered to the targeted tissue. Indeed, after withdrawal of a needle from the targeted tissue, as discussed herein, an adhesive may be administered to the targeted tissue by the engagement catheter for sealing the puncture wound left by the needle withdrawn from the targeted tissue.

Referring now to FIGS. 6A, 6B, and 6C, there is shown a delivery catheter 850 comprising an elongated hollow tube 880 having a proximal end 860, a distal end 870, and a lumen 885 along the length of the catheter. Extending from distal end 870 is a hollow needle 890 in communication with lumen 885. Needle 890 is attached to distal end 870 in the embodiment of FIGS. 6A, 6B, and 6C, but, in other embodiments, the needle may be removably attached to, or otherwise located at, the distal end of the catheter (see FIG. 1A). In the embodiment shown in FIGS. 6A, 6B, and 6C, as in certain other embodiments having an attached needle, the junction (i.e., site of attachment) between hollow tube 880 and needle 890 forms a security notch 910 circumferentially around needle 890 to prevent needle 890 from over-perforation. Thus, when a clinician inserts needle 890 through an atrial wall to gain access to the pericardial space, the clinician will not, under normal conditions, unintentionally perforate the pericardial sac with needle 890 because the larger diameter of hollow tube 880 (as compared to that of needle 890) at security notch 910 hinders further needle insertion. Although security notch 910 is formed by the junction of hollow tube 880 and needle 890 in the embodiment shown in FIGS. 6A, 6B, and 6C, other embodiments may have a security notch that is configured differently. For example, a security notch may include a band, ring, or similar device that is attached to the needle a suitable distance from the tip of the needle. Like security notch 910, other security notch embodiments hinder insertion of the needle past the notch itself by presenting a larger profile than the profile of the needle such that the notch does not easily enter the hole in the tissue caused by entry of the needle.

It is useful for the clinician performing the procedure to know when the needle has punctured the atrial tissue. This can be done in several ways. For example, the delivery catheter can be connected to a pressure transducer to measure pressure at the tip of the needle. Because the pressure is lower and much less pulsatile in the pericardial space than in the atrium, the clinician can recognize immediately when the needle passes through the atrial tissue into the pericardial space.

Alternatively, as shown in FIG. 6B, needle 890 may be connected to a strain gauge 915 as part of the catheter assembly. When needle 890 contacts tissue (not shown), needle 890 will be deformed. The deformation will be transmitted to strain gauge 915 and an electrical signal will reflect the deformation (through a classical wheatstone bridge), thereby alerting the clinician. Such confirmation of the puncture of the wall can prevent over-puncture and can provide additional control of the procedure.

In some embodiments, a delivery catheter, such as catheter 850 shown in FIGS. 6A, 6B, and 6C, is used with an engagement catheter, such as catheter 700 shown in FIGS. 5A, 5B, 5C, and 5D, to gain access to the pericardial space between the heart wall and the pericardial sac. For example, engagement catheter 700 may be inserted into the vascular system and advanced such that the distal end of the engagement catheter is within the atrium. The engagement catheter may be attached to the targeted tissue on the interior of a wall of the atrium using a suction port as disclosed herein. A standard guide wire may be inserted through the lumen of the delivery catheter as the delivery catheter is inserted through the inner lumen of the engagement catheter, such as lumen 740 shown in FIGS. 5B and 5C. Use of the guide wire enables more effective navigation of the delivery catheter 850 and prevents the needle 890 from damaging the inner wall 750 of the engagement catheter 700. When the tip of the delivery catheter with the protruding guide wire reaches the atrium, the wire is pulled back, and the needle is pushed forward to perforate the targeted tissue. The guide wire is then advanced through the perforation into the pericardial space, providing access to the pericardial space through the atrial wall.

Referring again to FIGS. 6A, 6B, and 6C, lumen 885 of delivery catheter 850 may be used for delivering fluid into the pericardial space after needle 890 is inserted through the atrial wall or the atrial appendage. After puncture of the wall or appendage, a guide wire (not shown) may be inserted through needle lumen 900 into the pericardial space to maintain access through the atrial wall or appendage. Fluid may then be introduced to the pericardial space in a number of ways. For example, after the needle punctures the atrial wall or appendage, the needle is generally withdrawn. If the needle is permanently attached to the delivery catheter, as in the embodiment shown in FIGS. 6A and 6B, then delivery catheter 850 would be withdrawn and another delivery catheter (without an attached needle) would be introduced over the guide wire into the pericardial space. Fluid may then be introduced into the pericardial space through the lumen of the second delivery catheter.

In some embodiments, however, only a single delivery catheter is used. In such embodiments, the needle is not attached to the delivery catheter, but instead may be a needle wire (see FIG. 1A). In such embodiments, the needle is withdrawn through the lumen of the delivery catheter, and the delivery catheter may be inserted over the guide wire into the pericardial space. Fluid is then introduced into the pericardial space through the lumen of the delivery catheter.

The various embodiments disclosed herein may be used by clinicians, for example: (1) to deliver genes, cells, drugs, etc.; (2) to provide catheter access for epicardial stimulation; (3) to evacuate fluids acutely (e.g., in cases of pericardial tampondae) or chronically (e.g., to alleviate effusion caused by chronic renal disease, cancer, etc.); (4) to perform transeptal puncture and delivery of a catheter through the left atrial appendage for electrophysiological therapy, biopsy, etc.; (5) to deliver a magnetic glue or ring through the right atrial appendage to the aortic root to hold a percutaneous aortic valve in place; (6) to deliver a catheter for tissue ablation, e.g., to the pulmonary veins, or right atrial and epicardial surface of the heart for atrial and ventricular arrythmias; (7) to deliver and place epicardial, right atrial, and right and left ventricle pacing leads (as discussed herein); (8) to occlude the left atrial appendage through percutaneous approach; and (9) to visualize the pericardial space with endo-camera or scope to navigate the epicardial surface of the heart for therapeutic delivery, diagnosis, lead placement, mapping, etc. Many other applications, not explicitly listed here, are also possible and within the scope of the present disclosure.

Figure 7:
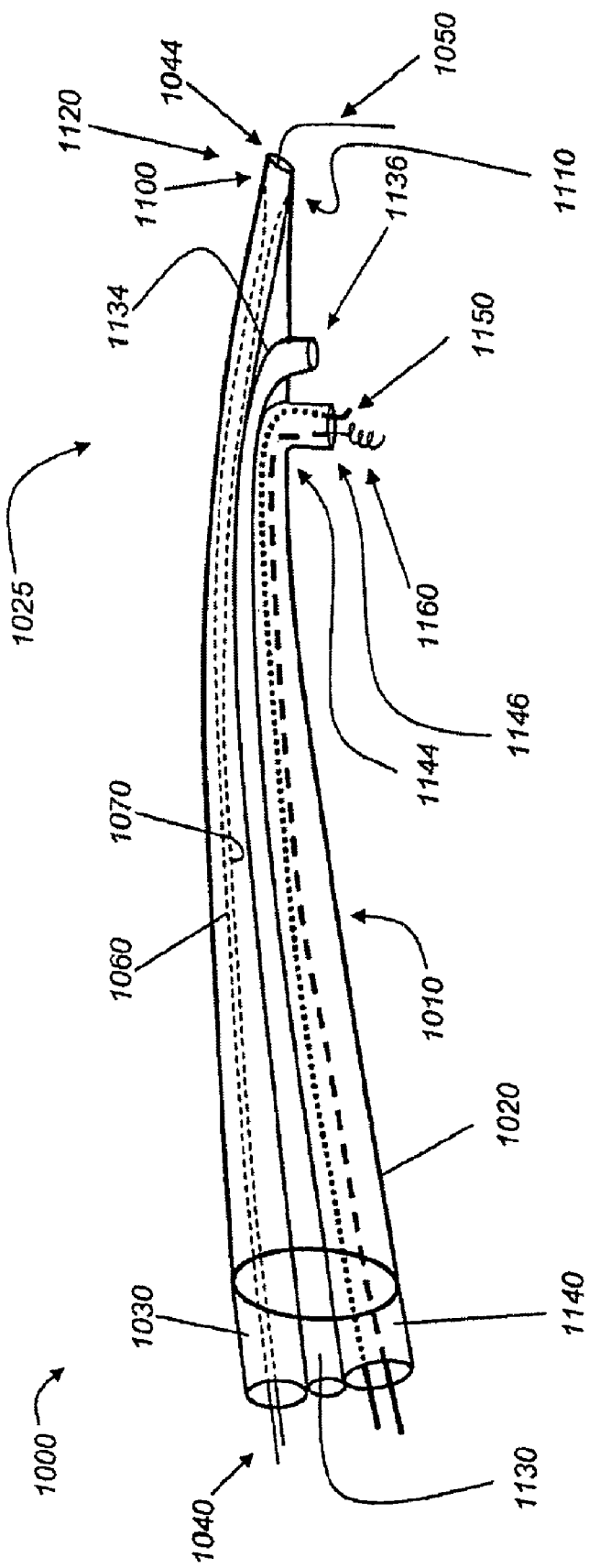
FIG. 7 shows an embodiment of a delivery catheter as disclosed herein.

Referring now to FIG. 7, there is shown a delivery catheter 1000. Delivery catheter 1000 includes an elongated tube 1010 having a wall 1020 extending from a proximal end (not shown) of tube 1010 to a distal end 1025 of tube 1010. Tube 1010 includes two lumens, but other embodiments of delivery catheters may have fewer than, or more than, two lumens, depending on the intended use of the delivery catheter. Tube 1010 also includes a steering channel 1030, in which a portion of steering wire system 1040 is located. Steering channel 1030 forms orifice 1044 at distal end 1025 of tube 1010 and is sized to fit over a guide wire 1050.

Figure 8:
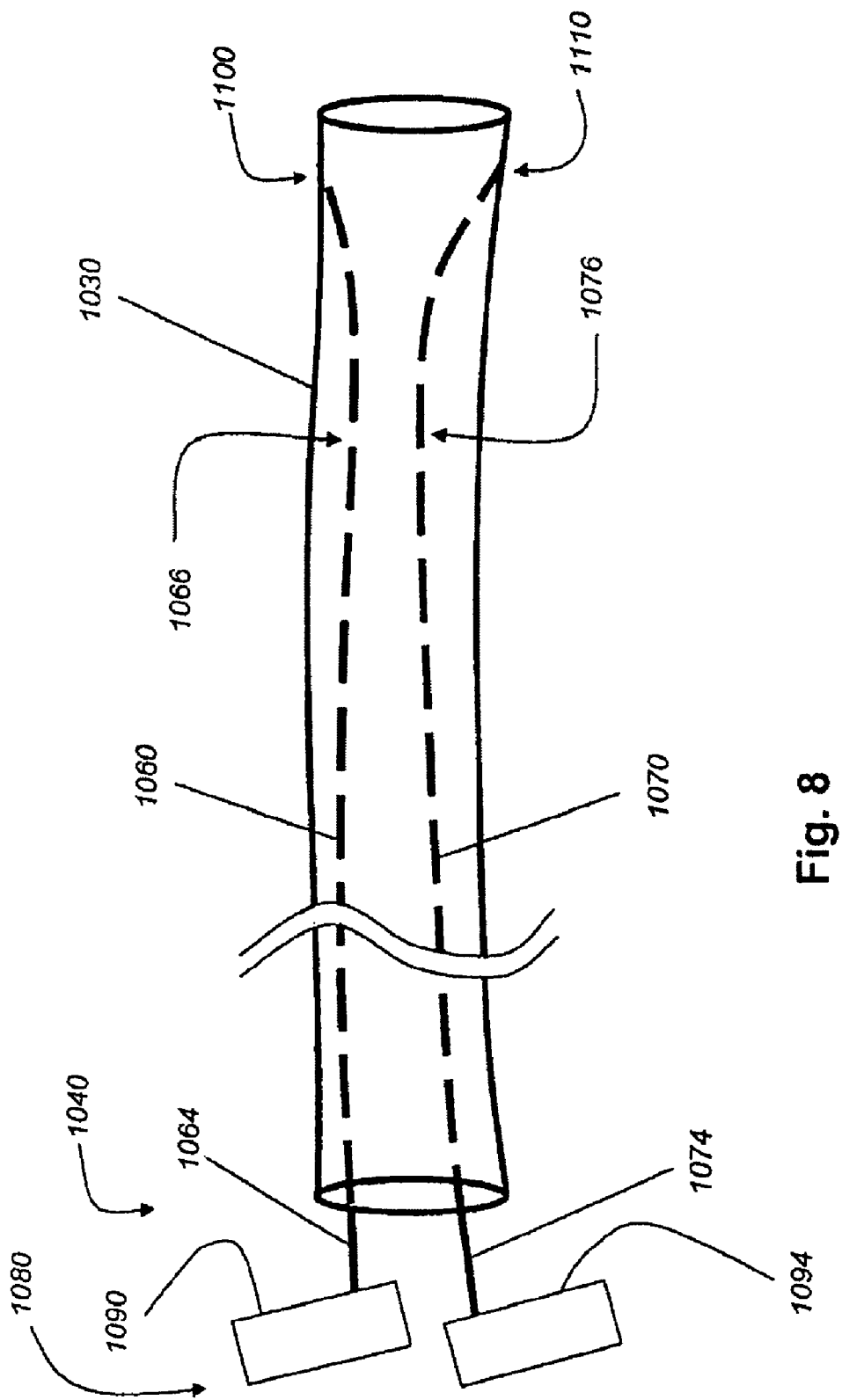
FIG. 8 shows an embodiment of a steering wire system within a steering channel.

FIG. 8 shows in more detail steering wire system 1040 within steering channel 1030 (which is shown cut away from the remainder of the delivery catheter). Steering wire system 1040 is partially located in steering channel 1030 and comprises two steering wires 1060 and 1070 and a controller 1080, which, in the embodiment shown in FIG. 8, comprises a first handle 1090 and a second handle 1094. First handle 1090 is attached to proximal end 1064 of steering wire 1060, and second handle 1094 is attached to proximal end 1074 of steering wire 1070. Distal end 1066 of steering wire 1060 is attached to the wall of the tube of the delivery catheter within steering channel 1030 at attachment 1100, and distal end 1076 of steering wire 1070 is attached to the wall of the tube of the delivery catheter within steering channel 1030 at attachment 1110. As shown in FIG. 7, attachment 1100 and attachment 1110 are located on opposing sides of steering channel 1030 near distal tip 1120 of delivery catheter 1000.

Figure 11:
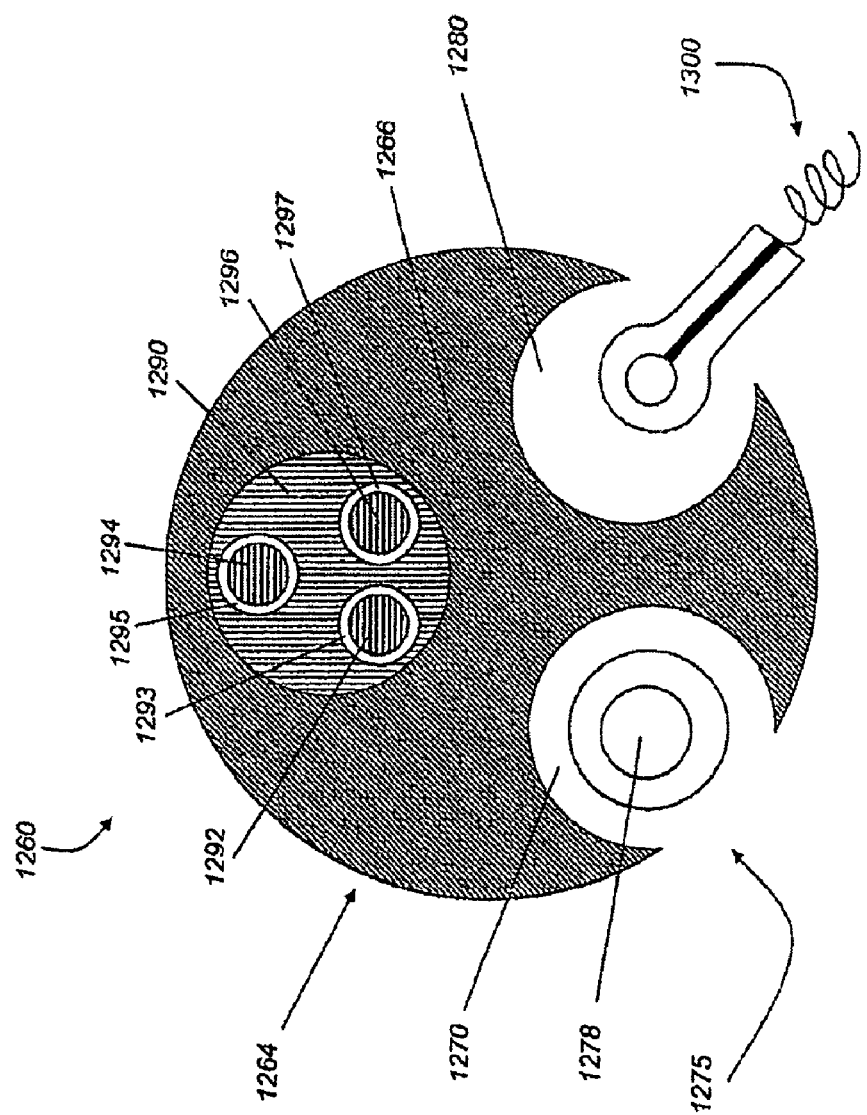
FIG. 11 shows a cross-sectional view of another embodiment of a delivery catheter as disclosed herein.

In the embodiment of FIG. 8, steering wires 1060 and 1070 are threaded as a group through steering channel 1030. However, the steering wire systems of other embodiments may include steering wires that are individually threaded through smaller lumens within the steering channel. For example, FIG. 11 shows a cross-sectional view of a delivery catheter 1260 having an elongated tube 1264 comprising a wall 1266, a steering channel 1290, a first lumen 1270, and a second lumen 1280. Delivery catheter 1260 further includes a steering wire 1292 within a steering wire lumen 1293, a steering wire 1294 within a steering wire lumen 1295, and a steering wire 1296 within a steering wire lumen 1297. Each of steering wire lumens 1293, 1295, and 1297 is located within steering channel 1290 and is formed from wall 1266. Each of steering wires 1292, 1294, and 1296 is attached to wall 1266 within steering channel 1290. As will be explained, the attachment of each steering wire to the wall may be located near the distal tip of the delivery catheter, or may be located closer to the middle of the delivery catheter.

Referring now to FIGS. 7 and 8, steering wire system 1040 can be used to control distal tip 1120 of delivery catheter 1000. For example, when first handle 1090 is pulled, steering wire 1060 pulls distal tip 1120, which bends delivery catheter 1000, causing tip deflection in a first direction. Similarly, when second handle 1094 is pulled, steering wire 1070 pulls distal tip 1120 in the opposite direction, which bends delivery catheter 1000, causing tip deflection in the opposite direction. Thus, delivery catheter 1000 can be directed (i.e., steered) through the body using steering wire system 1040.

Although steering wire system 1040 has only two steering wires, other embodiments of steering wire systems may have more than two steering wires. For example, some embodiments of steering wire systems may have three steering wires (see FIG. 11), each of which is attached to the steering channel at a different attachment. Other embodiments of steering wire systems may have four steering wires. Generally, more steering wires give the clinician more control for directing the delivery catheter because each additional steering wire enables the user to deflect the tip of the delivery catheter in an additional direction. For example, four steering wires could be used to direct the delivery catheter in four different directions (e.g., up, down, right, and left).

If a steering wire system includes more than two steering wires, the delivery catheter may be deflected at different points in the same direction. For instance, a delivery catheter with three steering wires may include two steering wires for deflection in a certain direction and a third steering wire for reverse deflection (i.e., deflection in the opposite direction). In such an embodiment, the two steering wires for deflection are attached at different locations along the length of the delivery catheter. Referring now to FIGS. 9A-9C, there is shown a steering wire system 1350 within steering channel 1360 (which is shown cut away from the remainder of the delivery catheter) in different states of deflection. Steering wire system 1350 is partially located in steering channel 1360 and comprises three steering wires 1370, 1380, and 1390 and a controller 1400, which, in the embodiment shown in FIGS. 9A-9C, comprises a handle 1410. Handle 1410 is attached to proximal end 1374 of steering wire 1370, proximal end 1384 of steering wire 1380, and proximal end 1394 of steering wire 1390. Distal end 1376 of steering wire 1370 is attached to the wall of the tube of the delivery catheter within steering channel 1360 at attachment 1378, which is near the distal tip of the delivery catheter (not shown). Distal end 1386 of steering wire 1380 is attached to the wall of the tube of the delivery catheter within steering channel 1360 at attachment 1388, which is near the distal tip of the delivery catheter (not shown). Attachment 1378 and attachment 1388 are located on opposing sides of steering channel 1360 such that steering wires 1370 and 1380, when tightened (as explained below), would tend to deflect the delivery catheter in opposite directions. Distal end 1396 of steering wire 1390 is attached to the wall of the tube of the delivery catheter within steering channel 1360 at attachment 1398, which is located on the delivery catheter at a point closer to the proximal end of the delivery catheter than attachments 1378 and 1388. Attachment 1398 is located on the same side of steering channel 1360 as attachment 1388, such that steering wires 1380 and 1390, when tightened (as explained below), would tend to deflect the delivery catheter in the same direction. However, because attachment 1398 is closer to the proximal end of the delivery catheter than is attachment 1388, the tightening of steering wire 1390 tends to deflect the delivery catheter at a point closer to the proximal end of the delivery catheter than does the tightening of steering wire 1380. Thus, as shown in FIG. 9A, the tightening of steering wire 1390 causes a deflection in the delivery catheter approximately at point 1410. The tightening of steering wire 1380 at the same time causes a further deflection in the delivery catheter approximately at point 1420, as shown in FIG. 9B. The tightening of steering wire 1370, therefore, causes a reverse deflection, returning the delivery catheter to its original position (see FIG. 9C).

Referring again to FIG. 7, elongated tube 1010 further includes lumen 1130 and lumen 1140. Lumen 1130 extends from approximately the proximal end (not shown) of tube 1010 to or near distal end 1025 of tube 1010. Lumen 1130 has a bend 1134, relative to tube 1010, at or near distal end 1025 of tube 1010 and an outlet 1136 through wall 1020 of tube 1010 at or near distal end 1025 of tube 1010. Similarly, lumen 1140 has a bend 1144, relative to tube 1010, at or near distal end 1025 of tube 1010 and an outlet 1146 through wall 1020 of tube 1010 at or near distal end 1025 of tube 1010. In the embodiment shown in FIG. 7, lumen 1130 is configured as a laser Doppler tip, and lumen 1140 is sized to accept a retractable sensing lead 1150 and a pacing lead 1160 having a tip at the distal end of the lead. The fiberoptic laser Doppler tip detects and measures blood flow (by measuring the change in wavelength of light emitted by the tip), which helps the clinician to identify—and then avoid—blood vessels during lead placement. Sensing lead 1150 is designed to detect electrical signals in the heart tissue so that the clinician can avoid placing a pacing lead into electrically nonresponsive tissue, such as scar tissue. Pacing lead 1160 is a screw-type lead for placement onto the cardiac tissue, and its tip, which is an electrode, has a substantially screw-like shape. Pacing lead 1160 is capable of operative attachment to a CRT device (not shown) for heart pacing. Although lead 1160 is used for cardiac pacing, any suitable types of leads may be used with the delivery catheters described herein, including sensing leads.

Each of bend 1134 of lumen 1130 and bend 1144 of lumen 1140 forms an approximately 90-degree angle, which allows respective outlets 1136 and 1146 to face the external surface of the heart as the catheter is maneuvered in the pericardial space. However, other embodiments may have bends forming other angles, smaller or larger than 90-degrees, so long as the lumen provides proper access to the external surface of the heart from the pericardial space. Such angles may range, for example, from about 25-degrees to about 155-degrees. In addition to delivering leads and Doppler tips, lumen 1130 and lumen 1140 may be configured to allow, for example, the taking of a cardiac biopsy, the delivery of gene cell treatment or pharmacological agents, the delivery of biological glue for ventricular reinforcement, implementation of ventricular epicardial suction in the acute myocardial infarction and border zone area, the removal of fluid in treatment of pericardial effusion or cardiac tamponade, or the ablation of cardiac tissue in treatment of atrial fibrillation.

For example, lumen 1130 could be used to deliver a catheter needle for intramyocardial injection of gene cells, stems, biomaterials, growth factors (such as cytokinase, fibroblast growth factor, or vascular endothelial growth factor) and/or biodegradable synthetic polymers, RGD-liposome biologic glue, or any other suitable drug or substance for treatment or diagnosis. For example, suitable biodegradable synthetic polymer may include polylactides, polyglycolides, polycaprolactones, polyanhydrides, polyamides, and polyurethanes. In certain embodiments, the substance comprises a tissue inhibitor, such as a metalloproteinase (e.g., metalloproteinase 1).

The injection of certain substances (such as biopolymers and RGD-liposome biologic glue) is useful in the treatment of chronic heart failure to reinforce and strengthen the left ventricular wall. Thus, using the embodiments disclosed herein, the injection of such substances into the cardiac tissue from the pericardial space alleviates the problems and risks associated with delivery via the transthoracic approach. For instance, once the distal end of the delivery catheter is advanced to the pericardial space, as disclosed herein, a needle is extended through a lumen of the delivery catheter into the cardiac tissue and the substance is injected through the needle into the cardiac tissue.

The delivery of substances into the cardiac tissue from the pericardial space can be facilitated using a laser Doppler tip. For example, when treating ventricular wall thinning, the laser Doppler tip located in lumen 1140 of the embodiment shown in FIG. 7 can be used to measure the thickness of the left ventricular wall during the procedure (in real time) to determine the appropriate target area for injection.

Figure 10:
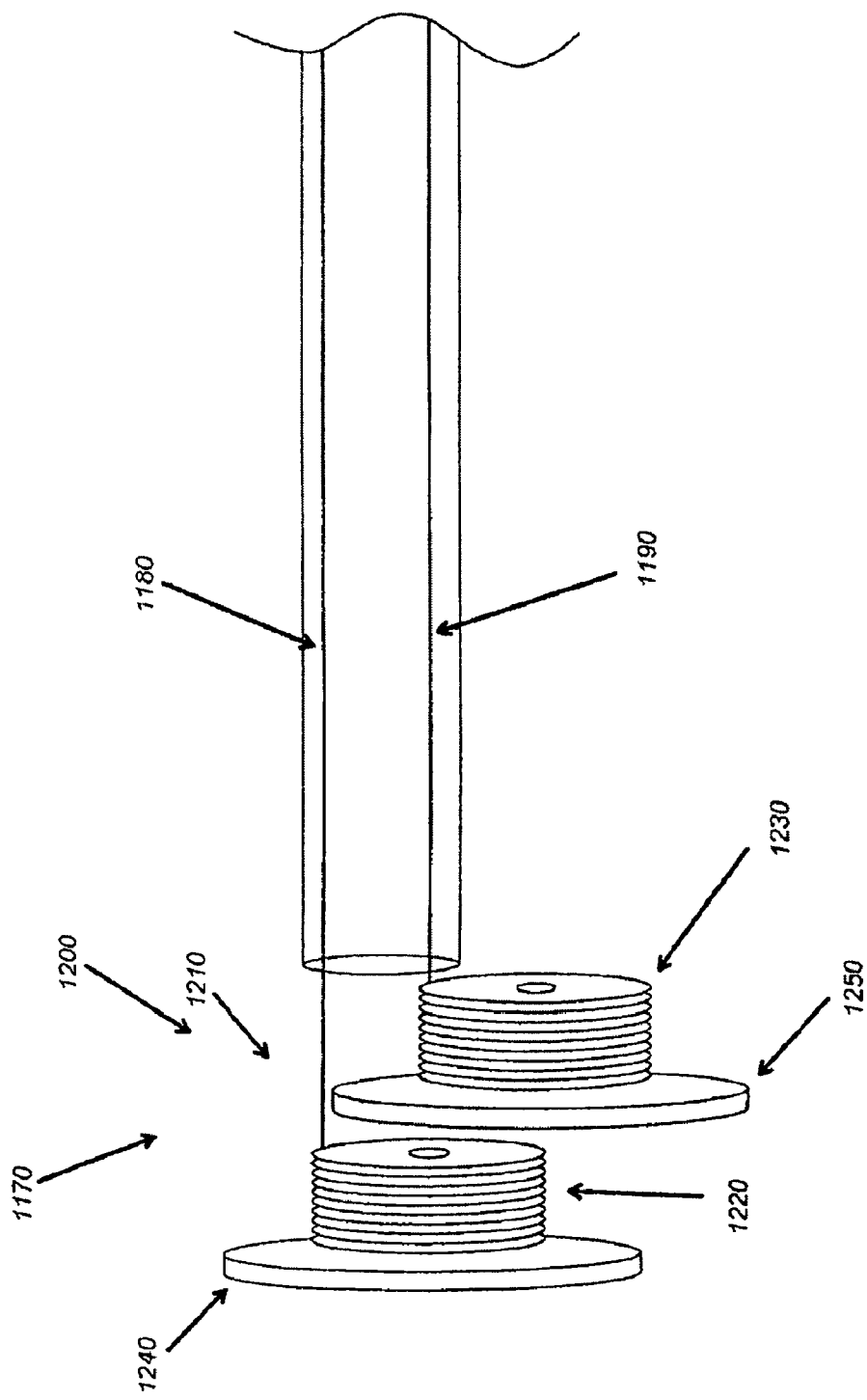
FIG. 10 shows a portion of another embodiment of a steering wire system.

Referring again to FIG. 8, although controller 1080 comprises first handle 1090 and second handle 1094, other embodiments of the controller may include different configurations. For example, instead of using handles, a controller may include any suitable torque system for controlling the steering wires of the steering wire system. Referring now to FIG. 10, there is shown a portion of a steering wire system 1170 having steering wire 1180, steering wire 1190, and controller 1200. Controller 1200 comprises a torque system 1210 having a first rotatable spool 1220, which is capable of collecting and dispensing steering wire 1180 upon rotation. For example, when first rotatable spool 1220 rotates in a certain direction, steering wire 1180 is collected onto spool 1220, thereby tightening steering wire 1180. When spool 1220 rotates in the opposite direction, steering wire 1180 is dispensed from spool 1220, thereby loosening steering wire 1180. Torque system 1210 also has a second rotatable spool 1230, which is capable of collecting and dispensing steering wire 1190 upon rotation, as described above.

Torque system 1210 further includes a first rotatable dial 1240 and a second rotatable dial 1250. First rotatable dial 1240 is attached to first rotatable spool 1220 such that rotation of first rotatable dial 1240 causes rotation of first rotatable spool 1220. Similarly, second rotatable dial 1250 is attached to second rotatable spool 1230 such that rotation of second rotatable dial 1250 causes rotation of second rotatable spool 1230. For ease of manipulation of the catheter, torque system 1210, and specifically first and second rotatable dials 1240 and 1250, may optionally be positioned on a catheter handle (not shown) at the proximal end of tube 1010.

Steering wire system 1170 can be used to direct a delivery catheter through the body in a similar fashion as steering wire system 1140. Thus, for example, when first rotatable dial 1240 is rotated in a first direction (e.g., clockwise), steering wire 1180 is tightened and the delivery catheter is deflected in a certain direction. When first rotatable dial 1240 is rotated in the other direction (e.g., counterclockwise), steering wire 1180 is loosened and the delivery catheter straightens to its original position. When second rotatable dial 1250 is rotated in one direction (e.g., counterclockwise), steering wire 1190 is tightened and the delivery catheter is deflected in a direction opposite of the first deflection. When second rotatable dial 1250 is rotated in the other direction (e.g., clockwise), steering wire 1190 is loosened and the delivery catheter is straightened to its original position.

Certain other embodiments of steering wire system may comprise other types of torque system, so long as the torque system permits the clinician to reliably tighten and loosen the various steering wires. The magnitude of tightening and loosening of each steering wire should be controllable by the torque system.

Referring again to FIG. 11, there is shown a cross-sectional view of delivery catheter 1260. Delivery catheter 1260 includes tube 1265, a first lumen 1270, a second lumen 1280, and a steering channel 1290. Steering wires 1292, 1294, and 1296 are shown within steering channel 1290. First lumen 1270 has outlet 1275, which can be used to deliver a microcamera system (not shown) or a laser Doppler tip 1278. Second lumen 1280 is sized to deliver a pacing lead 1300, as well as a sensing lead (not shown).

Treatment of cardiac tamponade, by the removal of a pericardial effusion, may be accomplished using an apparatus of the present disclosure as described below. A typical procedure would involve the percutaneous intravascular insertion of a portion of an apparatus into a body, which can be performed under local or general anesthesia. A portion of the apparatus may then utilize an approach described herein or otherwise known by a user of the apparatus to enter the percutaneous intravascular pericardial sac. It can be appreciated that such an apparatus may be used to access other spaces within a body to remove fluid and/or deliver a gas, liquid, and/or particulate(s) as described herein, and that such an apparatus is not limited to heart access and removal of pericardial effusions.

Exemplary embodiments of a portion of such an apparatus are shown in FIGS. 21A and 21B. As shown in FIG. 21A, a perforated drainage catheter 2100 is provided. Perforated drainage catheter 2100 comprises a tube defining at least one suction/infusion aperture 2110, and as shown in the embodiment in FIG. 21A, perforated drainage catheter 2100 defines multiple suction/infusion apertures 2110. Suction/infusion apertures 2110 are operably connected to an internal lumen defined within perforated delivery catheter 2100. It can be appreciated that the portion of perforated drainage catheter 2100 as shown in FIGS. 21A and 21B may be coupled to one or more portions of a system for engaging a tissue as described herein. As such, one or more portions of a system for engaging a tissue may be used to define a system for removing fluid as described herein.

It can be appreciated that the internal lumen within perforated delivery catheter 2100 may define multiple internal channels. For example, perforated delivery catheter 2100 may define two channels, one channel operably coupled to one or more suction/infusion apertures 2110 to allow for a vacuum source coupled to one end of the channel to provide suction via the suction/infusion apertures 2110, and one channel operably coupled to one or more other suction/infusion channels to allow for the injection of gas, liquid, and/or particulate(s) to a target site.

As described in further detail below, when perforated drainage catheter 2100 enters a space in a body, for example a pericardial sac, perforated drainage catheter 2100 may be used to remove fluid by the use of suction through one or more suction/infusion apertures 2110. Perforated drainage catheter 2100 may also be used to deliver gas, liquid, and/or particulate(s) to a target site through one or more suction/infusion apertures 2110.

Another exemplary embodiment of a portion of a perforated drainage catheter 2100 is shown in FIG. 21B. As shown in FIG. 21B, perforated drainage catheter 2100 comprises a tube with multiple suction/infusion apertures 2110. However, in this exemplary embodiment, perforated drainage catheter 2100 comprises a number of concave grooves 2120 extending a portion of a length of perforated drainage catheter 2100, whereby the suction/infusion apertures 2110 are provided at the recessed portions therein. Concave grooves 2120, when positioned at least partially around the circumference of perforated drainage catheter 2100, define one or more ridges 2130 extending a portion of a length of perforated drainage catheter 2100. Said ridges 2130 of perforated drainage catheter 2100, when positioned at or near a tissue (not shown), aid to prevent a tissue from coming in direct contact with one or more suction/infusion apertures 2110. For example, when perforated drainage catheter 2100 is used in a manner described herein and when a vacuum is coupled to perforated drainage catheter 2100, suction from one or more suction/infusion apertures 2110 positioned within one or more concave grooves 2120 would allow for the removal of fluid present in the area of perforated drainage catheter 2100. Ridges 2130 would aid to prevent or minimize tissue adhesion and/or contact with the one or more suction/infusion apertures 2110.

A procedure using perforated drainage catheter 2100 may be performed by inserting perforated drainage catheter 2100 into a pericardial sac, following the cardiac surface using, for example, fluoroscopy and/or echodoppler visualization techniques. When perforated drainage catheter 2100 is inserted into a pericardial sac, a pericardial effusion present within the pericardial sac, may be removed by, for example, gentle suction using a syringe. In one example, a 60 cc syringe may be used to remove the effusion with manual gentle suction. When the effusion has been removed, the patients hemodynamic parameters may be monitored to determine the effectiveness of the removal of the effusion. When the pericardial sac is empty, determined by, for example, fluoroscopy or echodoppler visualization, the acute pericardial effusion catheter may be removed, or it may be used for local treatment to introduce, for example, an antibiotic, chemotherapy, or another drug as described below.

Figure 22:
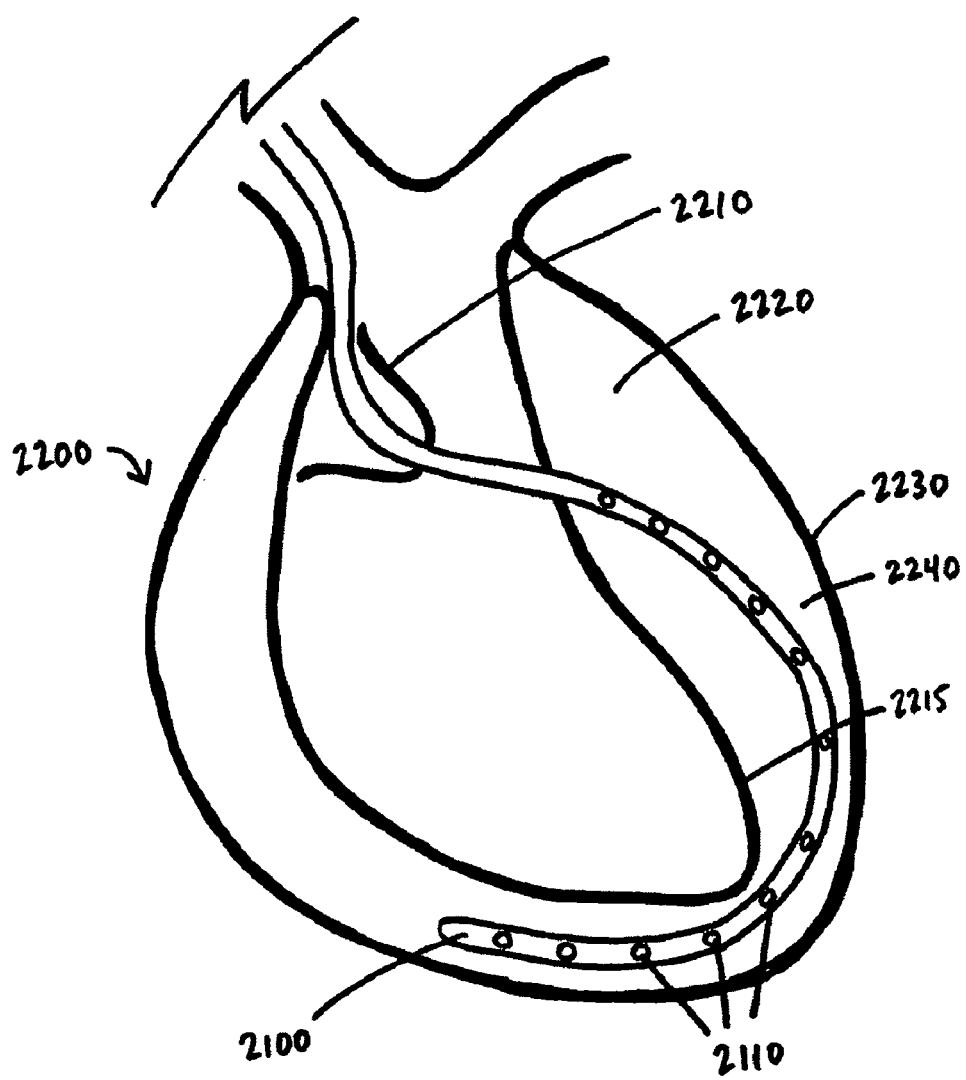
FIG. 22 shows an embodiment of a portion of an apparatus for removing fluid from a tissue inserted within a heart, as disclosed herein.

An exemplary embodiment of a portion of a perforated drainage catheter 2100 present within a pericardial sac is shown in FIG. 22. As shown in FIG. 22, perforated drainage catheter 2100 is first inserted into the heart 2200 using one or more of the techniques and/or procedures described herein, and is placed through the right atrial appendage 2210, the visceral pericardium 2215, and into the pericardial sac 2220. The outer portion of the pericardial sac 2220 is defined by the parietal pericardium 2230. A pericardial effusion 2240 (fluid within the pericardial sac 2220) may then be removed using perforated drainage catheter 2100. When a vacuum source (not shown) is coupled to the proximal end of a portion of a system for removing fluid (comprising, in part, perforated drainage catheter 2100 and one or more other components of a system for engaging a tissue as described herein), the introduction of a vacuum to perforated drainage catheter 2100 allows the pericardial effusion 2240 (the fluid) to be withdrawn from the pericardial sac 2220 into one or more suction/infusion apertures 2110 defined along a length of suction/infusion apertures 2110.

When perforated drainage catheter 2100 is used to remove some or all of a pericardial effusion (or other fluid present within a space within a body), it may also be used to deliver a gas, liquid, and/or particulate(s) at or near the space where the fluid was removed. For example, the use of perforated drainage catheter 2100 to remove a pericardial effusion may increase the risk of infection. As such, perforated drainage catheter 2100 may be used to rinse the pericardial sac (or other space present within a body) with water and/or any number of beneficial solutions, and may also be used to deliver one or more antibiotics to provide an effective systemic antibiotic therapy for the patient. While the intrapericardial instillation of antibiotics (e.g., gentamycin) is useful, it is typically not sufficient by itself, and as such, it may be combined with general antibiotics treatment for a more effective treatment.

Additional methods to treat neoplastic pericardial effusions without tamponade may be utilized using a device, system and/or method of the present disclosure. For example, a systemic antineoplastic treatment may be performed to introduce drugs to inhibit and/or prevent the development of tumors. If a non-emergency condition exists (e.g., not a cardiac tamponade), a system and/or method of the present disclosure may be used to perform a pericardiocentesis. In addition, the present disclosure allows for the intrapericardial instillation of a cytostatic/sclerosing agent. It can be appreciated that using one or more of the devices, systems and/or methods disclosed herein, the prevention of recurrences may be achieved by intrapericardial instillation of sclerosing agents, cytotoxic agents, or immunomodulators, noting that the intrapericardial treatment may be tailored to the type of the tumor. Regarding chronic autoreactive pericardial effusions, the intrapericardial instillation of crystalloid glucocorticoids could avoid systemic side effects, while still allowing high local dose application.

A pacing lead may be placed on the external surface of the heart using an engagement catheter and a delivery catheter as disclosed herein. For example, an elongated tube of an engagement catheter is extended into a blood vessel so that the distal end of the tube is in contact with a targeted tissue on the interior of a wall of the heart. As explained above, the targeted tissue may be on the interior of the atrial wall or the atrial appendage. Suction is initiated to aspirate a portion of the targeted tissue to retract the cardiac wall away from the pericardial sac that surrounds the heart, thereby enlarging a pericardial space between the pericardial sac and the cardiac wall. A needle is then inserted through a lumen of the tube and advanced to the heart. The needle is inserted into the targeted tissue, causing a perforation of the targeted tissue. The distal end of a guide wire is inserted through the needle into the pericardial space to secure the point of entry through the cardiac wall. The needle is then withdrawn from the targeted tissue.

A delivery catheter, as described herein, is inserted into the lumen of the tube of the engagement catheter and over the guide wire. The delivery catheter may be a 14 Fr. radiopaque steering catheter. The distal end of the delivery catheter is advanced over the guide wire through the targeted tissue into the pericardial space. Once in the pericardial space, the delivery catheter is directed using a steering wire system as disclosed herein. In addition, a micro-camera system may be extended through the lumen of the delivery catheter to assist in the direction of the delivery catheter to the desired location in the pericardial space. Micro-camera systems suitable for use with the delivery catheter are well-known in the art. Further, a laser Doppler system may be extended through the lumen of the delivery catheter to assist in the direction of the delivery catheter. The delivery catheter is positioned such that the outlet of one of the lumens of the delivery catheter is adjacent to the external surface of the heart (e.g., the external surface of an atrium or a ventricle). A pacing lead is extended through the lumen of the delivery catheter onto the external surface of the heart. The pacing lead may be attached to the external surface of the heart, for example, by screwing the lead into the cardiac tissue. In addition, the pacing lead may be placed deeper into the cardiac tissue, for example in the subendocardial tissue, by screwing the lead further into the tissue. After the lead is placed in the proper position, the delivery catheter is withdrawn from the pericardial space and the body. The guide wire is withdrawn from the pericardial space and the body, and the engagement catheter is withdrawn from the body.

The disclosed embodiments can be used for subendocardial, as well as epicardial, pacing. While the placement of the leads is epicardial, the leads can be configured to have a long screw-like tip that reaches near the subendocardial wall. The tip of the lead can be made to be conducting and stimulatory to provide the pacing to the subendocardial region. In general, the lead length can be selected to pace transmurally at any site through the thickness of the heart wall. Those of skill in the art can decide whether epicardial, subendocardial, or some transmural location stimulation of the muscle is best for the patient in question.

Figure 23A:
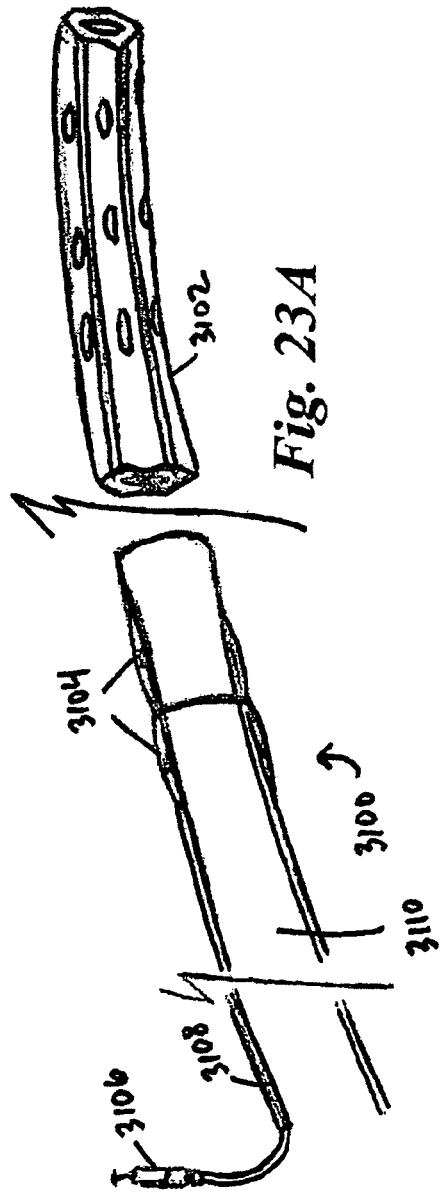
FIG. 23A shows an embodiment of a catheter system with a deflated balloon, as disclosed herein.
Figure 23B:
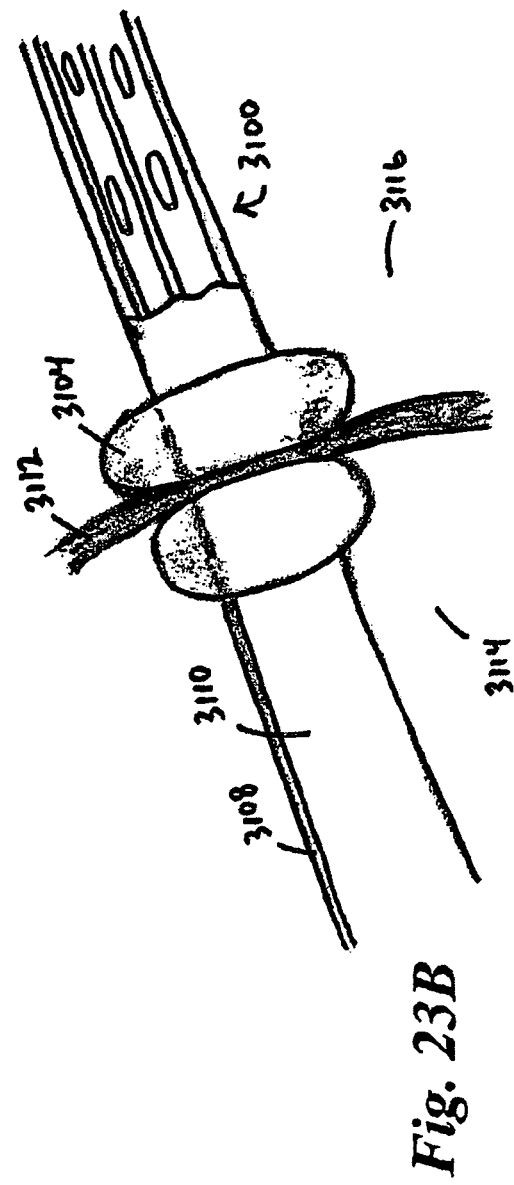
FIG. 23B shows an embodiment of a catheter system with an inflated balloon, as disclosed herein.

An embodiment of a catheter apparatus to improve heart function according to the present disclosure is shown in FIGS. 23A and 23B. As shown in FIG. 23A, catheter apparatus 3100 comprises a suction/infusion catheter 3102 and at least one balloon 3104 capable of inflation. Balloon 3104 may be coupled to a suction/inflation source 3106 via conduit 3108 coupling balloon 3104 to suction/inflation source 3106. In at least one embodiment, conduit 3108 comprises a tube positioned within a lumen 3110 of suction/infusion catheter 3102. In another embodiment, conduit 3108 comprises a tube positioned outside of suction/infusion catheter 3102, but positioned proximally to suction/infusion catheter 3102 so that suction/infusion catheter 3102 and conduit 3108 may be positioned within a body in a similar manner. It can be appreciated that conduit 3108 may also comprise a conduit positioned within a wall of suction/infusion catheter 3102, or may comprise a conduit coupled to either or both an inner or outer wall of suction/infusion catheter 3102.

As shown in FIG. 23A, balloon 3104 is coupled to suction/infusion catheter 3102. Balloon 3104 is shown in FIG. 23A in a deflated state, and is shown in an inflated state in the exemplary embodiment of catheter apparatus 3100 shown in FIG. 23B.

FIG. 23B shows an embodiment of catheter apparatus 3100 removably coupled to an atrial wall 3112 of a heart. As shown in FIG. 23B, catheter apparatus 3100 may be positioned through an aperture in atrial wall 3112 and may be removably coupled to atrial wall 3112 by inflation and/or deflation of balloon 3104. As shown in FIG. 23B, catheter apparatus 3100 may be positioned within an atrial cavity 3114, through atrial wall 3112, and into a pericardial space 3116, with the portion of catheter apparatus 3100 comprising balloon 3104 positioned at or near the atrial wall 3112. When positioned, inflation of balloon 3104 causes at least two portions of balloon 3104 to inflate, at least one portion of balloon 3104 inflating on either side of atrial wall 3112, or, in the alternative, inflation of balloon 3104 causes at least two balloons 3104 to inflate, at least one balloon 3104 positioned on either side of atrial wall 3112. When balloon 3104 is inflated, catheter apparatus 3100 becomes removably coupled to atrial wall 3112 and held in place for a period of time desired by a user of catheter apparatus 3100. It can be appreciated that more than one balloon 3104, as described above, may be coupled to catheter apparatus 3100, with inflation of multiple balloons occurring after inflation from one or more suction/infusion sources 3106. It can be further appreciated that catheter apparatus 3100 with balloon 3104 may be removably secured within an aperture of an atrial wall 3112 via inflation of balloon 3104 on substantially or fully on one side of atrial wall 3104, and a ridge, protrusion, or some other physical structure coupled to catheter apparatus 3100 on the other side of atrial wall 3112 may function to hold catheter apparatus 3100 in place when balloon 3104 is inflated.

Figure 24:
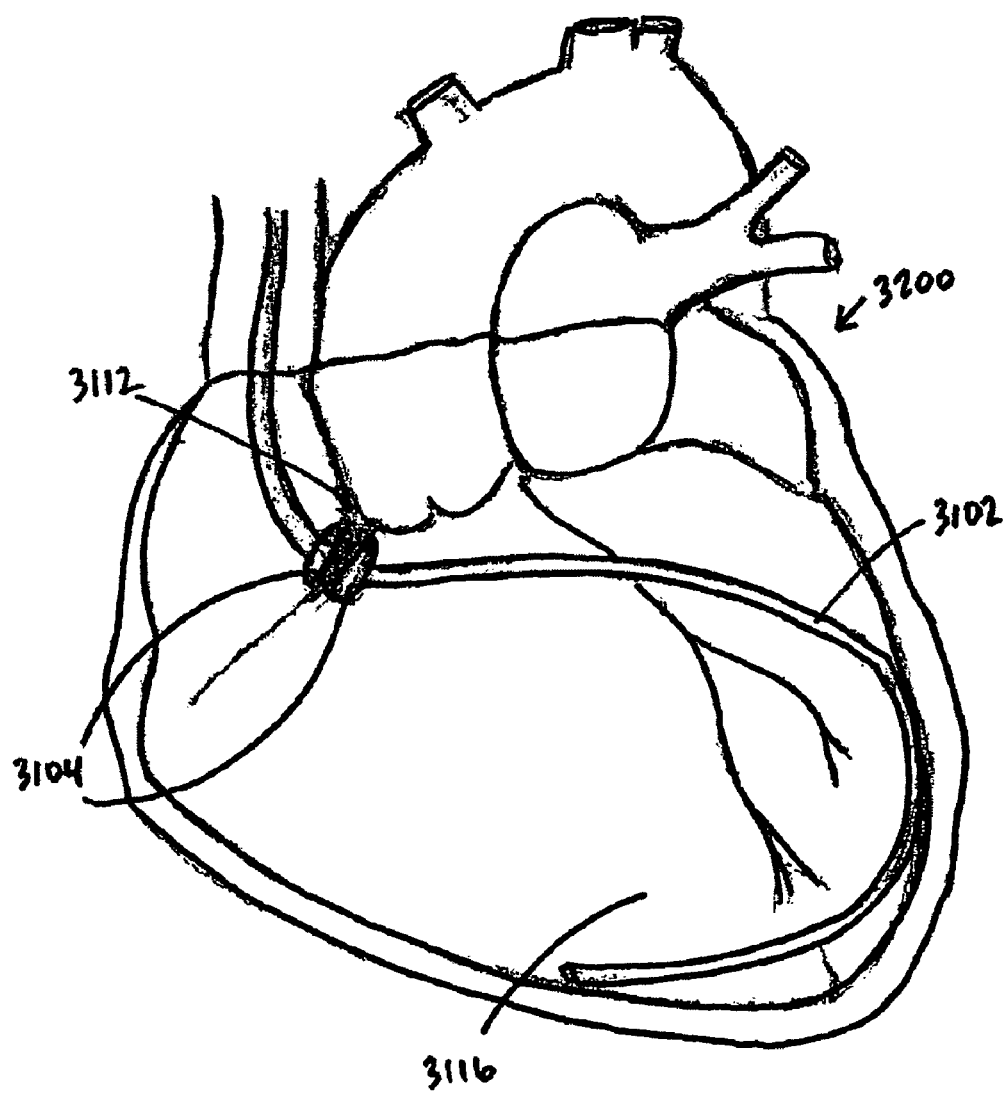
FIG. 24 shows an embodiment of a catheter system positioned within the pericardial space surrounding a heart, as disclosed herein.

FIG. 24 shows an embodiment of suction/infusion catheter 3102 positioned within a pericardial space 3116 surrounding a heart 3200. As shown in FIG. 24, suction/infusion catheter 3102 is positioned within an aperture of atrial wall 3112 and held in place via inflation of balloon 3104 of suction/infusion catheter 3102. Suction/infusion catheter 3102 may then be used to inject a substance, remove a substance via suction, or both, to or from a target site or target sites within and/or surrounding a heart 3200. In at least one embodiment, insertion of suction/infusion catheter 3102 is performed under local anesthesia.

FIGS. 25A and 25B show embodiments of a distal end of suction/infusion catheter 3102. As shown in FIG. 25A, suction/infusion catheter 3102 comprises at least one aperture 3300 positioned at or near the distal end of suction/infusion catheter 3102. As shown in the embodiment in FIGS. 25A and 25B, suction/infusion catheter 3102 defines multiple apertures 3300. Apertures 3300 are operably connected to an internal lumen defined within suction/infusion catheter 3102. It can be appreciated that the portion of suction/infusion catheter 3102 as shown in FIGS. 25A and 25B may be coupled to one or more portions of a catheter apparatus 3100 as described herein.

The internal lumen within suction/infusion catheter 3102 may define multiple internal channels. For example, suction/infusion catheter 3102 may define two channels, one channel operably coupled to one or more apertures 3300 to provide suction, and one channel operably coupled to one or more other apertures 3300 to allow for the injection of gas, liquid, and/or particulate(s) to a target site.

As described in further detail below, when suction/infusion catheter 3102 enters a space in a body (a pericardial sac, for example), suction/infusion catheter 3102 may be used to remove fluid by the use of suction through one or more apertures 3300. Suction/infusion catheter 3102 may also be used to deliver gas, liquid, and/or particulate(s) to a target site through one or more apertures 3300.

An exemplary embodiment of a portion of a distal end of a suction/infusion catheter 3102 is shown in FIG. 25B. As shown in FIG. 25B, suction/infusion catheter 3102 comprises a tube with multiple apertures 3300. However, in this exemplary embodiment, suction/infusion catheter 3102 comprises a number of concave grooves 3302 extending a portion of a length of suction/infusion catheter 3102, whereby the apertures 3300 are provided at the recessed portions therein. Concave grooves 3302, when positioned at least partially around the circumference of suction/infusion catheter 3102, define one or more ridges 3304 extending a portion of a length of suction/infusion catheter 3102. Said ridges 3304 of suction/infusion catheter 3102, when positioned at or near a tissue (not shown), aid to prevent a tissue from coming in direct contact with one or more apertures 3300.

An exemplary suction/infusion catheter 3102 may also comprise one or more pressure/volume sensors 3306 as shown in FIGS. 25A and 25B. Pressure/volume sensors 3306 may provide pressure and/or volume data/readings with respect to the amount of a gas (helium, for example) to be delivered to or from a pericardial sac 3116.

Figure 26:
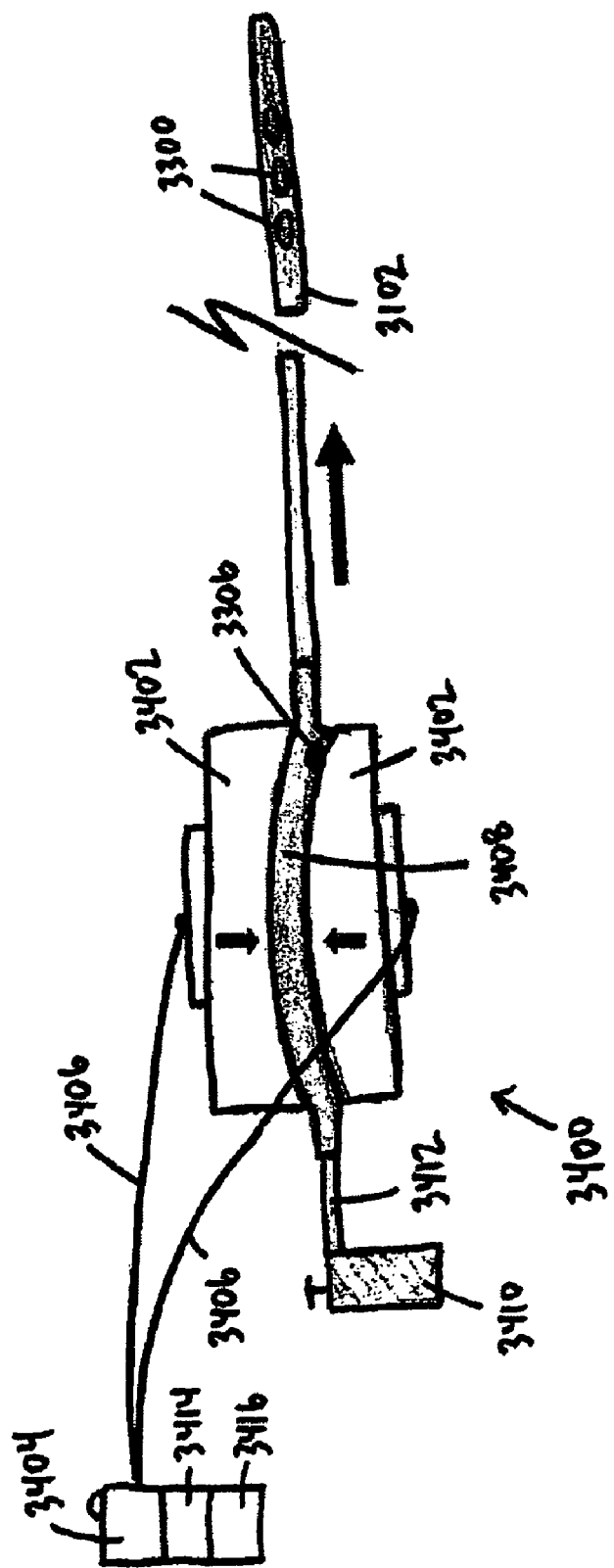
FIG. 26 shows an embodiment of a heart assist device with a deflated bladder, as disclosed herein.

An embodiment of a heart assist device 3400 of the present disclosure is shown in FIG. 26. As shown in FIG. 26, heart assist device 3400 comprises at least two electromagnetic plates 3402 coupled to a cardiac processor 3404. Cardiac processor 3404 may optionally be coupled to at least one electromagnetic plate 3402 via one or more wires 3406 as shown in FIG. 26. Bladder 3408 is positioned at least partially between electromagnetic plates 3402 and is either permanently or removably attached to electromagnetic plates 3402. In at least one exemplary embodiment, heart assist device 3400 comprises an electromagnetic plate and a non-electromagnetic plate. A cardiac processor 3404, which may be, for example, an electrocardiogram (EKG or ECG), operates to move electromagnetic plates 3402, wherein electromagnetic plates 3402 may move apart and/or together in relation to one another. As electromagnetic plates 3402 move about one another, bladder 3408 may inflate and/or deflate in relation to electromagnetic plates 3402. Bladder 3408 may comprise, for example, a polyurethane, a silastic, or another material suitable for proper function of bladder 3408. For example, if electromagnetic plates 3402 move apart from one another, bladder 3408, attached to electromagnetic plates 3402, would expand/inflate. Expansion/inflation of bladder 3408 may also be facilitated by a gas stored within reservoir 3410. In at least one embodiment, helium is used as a gas, and is stored within reservoir 3410.

The exemplary embodiment of heart assist device 3400 shown in FIG. 26 shows heart assist device 3400 in a relatively compressed state, denoting a "systolic time" of a heart 3200. As shown by the two vertical arrows appearing on electromagnetic plates 3402, when each electromagnetic plate 3402 moves in the direction of the vertical arrows, bladder 3408 may become compressed/deflated, and such compression/deflation may operate to move a gas in the direction of the horizontal arrow shown in FIG. 26 to suction/infusion catheter 3102 (or to a portion of a catheter apparatus 3100), whereby a gas may be expelled from one or more apertures 3300 into a space surrounding a heart 3200. A valve 3412 may be optionally positioned between reservoir 3410 and bladder 3408 to regulate the flow of a gas from reservoir 3410. In at least one embodiment, valve 3412 is a unilateral valve, regulating the flow of a gas from reservoir 3410 but not into reservoir 3410. A pressure/volume sensor 3306 may also be positioned along heart assist device 3400 to may provide pressure and/or volume data/readings with respect to the amount of a gas (helium, for example) to be delivered to or from a pericardial sac 3116.

An exemplary heart assist device 3400 of the present disclosure may also optionally comprise a power supply 3414 (a battery or a rechargeable battery, for example), to provide power to one or more features of heart assist device 3400, including, but not limited to, electromagnetic plates 3402, cardiac processor 3404, and a storage device 3416. Power supply 3414 and storage device 3416 may be coupled to cardiac processor, or may be coupled to other portions of heart assist device 3400 as may be available to allow for operation of heart assist device 3400. In at least one embodiment, power supply 3414 is positioned subcutaneously within a pectoral area of a patient. Storage device 3416 may retain measurements (heart data) including, but not limited to, general heart signals, emissions of signals, EKG systolic/diastolic time, heart rate ventricular volume, contraction signals, heart wall thickness, etc. (the aforementioned list being indicative of at least one parameter of heart data), and such measurements may be accessible by cardiac processor 3404 to allow for specific operation of heart assist device 3400. For example, if a heart 3200 is pumping at a rate slower than desired, cardiac processor 3404 may operate to increase the rate of heart pumping by increasing the rate of introduction and removal of a gas to and/or from a pericardial space 3116 as described herein, allowing heart assist device 3400 to function as a pacemaker. Conversely, if a heart 3200 is pumping at a rate faster than desired, cardiac processor 3404 may operate to decrease the rate of heart pumping by decreasing the rate of introduction and removal of a gas to and/or from a pericardial space 3116 as described herein. Cardiac processor 3404 may operate in such a manner based upon measurements stored within storage device 3416. In at least one embodiment, such operation is initiated following EKG signals received by heart assist device 3400 as described herein. In another embodiment, such operation is based upon information provided to cardiac processor 3404 from pressure/volume sensors 3306.

Figure 27:
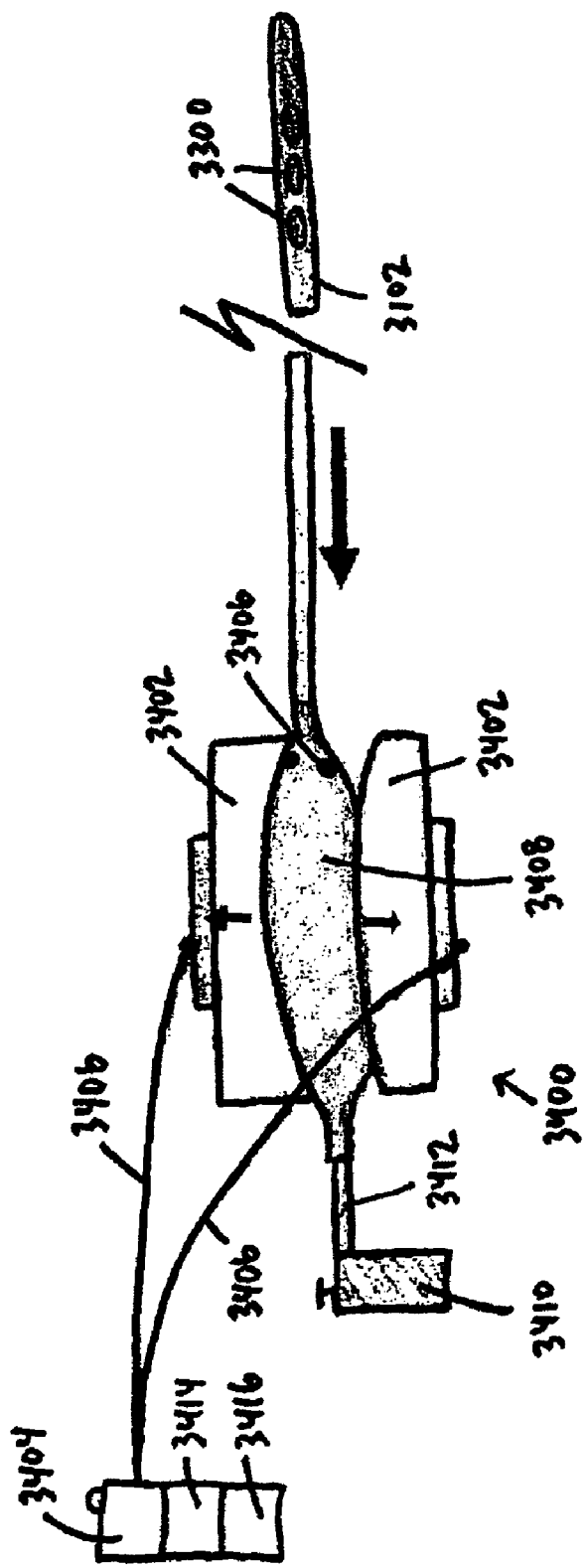
FIG. 27 shows an embodiment of a heart assist device with an inflated bladder, as disclosed herein.

Another embodiment of a heart assist device 3400 of the present disclosure is shown in FIG. 27. The exemplary embodiment of heart assist device 3400 shown in FIG. 27 may contain one or more elements as shown within the embodiment shown in FIG. 26, but is not limited to such elements, and may contain more or fewer elements as desired for a particular embodiment. For purposes of discussion of the exemplary embodiment shown in FIG. 27, the elements contained with the exemplary embodiment shown in FIG. 26 are also contained in the exemplary embodiment shown in FIG. 27.

The exemplary embodiment of heart assist device 3400 shown in FIG. 27 shows heart assist device 3400 in a relatively inflated state, denoting a "diastolic time" of a heart 3200. As shown by the two vertical arrows appearing on electromagnetic plates 3402, when each electromagnetic plate 3402 moves in the direction of the vertical arrows, bladder 3408 may become inflated, and such inflation may operate to move a gas in the direction of the horizontal arrow shown in FIG. 27 from suction/infusion catheter 3102, whereby a gas may be removed from a space surrounding a heart 3200 via one or more apertures 3300 along suction/infusion catheter 3102.

Figure 28:
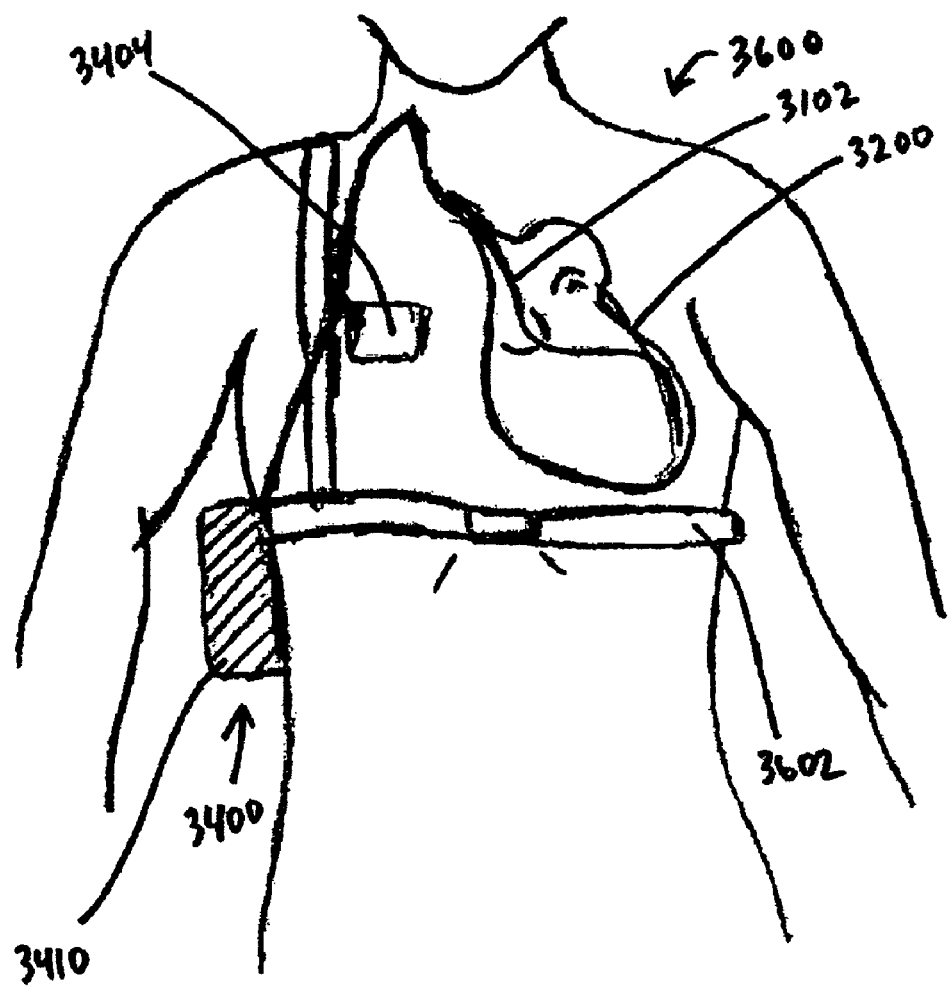
FIG. 28 shows a patient wearing an embodiment of a heart assist device, as disclosed herein.

FIG. 28 shows an exemplary embodiment of a patient wearing a heart assist device 3400 of the present disclosure. As shown in FIG. 28, patient 3600 is wearing heart assist device 3400, wherein heart assist device 3400 is secured to patient 3600 using, for example, an optional belt 3602. As shown in FIG. 28, reservoir 3410 is positioned externally to patient 3600. Heart assist device 3400 may operate in a similar function as described within FIGS. 26 and 27, whereby cardiac processor 3404 operates heart assist device 3400 to pump a gas in to and out from a space surrounding a heart 3200 via suction/infusion catheter 3102 to assist the functionality of heart 3200. Such a heart assist device 3400 may optimally be relatively small, lightweight, portable, rechargeable, and easy for a patient 3600 to carry.

Figure 29A:
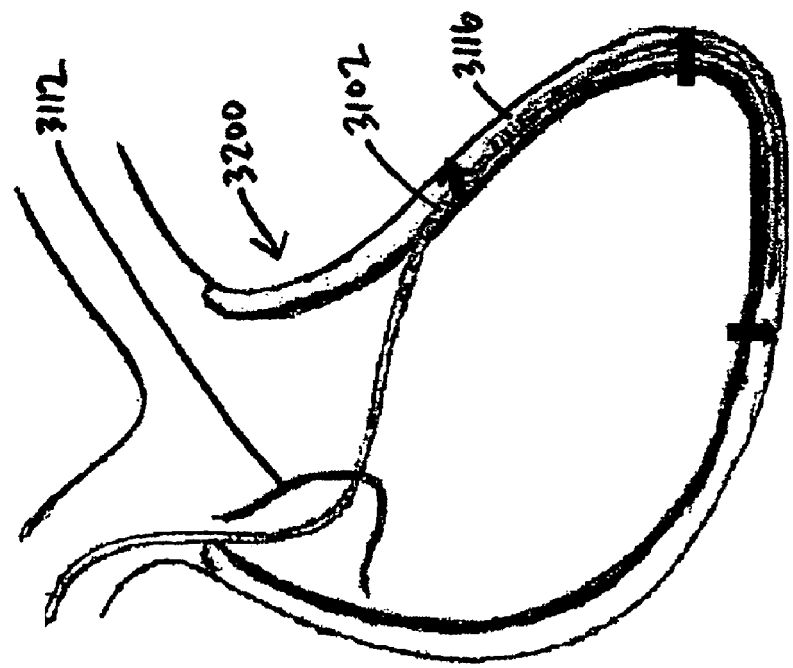
FIG. 29A shows an embodiment of a suction/infusion catheter positioned within an inflated pericardial space, as disclosed herein.

FIG. 29A shows an embodiment of a suction/infusion catheter 3102 of a catheter apparatus 3100 positioned within a heart 3200, through an atrial wall 3112, and into a pericardial space 3116. Suction/infusion catheter 3102 may be operable to introduce a gas (helium, for example), into pericardial space 3116, during "systolic time" as described herein. In systole, as determined by EKG, for example, the infusion of a gas from pericardial space 3116 is made to compress heart 3200 and reduce heart 3200 wall dimensions, resulting in a decrease in wall stress. During contraction of heart 3200 ("systolic time"), pericardial space 3116 may partially fill with a gas, assisting heart 3200 with its contraction. The synchronized compressive pressure by the gas in the pericardial space 3116 over heart 3200 during the systolic time reinforces the blood ejection from the ventricles of heart 3200.

A gas may be introduced into pericardial space 3116 as described within the description relating to FIG. 26 herein. Expansion of a pericardial space 3116 using a gas exerts pressures on the various walls of heart 3200 as shown by the arrows in FIG. 29A. Such an expansion may not only assist the heart 3200 with its contraction function, but may also provide additional beneficial support to a pericardial wall.

Figure 29B:
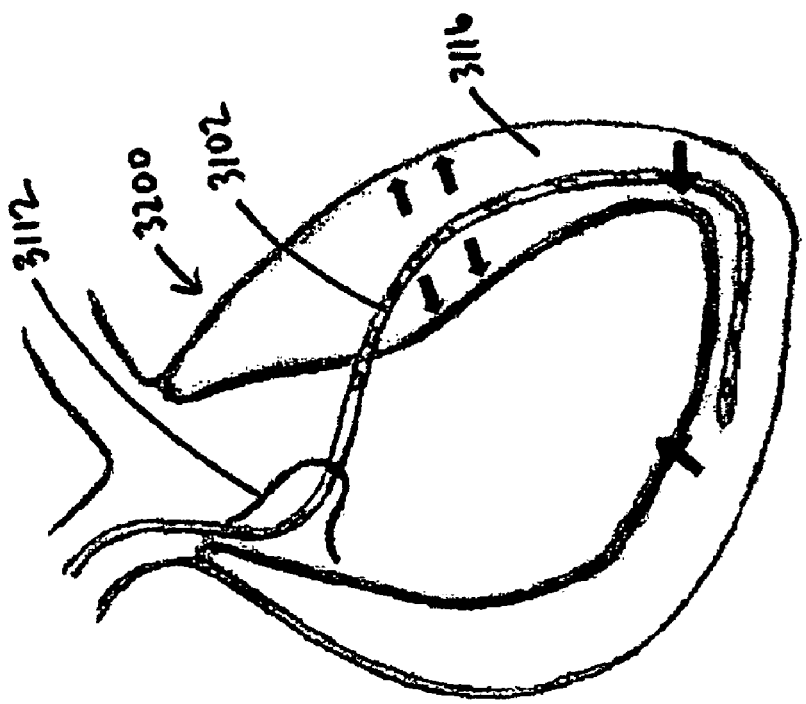
FIG. 29B shows an embodiment of a suction/infusion catheter positioned within an inflated pericardial space, as disclosed herein.

FIG. 29B also shows an embodiment of a suction/infusion catheter 3102 of a catheter apparatus 3100 positioned within a heart 3200, through an atrial wall 3112, and into a pericardial space 3116. Suction/infusion catheter 3102 may be operable to introduce remove a gas (helium, for example), from pericardial space 3116, during "diastolic time" as described herein. In diastole, as determined by EKG, for example, the removal of a gas from pericardial space 3116 is made to un-load heart 3200 and increase myocardial flow, resulting in increased perfusion. The deflation of the pericardial space 3116 due to gas suction during diastolic time reduces the compressive pressure over the heart 3200 and facilitates the expansion/filling of the chambers of heart 3200 with blood. A gas may be removed from pericardial space 3116 as described within the description relating to FIG. 27 herein.

During expansion of heart 3200 ("diastolic time"), gas may partially or fully expel from pericardial space 3116, assisting heart 3200 with its expansion. Removal of gas from pericardial space 3116 assists the expansion of an internal heart chamber as shown by the arrows in FIG. 29B, noting that as gas is expelled from a pericardial space 3116, the innermost pericardial wall would be pulled inward (as shown by the arrows), assisting with the expansion of a chamber of heart 3200 as it fills with blood. As such, pericardial space 3116 functions as a pump bladder of heart 3200 using a catheter apparatus 3100 of the present disclosure. For example, the parietal pericardium and the visceral pericardium have pumping characteristics of a pump bladder, wherein a gas inflates the pump bladder to provide a compressive pressure on heart 3200 during systolic time and deflating the pump bladder by gas suction during diastolic time. Furthermore, the amount of gas may be increased and/or decreased as desired according to hemodynamic parameters made available to cardiac processor 3404.

FIGS. 30A and 30B show embodiments of a distal end of suction/infusion catheter 3102 with a pericardial balloon 3700 coupled thereto. As shown in FIG. 30A, suction/infusion catheter 3102 comprises at least one aperture 3300 positioned at or near the distal end of suction/infusion catheter 3102. As shown in the embodiments in FIGS. 30A and 30B, suction/infusion catheter 3102 defines multiple apertures 3300. Apertures 3300 are operably connected to an internal lumen defined within suction/infusion catheter 3102. It can be appreciated that the portion of suction/infusion catheter 3102, as shown in FIGS. 30A and 30B, may be coupled to one or more portions of a catheter apparatus 3100 as described herein.

The exemplary embodiment of a suction/infusion catheter 3102 shown in FIG. 30A is shown with a deflated pericardial balloon 3700. In at least one procedure wherein suction/infusion catheter 3102 is introduced into a pericardial space 3116 surrounding a heart 3200, suction/infusion catheter 3102 may have a deflated pericardial balloon 3700 coupled thereto, so that suction/infusion catheter 3102 may be more readily inserted into the pericardial space 3116. As shown in the embodiment shown in FIG. 30B, suction/infusion catheter 3102 is shown with an inflated pericardial balloon 3700. In at least one procedure wherein suction/infusion catheter 3102 is introduced into a pericardial space 3116 surrounding a heart 3200, pericardial balloon 3700 may be inflated by an inflation source, including, but not limited to, suction/inflation source 3106. It can be appreciated that any number of inflation sources known in the art may be used to inflate pericardial balloon 3700.

Pericardial balloon 3700 may comprise any material suitable for a particular application, including, but not limited to, a polyurethane pericardial balloon 3700, and may comprise any number of inflated pericardial balloon 3700 volumes, including, but not limited to, a 30 cc or a 40 cc pericardial balloon 3700.

Figure 31B:
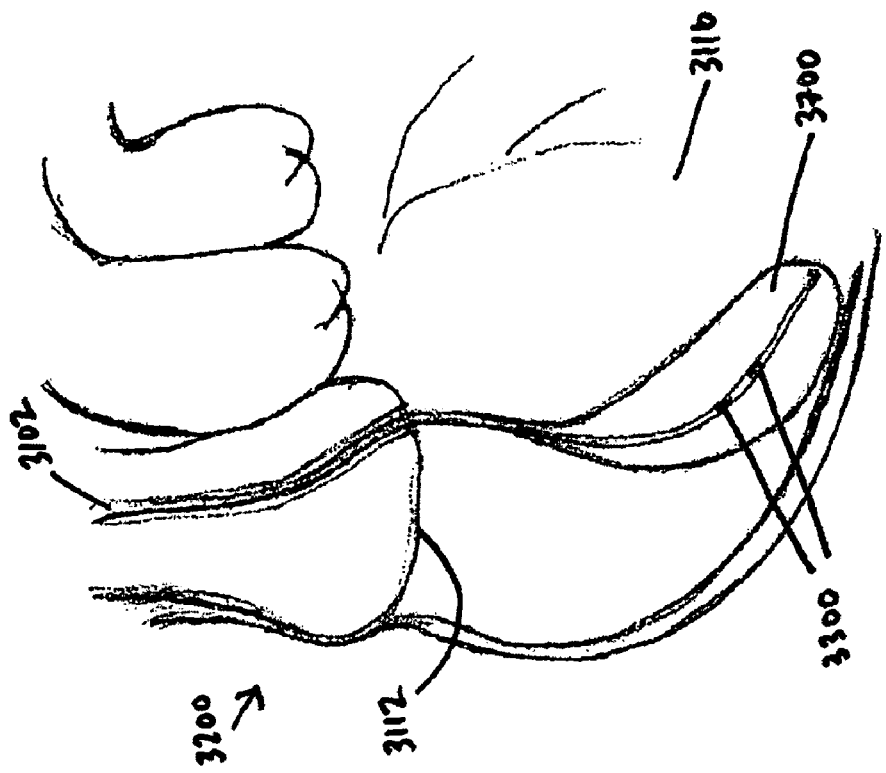
FIG. 31B shows the embodiment of FIG. 31A with an inflated pericardial balloon.
Figure 31A:
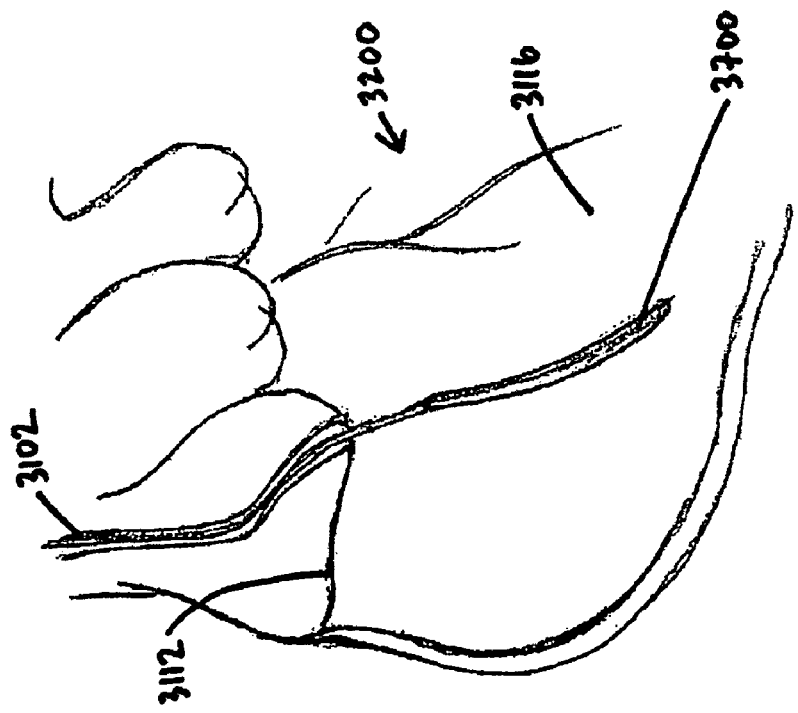
FIG. 31A shows an embodiment of a suction/infusion catheter positioned within a pericardial space surrounding a heart, as disclosed herein.

FIGS. 31A and 31B show exemplary embodiments of suction/infusion catheter 3102 positioned within the pericardial space 3116 surrounding a heart 3200. In the exemplary embodiment shown in FIG. 31A, suction/infusion catheter 3102 is shown positioned within an atrial appendage, through an atrial wall 3112, and into the pericardial space 3116 surrounding the heart 3200. In this embodiment, suction/infusion catheter 3102 comprises a pericardial balloon 3700 positioned at or near the distal end of suction/infusion catheter 3102, wherein pericardial balloon 3700 is deflated (during "diastolic time"). This exemplary embodiment and other embodiments may be coupled to and become part of a device and/or apparatus of the present disclosure.

As shown in FIG. 31B, an exemplary embodiment of a suction/infusion catheter 3102 positioned within the pericardial space 3116 surrounding a heart 3200 is shown. In this exemplary embodiment, pericardial balloon 3700 is shown positioned within the pericardial space 3116 surrounding heart 3200 with pericardial balloon 3700 inflated (during "systolic time"). Pericardial balloon 3700 may be inflated using suction/inflation source 3106, or using another inflation source operably coupled to the internal lumen of suction/infusion catheter 3102, wherein gas may be introduced into the lumen of suction/infusion catheter by, for example, a suction/inflation source 3106 or another inflation source coupled to the suction/infusion catheter 3102, to enter pericardial balloon 3700 via the one or more apertures 3300 defined therethrough. In at least one embodiment, a conduit (not shown) may be used to connect suction/inflation source 3106 or another inflation source to pericardial balloon 3700 to facilitate inflation and/or deflation of pericardial balloon 3700. As will be provided in further detail herein, positioning a suction/infusion catheter 3102 within a specific area within the pericardial space 3116 surrounding the heart 3200 will allow for localized inflation and/or deflation of the pericardial balloon 3700, allowing the pericardial balloon 3700 to potentially contact the epiardial wall at or near a desired chamber of a heart 3200.

FIGS. 32A and 32B show exemplary embodiments of suction/infusion catheters 3012 comprising pericardial balloons 3700 positioned within the pericardial space 3116 surrounding a heart 3200. A shown in FIG. 32A, suction/infusion catheter 3102 is positioned through an aperture in the atrial wall 3112 and into the pericardial space 3116 surrounding a heart 3200. In this embodiment, suction/infusion catheter 3102 is positioned within the pericardial space 3116 near the left ventricle of the heart 3200. In this exemplary embodiment, pericardial balloon 3700 may be inflated during systolic time of the heart 3200, facilitating a heart beat. For example, if a heart 3200 is damaged, and the left ventricle is unable to properly beat to pump blood, positioning a suction/infusion catheter 3102 within the pericardial space 3116 near the left ventricle of the heart 3200, and inflating the pericardial balloon during systolic time, the natural beat of the heart 3200 along with the inflation of pericardial balloon 3700 exerting pressure on the epicardial wall outside the left ventricle would facilitate a stronger heart beat, and thus overall heart 3200 function.

FIG. 32B shows an exemplary embodiment of a device/apparatus as described herein comprising multiple suction/infusion catheters 3102. In this exemplary embodiment, two suction/infusion catheters 3102 are provided, with each suction/infusion catheter 3102 comprising a pericardial balloon 3700. It can be appreciated that a device/apparatus of the present disclosure may comprise any number and/or types of catheters, including, but not limited to, multiple suction/infusion catheters 3102, as may be desired for a particular application.

In the exemplary embodiment shown in FIG. 32B, one suction/infusion catheter 3102 is positioned within the pericardial space 3116 at or near the left ventricle of the heart 3200, and another suction/infusion catheter 3102 is positioned within the pericardial space 3116 at or near the right ventricle of the heart 3200. An embodiment comprising two or more suction/infusion catheters 3102 with pericardial balloons 3700 allow for inflation and/or deflation of two pericardial balloons 3700 either at the same time, allowing for "counterpulsation" of the two balloons 3700 when inflated and/or deflated. As a pericardial balloon 3700 positioned within a pericardial space 3116 is inflated, pericardial balloon 3700 may exert a pressure against the epicardial wall, with such pressure facilitating the beating of a heart 3200.

Several advantages exist for a catheter system 3100 and heart assist device 3400 of the present disclosure, including non-blood contact (as at least a portion of catheter system 3100 would be positioned within a pericardial space 3116 when in use), and that no intravascular power source, pumps, and or valves are required. As portions of such a system/device may be introduced to a patient 3600 under local anesthesia, as no formal/invasive surgical procedure is required, reducing risks of infection, embolism, bleeding, and material fatigue.

In addition, portions of a system/device are relatively easy to insert and remove, and as such a system/device does not require the use of pharmaceuticals, no drug treatment contraindications would exist. Furthermore, as a reservoir 3410 would be positioned externally to the body of a patient 3600, it may be completely rechargeable without patient 3600 complication during the replacement period. Such a system/device may also measure on line cardiac rhythm, ventricular volumes displacements, pressure, etc., to tailor the treatment for a specific patent 3600. Furthermore, such a system/device would allow a patient 3600 to be freely mobile without discomfort.

It can be appreciated that a heart assist device 3400 as described herein may comprise other means of injecting and/or removing a gas from a pericardial space 3116. For example, and instead of using one or more electromagnetic plates 3402 and a bladder 3408, heart assist device may instead use a piston as the gas injection/removal mechanism, whereby said piston have the same effect in operation as the operation of a heart assist device using one or more electromagnetic plates 3402 and a bladder 3408 as described herein.

While various embodiments of devices, systems, and methods for accessing the heart tissue and assisting heart function have been described in considerable detail herein, the embodiments are merely offered by way of non-limiting examples of the disclosure described herein. Many variations and modifications of the embodiments described herein wilt be apparent to one of ordinary skill in the art in light of this disclosure. It will therefore be understood by those skilled in the art that various changes and modifications may be made, and equivalents may be substituted for elements thereof, without departing from the scope of the disclosure. Indeed, this disclosure is not intended to be exhaustive or to limit the scope of the disclosure. The scope of the disclosure is to be defined by the appended claims, and by their equivalents.

Further, in describing representative embodiments, the disclosure may have presented a method and/or process as a particular sequence of steps. However, to the extent that the method or process does not rely on the particular order of steps set forth herein, the method or process should not be limited to the particular sequence of steps described. As one of ordinary skill in the art would appreciate, other sequences of steps may be possible. Therefore, the particular order of the steps disclosed herein should not be construed as limitations on the claims. In addition, the claims directed to a method and/or process should not be limited to the performance of their steps in the order written, and one skilled in the art can readily appreciate that the sequences may be varied and still remain within the spirit and scope of the present disclosure.

It is therefore intended that the disclosure will include, and this description and the appended claims will encompass, all modifications and changes apparent to those of ordinary skill in the art based on this disclosure.

We claim:

1. A device for assisting heart function, comprising:
   at least two electromagnetic plates, the at least two electromagnetic plates having an inner surface;
   a cardiac processor electrically coupled to at least one of the at least two electromagnetic plates;
   a bladder having an inner chamber, the bladder attached to inner surfaces of each of the at least two electromagnetic plates and disposed between the at least two electromagnetic plates;
   a source of gas in communication with the inner chamber of the bladder; and
   a catheter having a proximal end and a distal end and having a lumen therethrough, the catheter defining at least one aperture positioned therethrough at or near the distal end of the catheter, the proximal end of the catheter in communication with the inner chamber of the bladder.

2. The device of claim 1, wherein the at least two electromagnetic plates are operable to compress the bladder, wherein the compression of the bladder, when the distal end of the catheter is positioned within a pericardial space, injects gas directly into the pericardial space.

3. The device of claim 1, wherein the at least two electromagnetic plates are operable to compress and expand the bladder, and wherein the compression and expansion is facilitated using one or more actuators operably coupled to the one or more electromagnetic plates.

4. The device of claim 1, wherein the at least two electromagnetic plates are operable to expand the bladder, wherein the expansion of the bladder, when the distal end of the catheter is positioned within a pericardial space, removes gas from the pericardial space.

5. The device of claim 1, wherein the cardiac processor comprises heart data, the heart data comprising at least one parameter, and wherein the cardiac processor is operable to cause the at least two electromagnetic plates to compress and/or expand the bladder based upon the at least one parameter of the heart data.

6. The device of claim 1, further comprising at least one pressure/volume sensor operably coupled to the catheter, wherein the at least one pressure/volume sensor operates to provide pressure and/or volume data to the cardiac processor, the pressure and/or volume data relating to the pressure and/or volume of gas detected at the at least one pressure/volume sensor.

7. The device of claim 1, wherein the source of gas comprises a portable gas reservoir.

8. The device of claim 1, wherein when the distal end of the catheter is positioned within a pericardial space, gas enters the pericardial space from the bladder, through the lumen of the catheter, and out from the at least one aperture defined within the catheter.

9. The device of claim 1, wherein when the distal end of the catheter is positioned within a pericardial space, gas is removed from the pericardial space through the at least one aperture defined within the catheter, through the lumen of the catheter, and into the bladder.

10. The device of claim 1, further comprising a valve positioned between the source of gas and the bladder, wherein the valve is a unilateral valve operable to allow gas to flow from the source of gas.

11. The device of claim 1, further comprising a power supply operably coupled to the cardiac processor.

12. The device of claim 1, further comprising a data storage device in communication with the cardiac processor, wherein the cardiac processor is operable to cause the at least two electromagnetic plates to compress and/or expand the bladder based upon data stored within the data storage device.

13. The device of claim 12, wherein the cardiac processor is operable to increase a frequency of compression of the bladder from a first compression rate to a second compression rate, causing a heart to beat at a faster rate.

14. The device of claim 12, wherein the cardiac processor is operable to decrease a frequency of compression of the bladder from a first compression rate to a second compression rate, causing a heart to beat at a slower rate.

15. The device of claim 1, wherein at least a portion of the device is adapted to be positioned externally to a patient's body, and wherein at least a portion of the device is adapted to be positioned within a patient's body.

16. The device of claim 15, further comprising at least one belt coupled to the source of gas, wherein the at least one belt may be secured externally to the patient's body to secure the source of gas to the patient's body.

17. The device of claim 1, wherein at least one balloon is coupled to the catheter and positioned externally to the catheter.

18. The device of claim 17, the device further comprising a conduit having a proximal end and a distal end, the distal end of the conduit coupled to the at least one balloon, wherein when the catheter is positioned within an aperture in an atrial wall and when the at least one balloon is positioned at or near the aperture in the atrial wall, inflation of the at least one balloon causes the catheter to be held in place at the atrial wall.

19. The device of claim 18, wherein the inflation of the at least one balloon causes a first portion of the at least one balloon to inflate on a first side of the atrial wall, and further causes a second portion of the at least one balloon to inflate on a second side of the atrial wall, securing the catheter in place at the atrial wall.

20. The device of claim 18, wherein the at least one balloon comprises a first balloon and a second balloon, wherein when the catheter is positioned within an aperture of an atrial wall, wherein the first balloon is positioned on a first side of the atrial wall and wherein the second balloon is positioned on a second side of the atrial wall, the catheter is held in place at the atrial wall when the first balloon and the second balloon are inflated.

21. The device of claim 18, further comprising a protrusion coupled to the catheter and positioned externally to the catheter, wherein the protrusion is positioned at or near the at least one balloon, and wherein when the catheter is positioned within the aperture of an atrial wall and wherein the at least one balloon is positioned on one side of the atrial wall and the protrusion is positioned on an opposite side of the atrial wall, the catheter is held in place at the atrial wall when the at least one balloon is inflated.

22. The device of claim 1, wherein the device further comprises a pericardial balloon coupled to the at least one catheter at or near the distal end of the at least one catheter, and wherein when the distal end of the at least one catheter is positioned within a pericardial space, the device operates to inject gas and/or remove gas from the pericardial balloon.

23. A method of assisting heart function, the method comprising the steps of:
providing a device for assisting heart function, comprising:
at least two electromagnetic plates, the at least two electromagnetic plates having an inner surface;
a cardiac processor electrically coupled to at least one of the at least two electromagnetic plates;
a bladder having a an inner chamber, the bladder attached to an inner surface of at least one of the at least two electromagnetic plates;
a source of gas in communication with the inner chamber of the bladder; and
a catheter having a proximal end and a distal end and having a lumen therethrough, the catheter defining at least one aperture positioned therethrough at or near the distal end of the catheter, the proximal end of the catheter in communication with the inner chamber of the bladder; and
operating the device to inject gas into and/or remove gas from the pericardial space to assist heart function, such that the gas is in contact with pericardial tissue.

24. The method of claim 23, wherein gas enters the pericardial space from the bladder, through the lumen of the catheter, and out from the at least one aperture defined within the catheter, and wherein gas is removed from the pericardial space through the at least one aperture defined within the catheter, through the lumen of the catheter, and into the bladder.

25. The method of claim 23, wherein the device further comprises a data storage device in communication with the cardiac processor, wherein the cardiac processor is operable to cause the at least two electromagnetic plates to compress and/or expand the bladder based upon data stored within the data storage device.

26. The method of claim 25, wherein the cardiac processor is operable to increase a frequency of compression of the bladder from a first compression rate to a second compression rate, causing a heart to beat at a faster rate.

27. The method of claim 25, wherein the cardiac processor is operable to decrease a frequency of compression of the bladder from a first compression rate to a second compression rate, causing a heart to beat at a slower rate.

28. The method of claim 23, wherein the step of operating the device to inject gas directly into and/or remove gas from the pericardial space to assist heart function is performed by injecting gas directly into the pericardial space while the heart is in systole and removing gas from the pericardial space while the heart is in diastole, to assist heart function.

29. A device for assisting heart function, comprising:
at first electromagnetic plate, the first electromagnetic plate having an inner surface;
a first non-electromagnetic plate, the first non-electromagnetic plate having an inner surface;
a cardiac processor electrically coupled to the first electromagnetic plate;
a bladder having a proximal end, a distal end, and an inner chamber, the bladder attached to inner surfaces of the first electromagnetic plate and the first non-electromagnetic plate and disposed between the first electromagnetic plate and the first non-electromagnetic plate;
a source of gas in communication with the inner chamber of the bladder at the proximal end of the bladder; and
a catheter having a proximal end and a distal end and having a lumen therethrough, the catheter defining at least one aperture positioned therethrough at or near the distal end of the catheter, the proximal end of the catheter in communication with the inner chamber of the bladder at the distal end of the bladder.

* * * * *